(12) United States Patent
Verzal et al.

(10) Patent No.: US 11,219,761 B2
(45) Date of Patent: Jan. 11, 2022

(54) ATTENUATION ARRANGEMENT FOR IMPLANTABLE MEDICAL DEVICE

(71) Applicant: INSPIRE MEDICAL SYSTEMS, INC., Maple Grove, MN (US)

(72) Inventors: Kevin Verzal, Maple Grove, MN (US); John Rondoni, Maple Grove, MN (US); David Dieken, Maple Grove, MN (US)

(73) Assignee: INSPIRE MEDICAL SYSTEMS, INC., Golden Valley, MN (US)

(*) Notice: Subject to any disclaimer, the term of this patent is extended or adjusted under 35 U.S.C. 154(b) by 26 days.

(21) Appl. No.: 16/092,387

(22) PCT Filed: May 11, 2017

(86) PCT No.: PCT/US2017/032107
§ 371 (c)(1),
(2) Date: Oct. 9, 2018

(87) PCT Pub. No.: WO2017/197084
PCT Pub. Date: Nov. 16, 2017

(65) Prior Publication Data
US 2019/0175906 A1    Jun. 13, 2019

Related U.S. Application Data

(60) Provisional application No. 62/334,774, filed on May 11, 2016.

(51) Int. Cl.
*A61N 1/08* (2006.01)
*A61N 1/05* (2006.01)
*A61N 1/06* (2006.01)

(52) U.S. Cl.
CPC ............... *A61N 1/086* (2017.08); *A61N 1/05* (2013.01); *A61N 1/06* (2013.01)

(58) Field of Classification Search
CPC ............. A61N 1/086; A61N 1/06; A61N 1/05
USPC .......................................................... 607/116
See application file for complete search history.

(56) References Cited

U.S. PATENT DOCUMENTS

| | | |
|---|---|---|
| 6,944,489 B2 | 9/2005 | Zeijlemaker |
| 6,985,775 B2 | 1/2006 | Reinke et al. |
| 7,369,898 B1 | 5/2008 | Kroll et al. |
| 7,509,167 B2 | 3/2009 | Stressman |
| 7,561,915 B1 | 7/2009 | Cooke et al. |
| 7,844,319 B2 | 11/2010 | Susil et al. |
| 7,877,150 B2 | 1/2011 | Hoegh et al. |
| 8,014,867 B2 | 9/2011 | Cooke et al. |
| 8,032,230 B1 | 10/2011 | Cox et al. |
| 8,055,351 B2 | 11/2011 | Atalar et al. |

(Continued)

FOREIGN PATENT DOCUMENTS

WO    2011051872    5/2011

OTHER PUBLICATIONS

Wonderful PCB Limited, Brief Classification of Flexible Printed Circuits (FPC), Source Tech 411, Dec. 3, 2013, 3 pages.
(Continued)

*Primary Examiner* — Erin M Piateski
(74) *Attorney, Agent, or Firm* — Dicke, Billig & Czaja, PLLC

(57) ABSTRACT

An implantable medical device includes at least one conductive element and an associated attenuation arrangement to attenuate MRI energy.

21 Claims, 33 Drawing Sheets

(56) References Cited

U.S. PATENT DOCUMENTS

| | | |
|---|---|---|
| 8,200,334 B1 | 6/2012 | Min et al. |
| 8,364,286 B2 | 1/2013 | Hoegh et al. |
| 8,412,351 B2 | 4/2013 | Zeijlemaker et al. |
| 8,521,254 B2 | 8/2013 | Doerr et al. |
| 8,527,046 B2 | 9/2013 | Connelley et al. |
| 8,606,365 B2 | 12/2013 | Sison |
| 8,620,454 B2 | 12/2013 | Wahlstrand et al. |
| 8,761,899 B2 | 6/2014 | Lloyd et al. |
| 8,761,900 B2 | 6/2014 | Lloyd et al. |
| 8,805,540 B2 | 8/2014 | Lloyd et al. |
| 8,831,743 B2 | 9/2014 | Lloyd et al. |
| 8,843,212 B2 | 9/2014 | Lloyd et al. |
| 8,843,213 B2 | 9/2014 | Lloyd et al. |
| 8,868,208 B2 | 10/2014 | Seifert |
| 8,996,126 B2 | 3/2015 | Stevenson et al. |
| 8,996,134 B2 | 3/2015 | Duncan et al. |
| 9,020,610 B2 | 4/2015 | Zeijlemaker |
| 9,089,695 B2 | 7/2015 | Seifert et al. |
| 9,226,688 B2 | 1/2016 | Jacobsen et al. |
| 9,226,689 B2 | 1/2016 | Jacobsen et al. |
| 9,226,800 B2 | 1/2016 | Burg et al. |
| 9,232,985 B2 | 1/2016 | Jacobsen et al. |
| 9,242,090 B2 | 1/2016 | Atalar et al. |
| 10,183,166 B2 | 1/2019 | Gururaj et al. |
| 2003/0144718 A1 | 7/2003 | Zeijlemaker |
| 2003/0144719 A1 | 7/2003 | Zeijlemaker |
| 2004/0230114 A1* | 11/2004 | Clatterbaugh ........ A61M 25/00 600/435 |
| 2005/0065587 A1 | 3/2005 | Gryzwa |
| 2005/0070972 A1 | 3/2005 | Wahlstrand et al. |
| 2005/0222658 A1 | 10/2005 | Hoegh et al. |
| 2006/0200218 A1* | 9/2006 | Wahlstrand .......... A61N 1/0551 607/116 |
| 2006/0247747 A1 | 11/2006 | Olsen et al. |
| 2006/0293591 A1 | 12/2006 | Wahstrand |
| 2007/0088416 A1* | 4/2007 | Atalar .................... A61N 1/08 607/115 |
| 2007/0112398 A1* | 5/2007 | Stevenson ............... H01G 4/40 607/63 |
| 2008/0119919 A1 | 5/2008 | Atalar et al. |
| 2008/0243218 A1* | 10/2008 | Bottomley ............. A61N 1/05 607/116 |
| 2008/0269831 A1 | 10/2008 | Erickson |
| 2010/0094364 A1 | 4/2010 | McDonald |
| 2010/0106227 A1* | 4/2010 | Min ..................... A61N 1/3718 607/63 |
| 2011/0015713 A1* | 1/2011 | Min ........................ A61N 1/37 607/116 |
| 2011/0029036 A1* | 2/2011 | Yamamoto ........... A61N 1/3754 607/36 |
| 2011/0077708 A1 | 3/2011 | Ostroff |
| 2011/0152990 A1* | 6/2011 | Shehada ................. A61N 1/05 607/127 |
| 2012/0078333 A1* | 3/2012 | Westlund ............. H03H 1/0007 607/118 |
| 2012/0203100 A1* | 8/2012 | Weiss .................... A61N 1/06 600/421 |
| 2012/0209365 A1* | 8/2012 | Seifert .................... A61N 1/05 607/116 |
| 2014/0012130 A1* | 1/2014 | Jacobsen ................ A61B 5/065 600/424 |
| 2014/0113828 A1* | 4/2014 | Gilbert ................. H01L 39/225 505/100 |
| 2014/0114379 A1 | 4/2014 | Seifert et al. |
| 2015/0031975 A1 | 1/2015 | Atalar et al. |
| 2015/0207484 A1* | 7/2015 | Stevenson ............... A61N 1/05 333/206 |
| 2016/0331960 A1* | 11/2016 | Katnani ............... A61N 1/0534 |
| 2017/0106186 A1 | 4/2017 | Thompson et al. |

OTHER PUBLICATIONS

Bottomley et al., Designing passive MRI-save implantable conducting leads with electrodes, PubMed-NCBI, Jul. 2010, 1 page.

Gray et al., Simple design changes to wires to substantially reduce MRI-induced heating at 1.5T: implications for implant leads, PubMed-NCBI, Oct. 2005, 1 page.

Bottomley PA, Kumar A, Edelstein WA, Allen JM, and Karmarkar PV, "Designing passive MRI-safe implantable conducting leads with electrodes," Med Phys., vol. 37, No. 7, Jul. 2010, pp. 3828-3843.

Gray RW, Bibens WT, and Shellock FG, "Simple design changes to wires to substantially reduce MRI-induced heating at 1.5 T: implications for implanted leads," Magn Reson Imaging, vol. 23, No. 8, Epub. Oct. 2005, pp. 887-891.

* cited by examiner

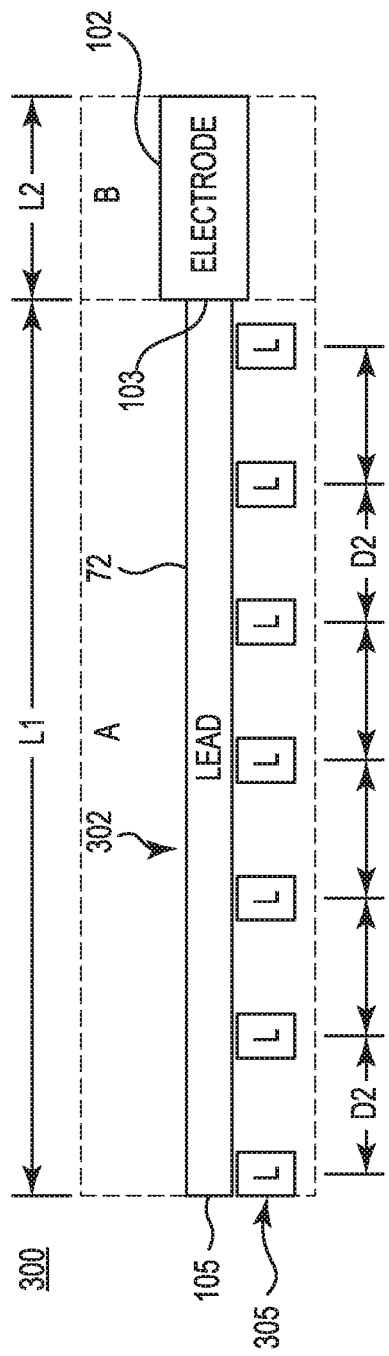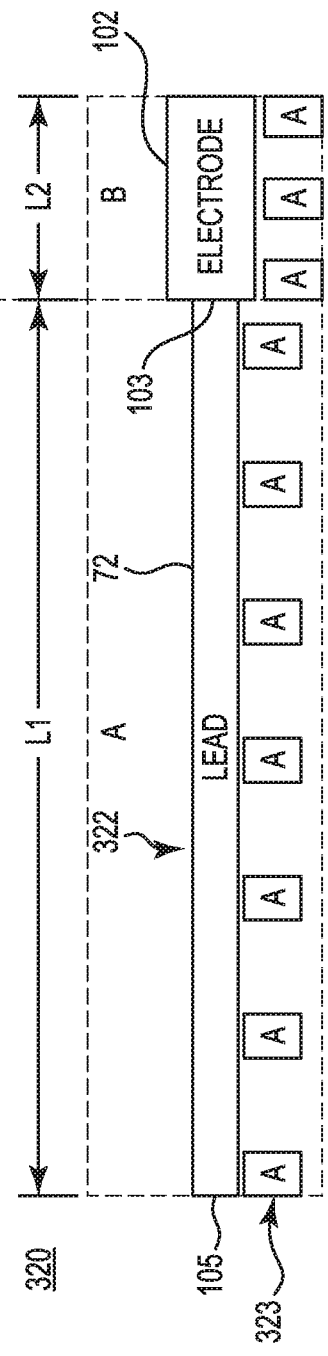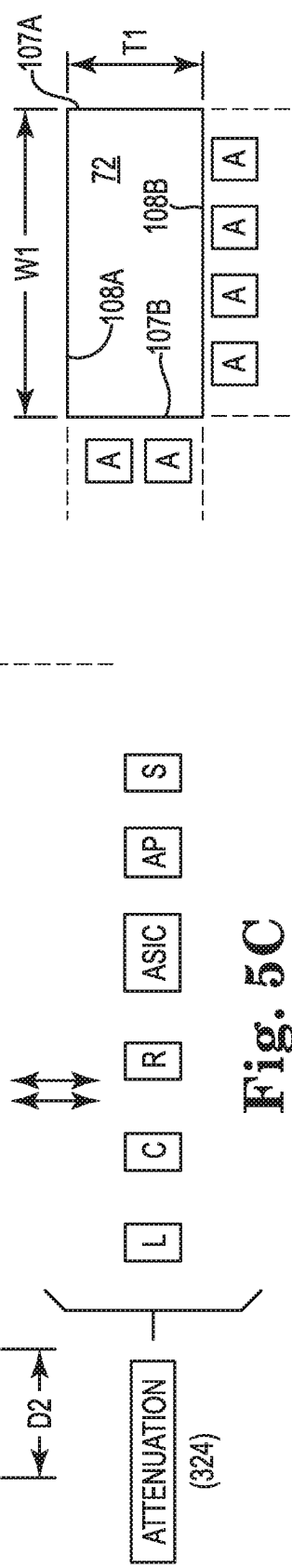

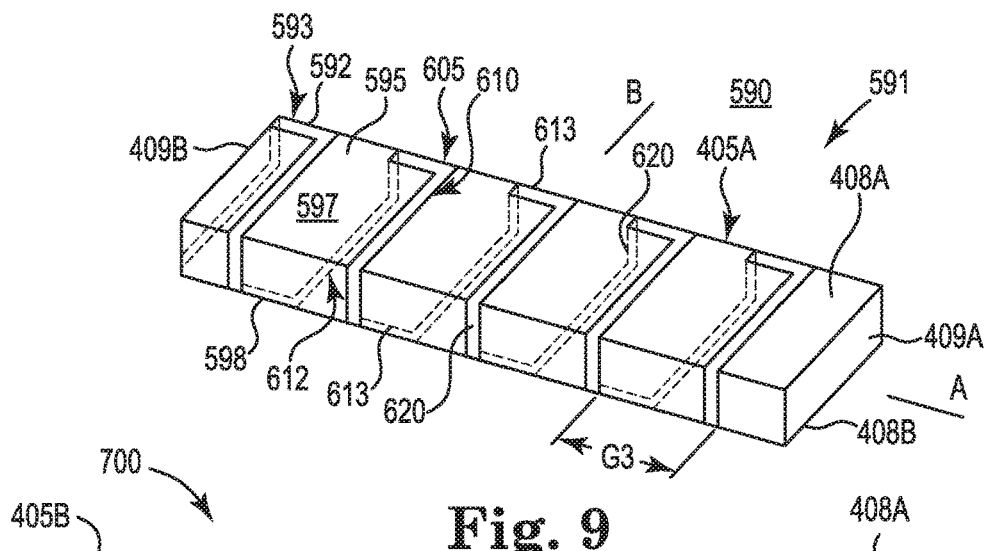
Fig. 9
| | |
|---|---|
| 720A | FIFTH INSULATOR |
| 718A | THIRD SHIELD CONDUCTIVE ELEMENT |
| 520A | THIRD INSULATOR |
| 517A | FIRST SHIELD CONDUCTIVE ELEMENT |
| 518A | FIRST INSULATOR |
| 514A | SIGNAL CONDUCTIVE ELEMENT |
| 510 | BASE INSULATOR |
| 514B | SIGNAL CONDUCTIVE ELEMENT |
| 518B | SECOND INSULATOR |
| 517B | SECOND SHIELD CONDUCTIVE ELEMENT |
| 520B | FOURTH INSULATOR |
| 718B | FOURTH SHIELD CONDUCTIVE ELEMENT |
| 720B | SIXTH INSULATOR |
Fig. 10
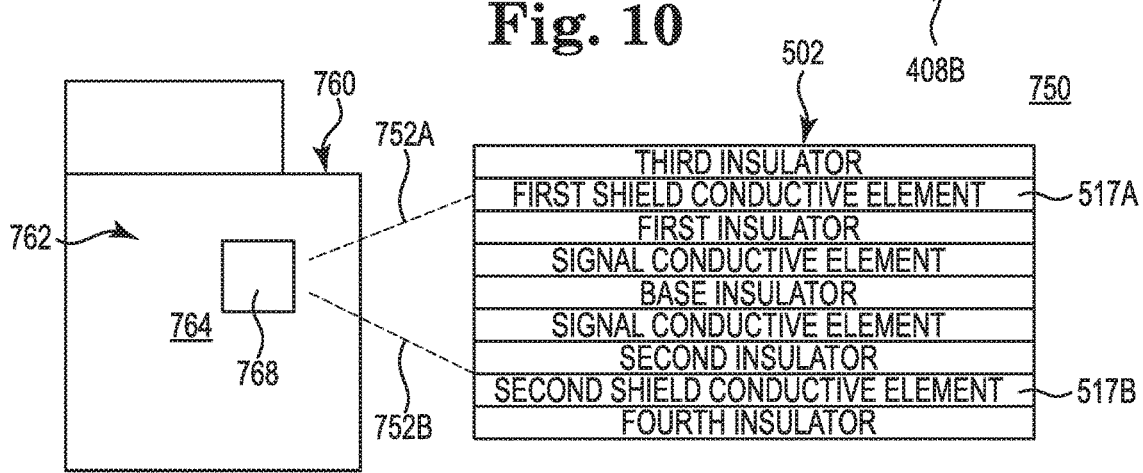
Fig. 11

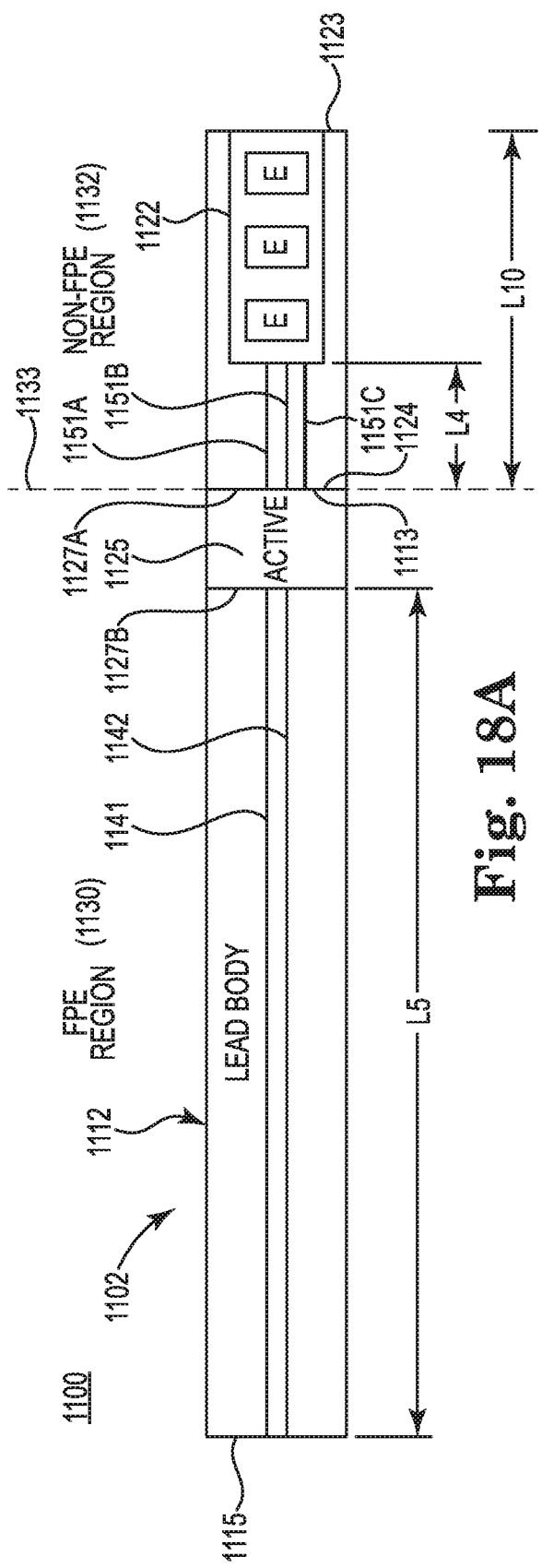
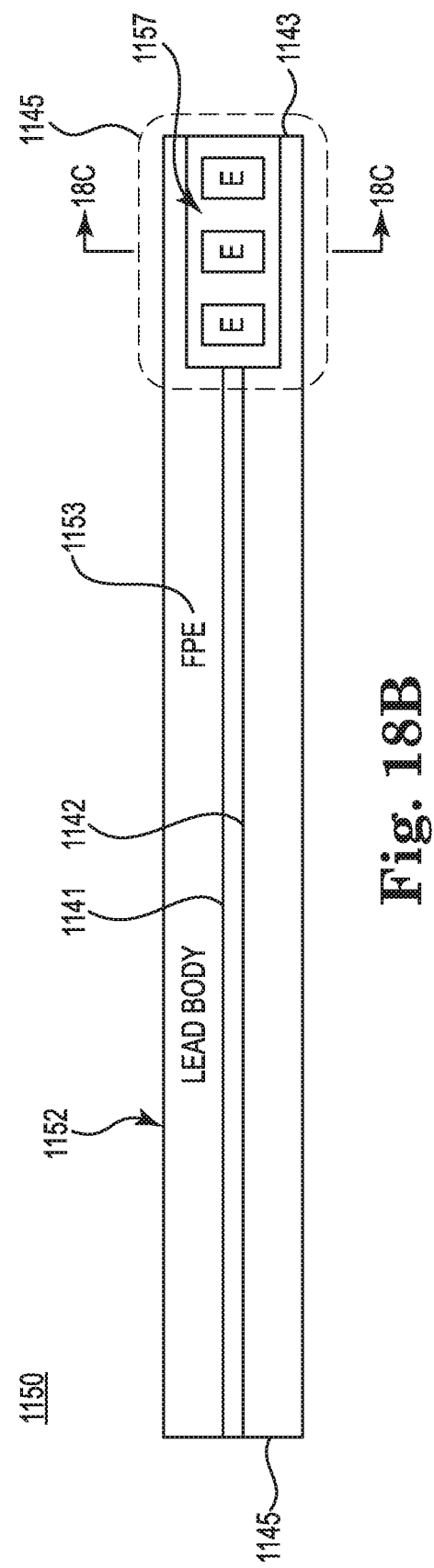
Fig. 18A
Fig. 18B

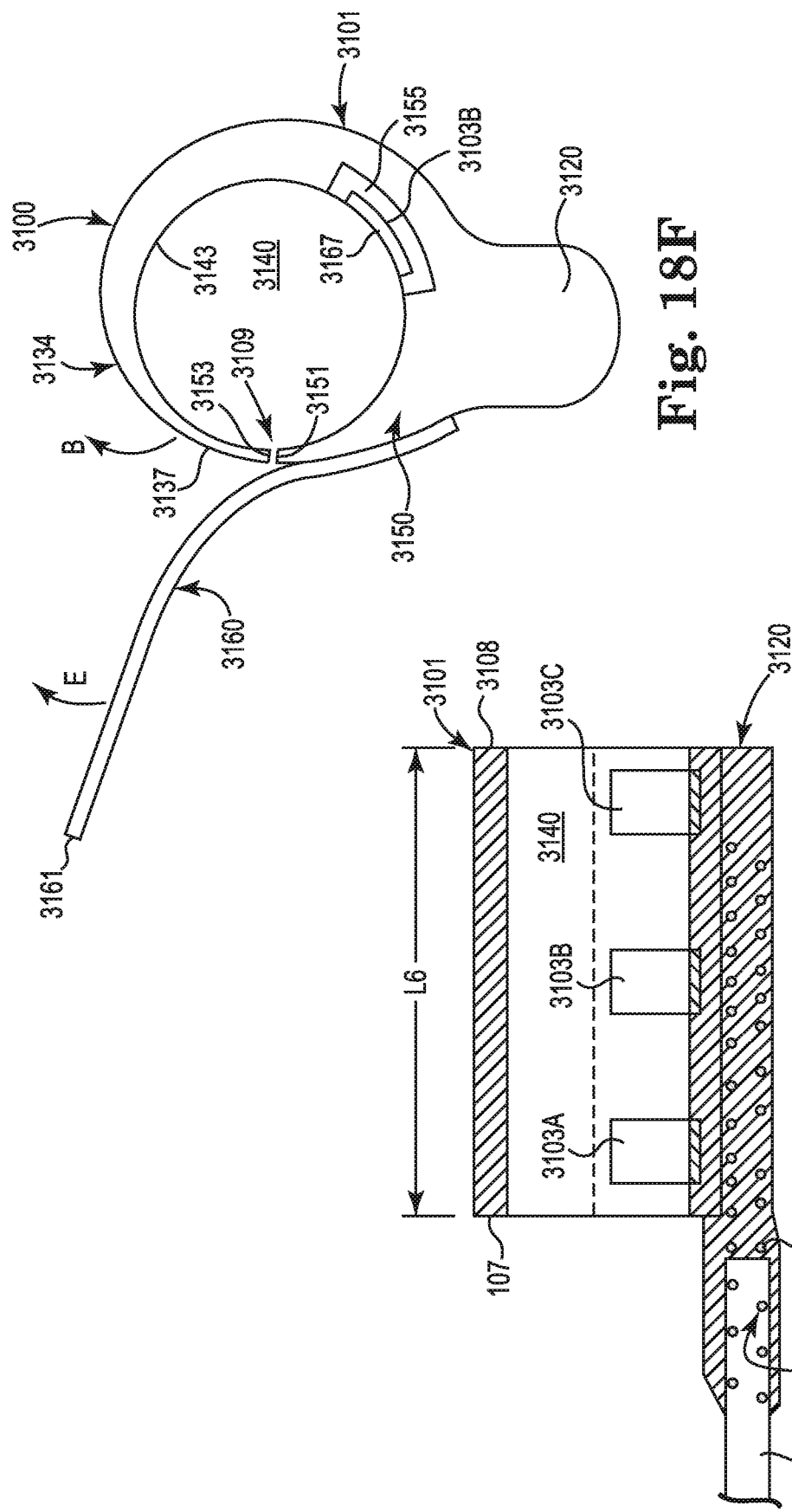

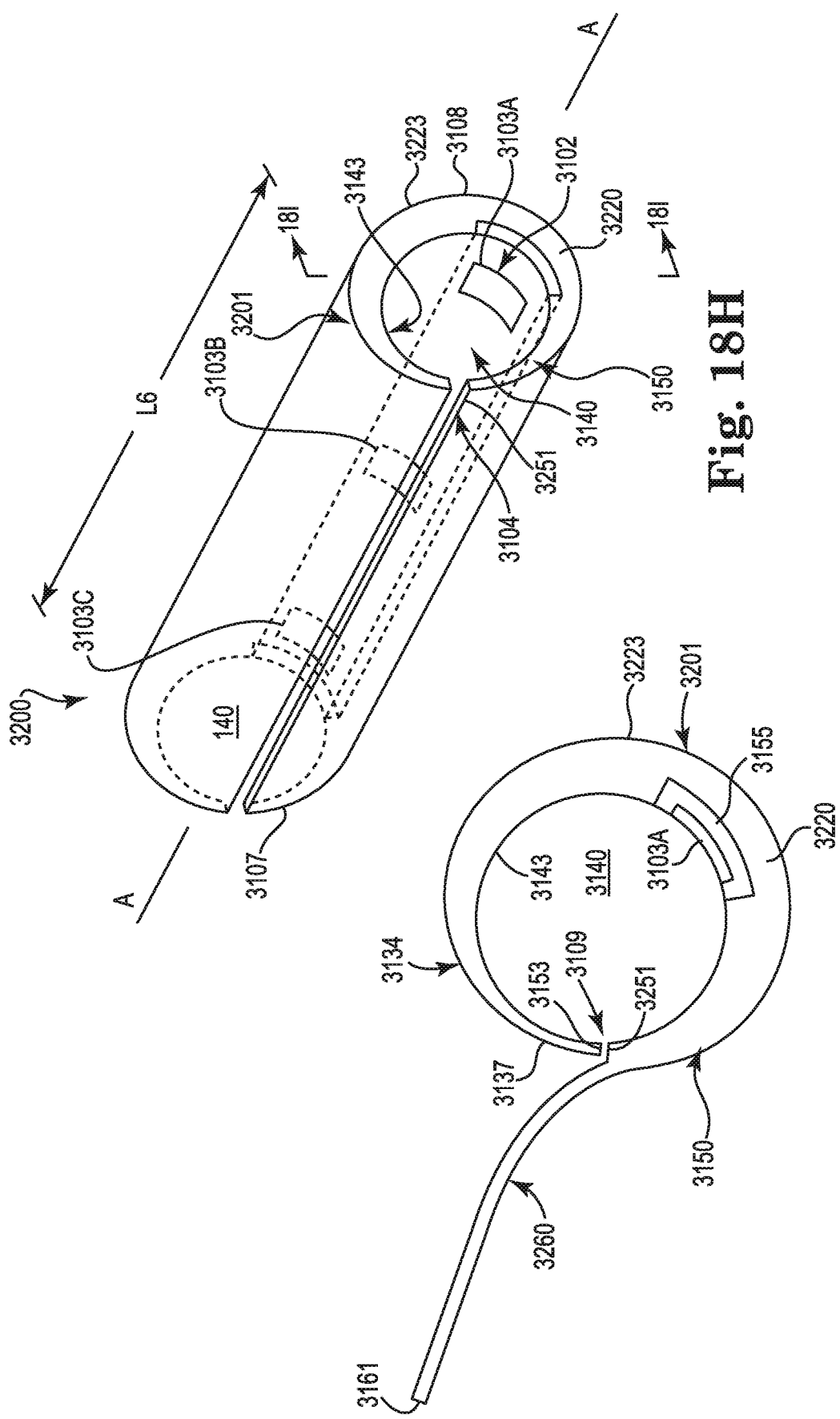

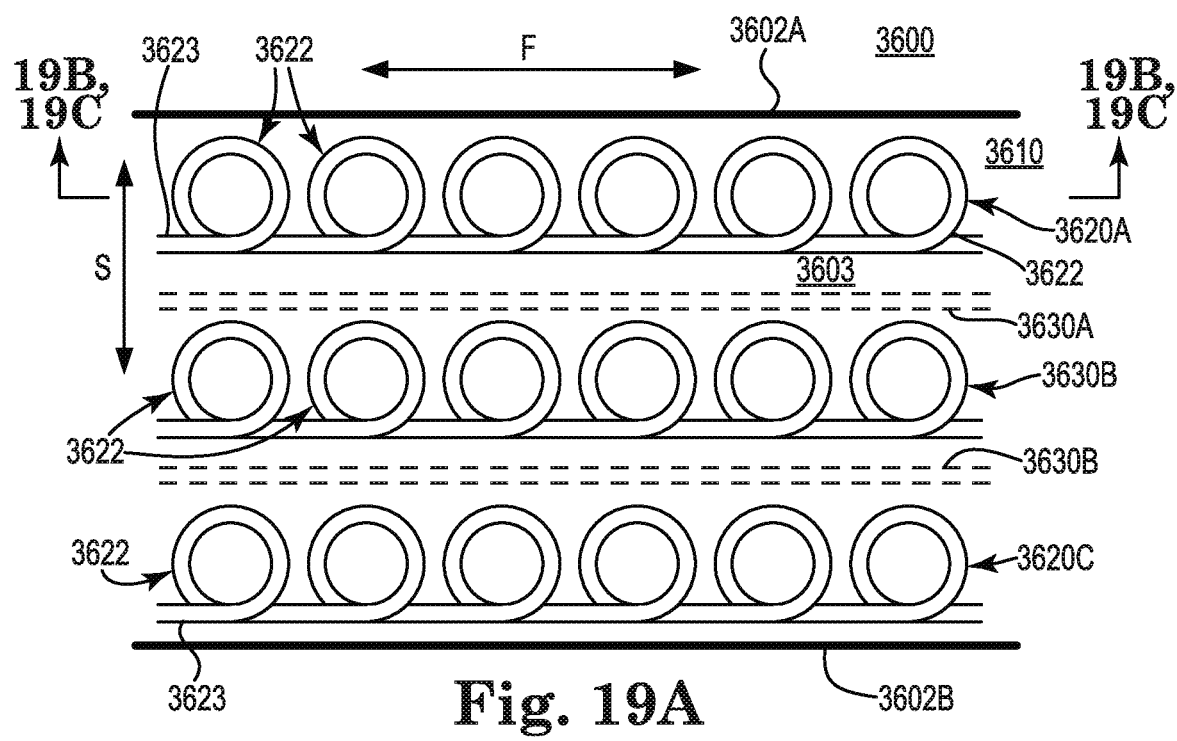
Fig. 19A
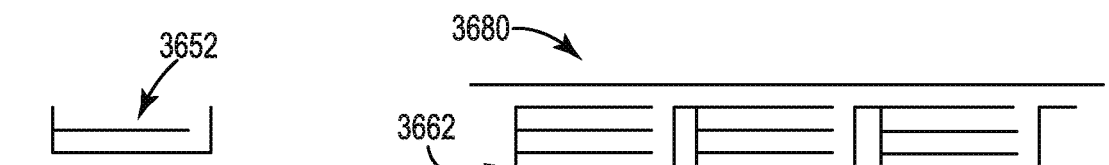
Fig. 19B
Fig. 19C
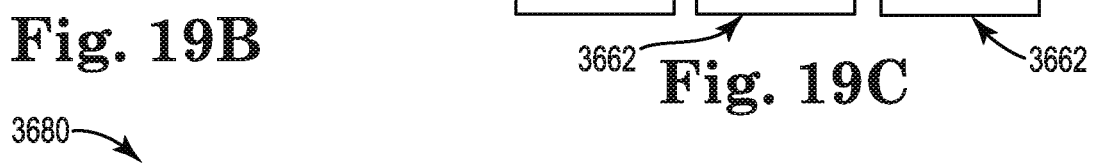
Fig. 19D
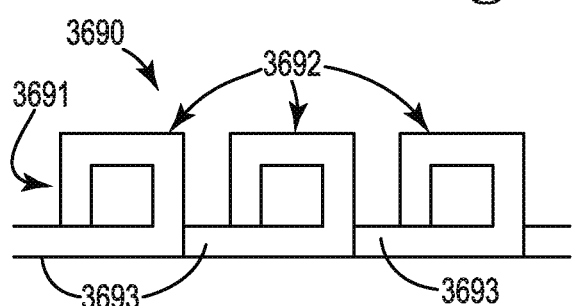
Fig. 19E
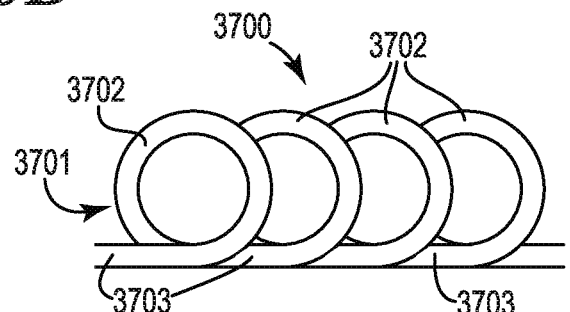
Fig. 19F

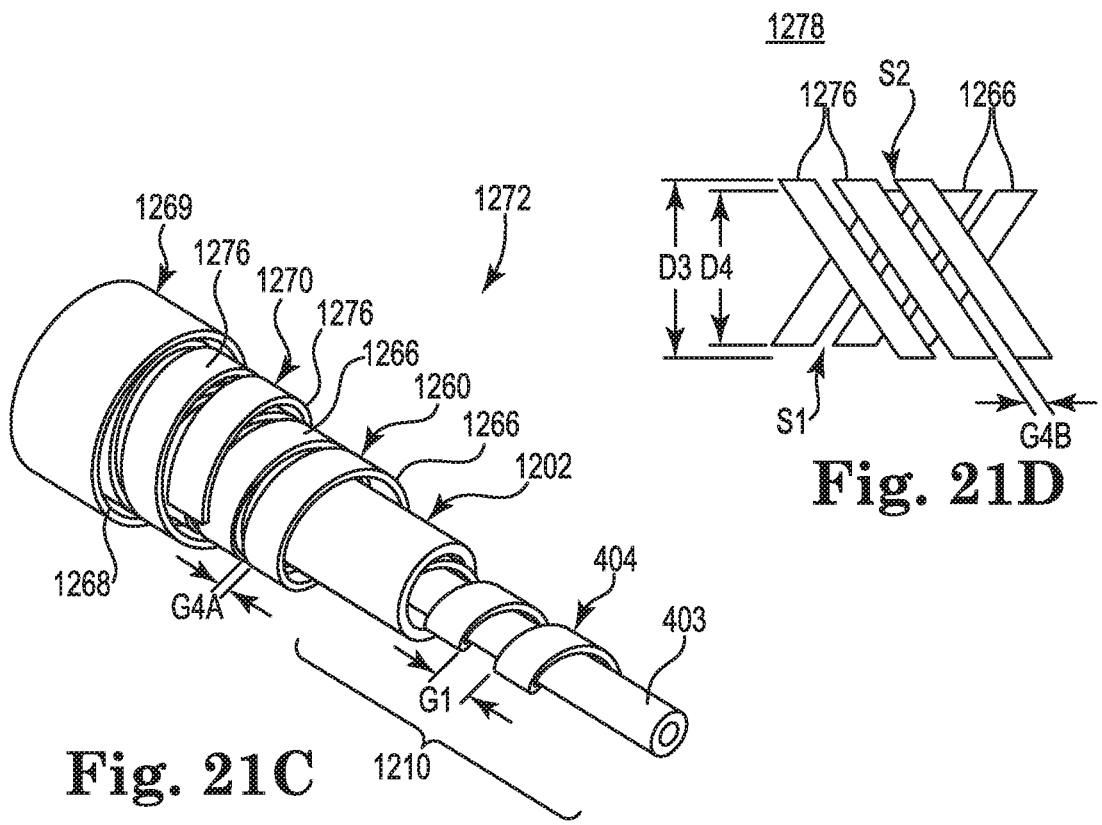
Fig. 21C
Fig. 21D
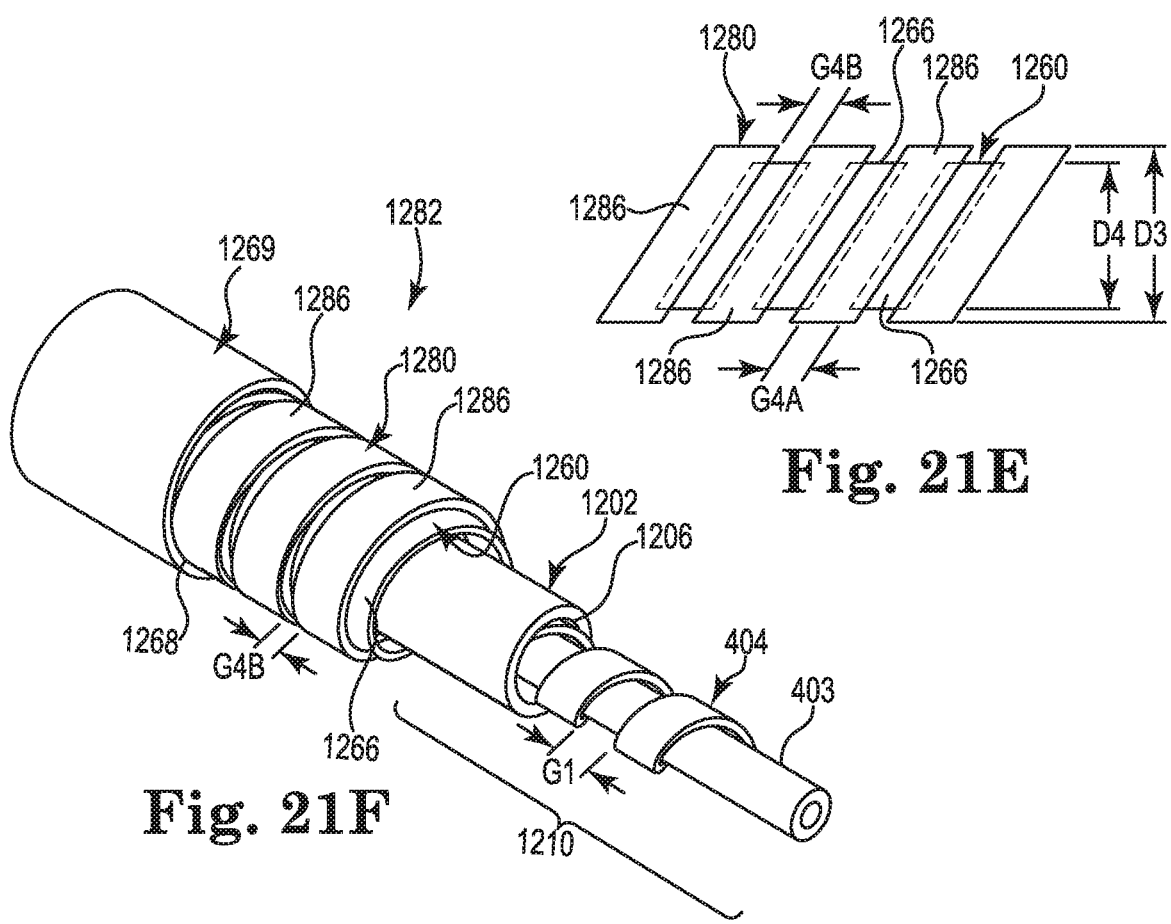
Fig. 21E
Fig. 21F

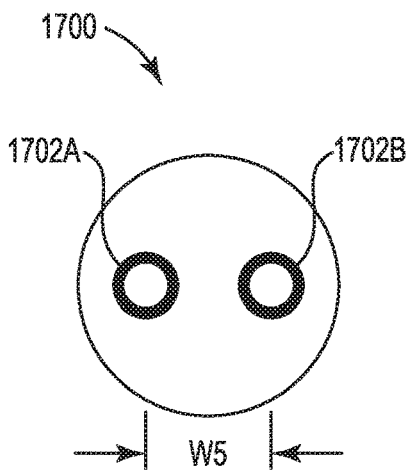
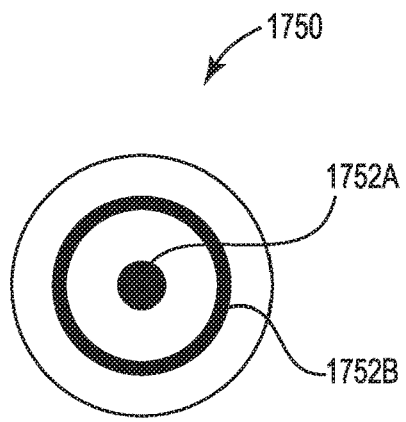
Fig. 29   Fig. 30
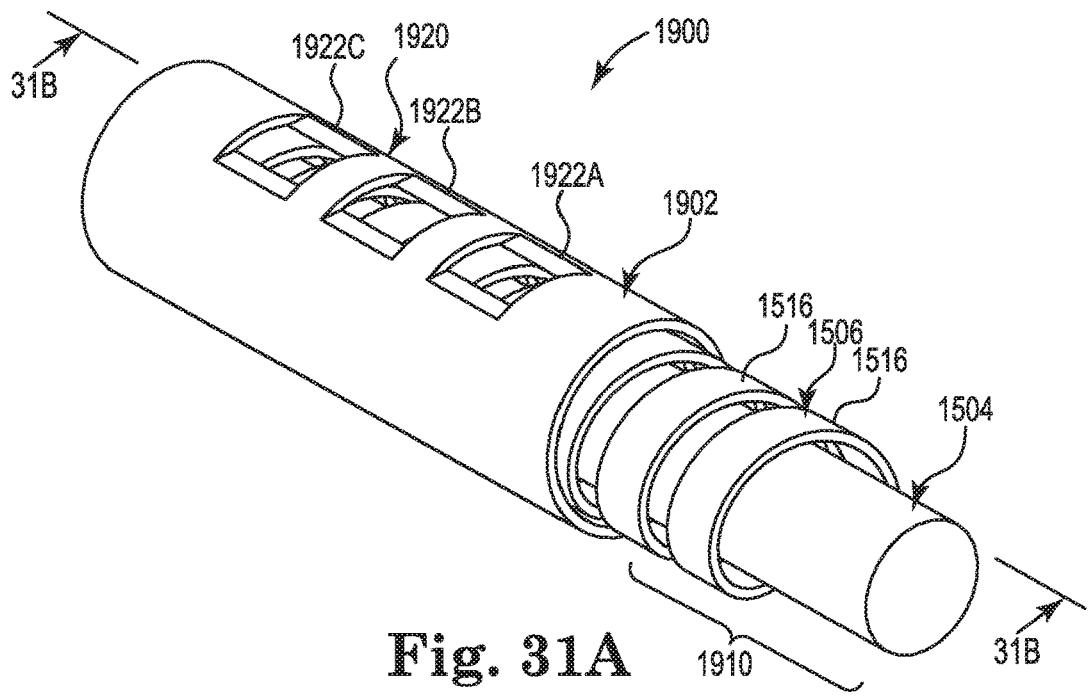
Fig. 31A
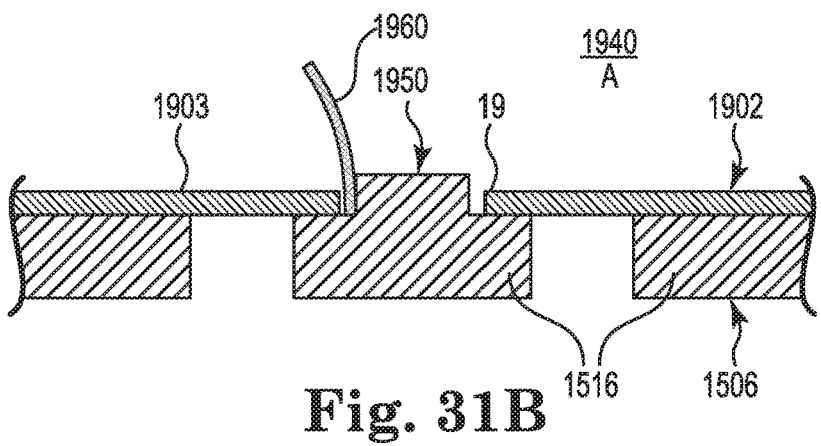
Fig. 31B

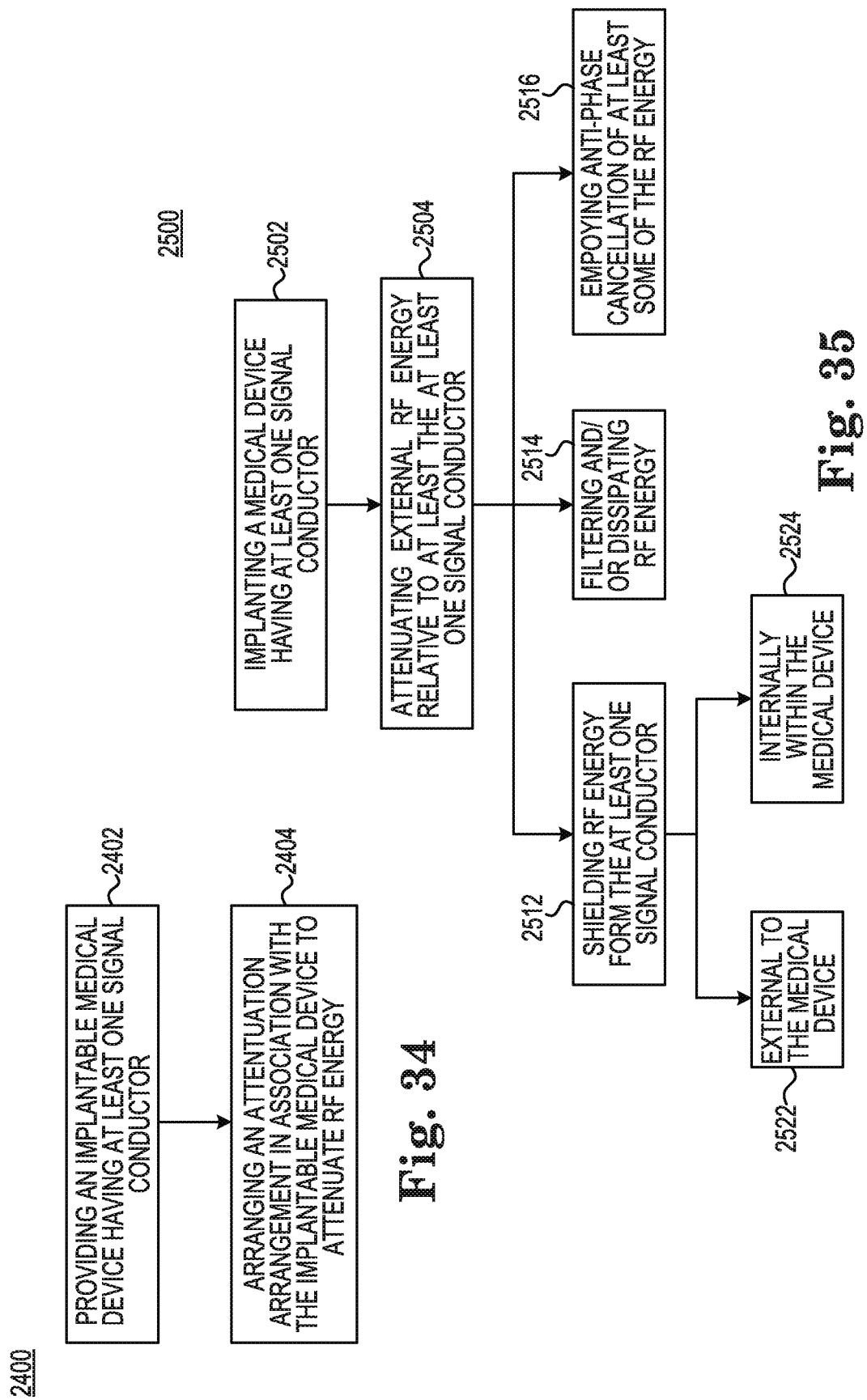

ATTENUATION ARRANGEMENT FOR IMPLANTABLE MEDICAL DEVICE

CROSS-REFERENCE TO RELATED APPLICATIONS

This application is a 371 National Stage Application that claims priority to PCT Application No. PCT/US2017/032107, entitled "ATTENUATION ARRANGEMENT FOR AN IMPLANTABLE MEDICAL DEVICE," having a filing date of May 11, 2017 which claims benefit of Provisional U.S. Patent Application No. 62/334,774, entitled "ATTENUATION ARRANGEMENT FOR AN IMPLANTABLE MEDICAL DEVICE," having a filing date of May 11, 2016, both of which are incorporated herein by reference.

BACKGROUND

Modern medicine has provided previously unimaginable abilities, such as internal imaging. One type of internal imaging includes magnetic resonance imaging. Other modern technologies include implantable medical devices, some types of which may not be compatible with such internal imaging.

BRIEF DESCRIPTION OF THE DRAWINGS

FIG. 5B is a block diagram schematically representing an attenuation arrangement in association with a lead assembly, according to one example of the present disclosure.

FIG. 5C is a block diagram schematically representing an attenuation arrangement in association with a lead assembly, according to one example of the present disclosure.

FIG. 5D is an end sectional view schematically representing an attenuation arrangement in association with the lead assembly, according to one example of the present disclosure.

FIG. 9 is a perspective view schematically representing a portion of a FPE assembly including a conductive element forming a three-dimensional (3D) coil structure relative to an insulator, according to one example of the present disclosure.

FIG. 10 is a sectional view schematically representing a FPE assembly of an implantable lead assembly, according to one example of the present disclosure.

FIG. 11 is diagram including a sectional view schematically representing a FPE assembly of an implantable lead assembly and a block diagram of an implantable pulse generator to which the implantable lead assembly is coupled, according to one example of the present disclosure.

FIG. 18A is a block diagram schematically representing a portion of a lead assembly formed as a FPE assembly and including an associated attenuation arrangement, according to one example of the present disclosure.

FIG. 18B is a block diagram schematically representing a lead assembly formed as a FPE assembly and including an associated attenuation arrangement, according to one example of the present disclosure.

FIG. 18F is a sectional view as taken along lines 18F-18F of FIG. 18E and schematically representing a cuff electrode incorporating a FPE assembly, according to one example of the present disclosure.

FIG. 18G is a sectional view as taken along lines 18G-18G of FIG. 18E and schematically representing a cuff electrode incorporating a FPE assembly, according to one example of the present disclosure.

FIG. 18H is an isometric view schematically representing a cuff electrode incorporating a FPE assembly, according to one example of the present disclosure.

FIG. 18I is a sectional view as taken along lines 18I-18I of FIG. 18H and schematically representing a cuff electrode incorporating a FPE assembly, according to one example of the present disclosure.

FIG. 19A is a view schematically representing arrays of circular-shaped conductive loops in a portion of a lead, according to one example of the present disclosure.

FIG. 19B is a sectional view schematically representing at least one conductive loop, according to one example of the present disclosure.

FIG. 19C is a sectional view schematically representing array of conductive loops, according to one example of the present disclosure.

FIG. 19D is a sectional view schematically representing array of conductive loops and a capacitive structure, according to one example of the present disclosure.

FIG. 19E is a view schematically representing an array of rectangular-shaped conductive loops in a portion of a lead, according to one example of the present disclosure.

FIG. 19F is a view schematically representing an array of overlapping, circular-shaped conductive loops in a portion of a lead, according to one example of the present disclosure.

FIG. 21C is a perspective view schematically representing an implantable lead assembly including a first FPE assembly of FIG. 21B and including an external shield in which a third FPE assembly has helical windings in an opposite orientation relative to the helical windings of the second FPE assembly, according to one example of the present disclosure.

FIG. 21D is partial top plan view schematically representing the opposite orientation of the helical windings of the respective second and third FPE assemblies, according to one example of the present disclosure.

FIG. 21E is a perspective view schematically representing an implantable lead assembly including a first FPE assembly of FIG. 21B and including an external shield in which a third FPE assembly has helical windings in generally the same orientation relative to the helical windings of a second FPE assembly, according to one example of the present disclosure.

FIG. 21F is partial top plan view schematically representing the generally same orientation of the helical windings of the respective second and third FPE assemblies, according to one example of the present disclosure.

FIG. 29 is a sectional view schematically representing two signal conductive elements arranged side-by-side within a body of a lead, according to one example of the present disclosure.

FIG. 30 is a sectional view schematically representing one example implementation of a coaxial configuration of a pair of signal conductive elements within a body of a lead, according to one example of the present disclosure.

FIG. 31A is a perspective view schematically representing an implantable lead assembly including the lead assembly of FIG. 25 and further including an outer flexible tubular insulator having windows, according to one example of the present disclosure.

FIG. 31B is a sectional view as taken along lines 31B-31B of FIG. 31A and schematically representing a conductive protrusion relative to a window of the outer flexible tubular insulator, according to one example of the present disclosure.

FIG. 34 is a flow diagram schematically representing a method involving an attenuation arrangement, according to one example of the present disclosure.

FIG. 35 is a flow diagram schematically representing a method involving an attenuation arrangement, according to one example of the present disclosure.

DETAILED DESCRIPTION

In the following detailed description, reference is made to the accompanying drawings which form a part hereof, and in which is shown by way of illustration specific examples in which the disclosure may be practiced. It is to be understood that other examples may be utilized and structural or logical changes may be made without departing from the scope of the present disclosure. The following detailed description, therefore, is not to be taken in a limiting sense. It is to be understood that features of the various examples described herein may be combined, in part or whole, with each other, unless specifically noted otherwise.

In at least some examples, an implantable medical device includes at least one conductive element and an associated attenuation arrangement to attenuate radiofrequency (RF) energy relative to at least the at least one conductive element. In some examples, the RF energy comprises magnetic resonance imaging (MRI) energy.

In some examples, in a first aspect, the attenuation arrangement can dissipate RF energy in the proximity of the at least one conductive element, such as but not limited to, conductors within a lead of a lead assembly.

In some examples, in a second aspect, the attenuation arrangement may reduce coupling of RF energy onto the at least one conductive element (e.g. lead conductors). In one aspect, such reduced coupling may reduce RF power dissipated into tissue at contact electrodes (connected to the at least one conductive element) such that energy dissipated to surrounding tissues via the contact electrodes may be reduced to a known safe level.

In some examples, the first aspect and the second aspect can be pursued independently while in some examples, the first and second aspects are pursued together.

It will be understood that in some examples, attenuating RF energy may involve aspects in addition to, instead of, and/or in cooperation with the above-mentioned first and second aspects.

Via the attenuation arrangement in at least some examples of the present disclosure, an implantable medical device can be constructed in a manner which may reduce the number of components, which may simplify manufacturing operations, and which may increase the ability to reliably control target design parameters. Such target design parameters include, but are not limited to, capacitive coupling between conductors, the body, and other elements.

These examples, and additional examples, are described in association with at least FIGS. 1-35.

Figure 1:
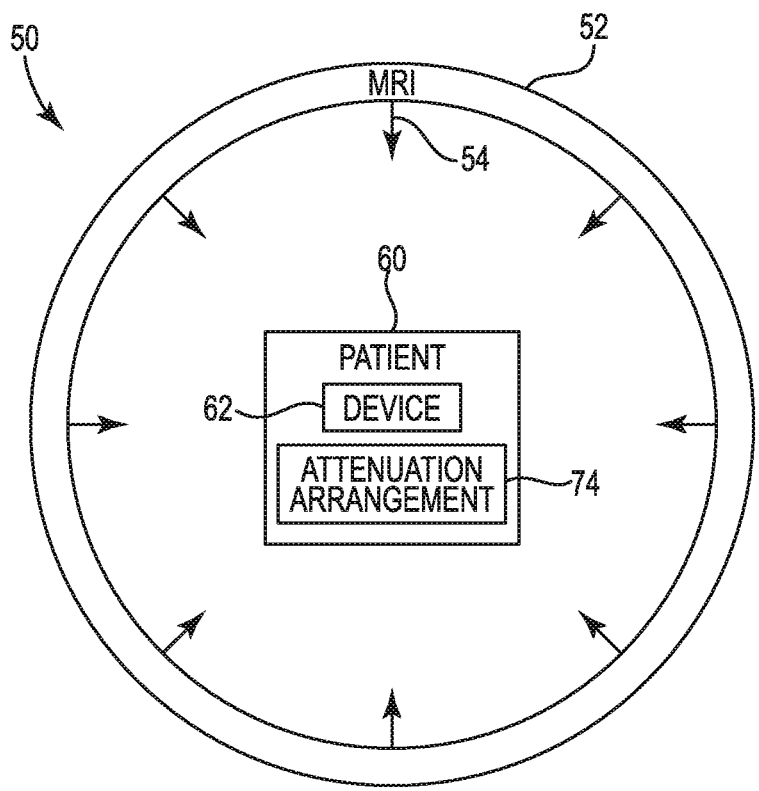
FIG. 1 is a diagram including an end view schematically representing a patient within an MRI field, according to one example of the present disclosure.

FIG. 1 is a diagram including an end view schematically representing a patient within an MRI field, according to one example of the present disclosure. As shown in FIG. 1, a patient environment 50 includes an MRI device 52 which produces an MRI field 54 for scanning a patient 60 to obtain internal images. Implanted within the patient 60 is an implantable medical device (IMD) 62. In some examples, the IMD 62 comprises at least one conductive element suitable for conducting electricity for informational, diagnostic, and/or therapeutic purposes.

An attenuation arrangement 74 is associated with the IMD 62 to attenuate energy from the MRI field 54 relative to the IMD 62. Via the attenuation arrangement, the IMD 62 may be deemed to be MRI-compatible or an MRI-conditional device such that a patient having an IMD 62 may be permitted to receive an MRI scan instead of being excluded from such MRI scanning. More specific aspects of the attenuation arrangement 74 are further described in association with at least FIGS. 2 and 5A, and throughout examples of the present disclosure.

It will be understood that in some examples, the MRI device 52 is considered representative of other types of imaging, diagnostic, or interventional devices which produce radiofrequency fields or electromagnetic fields for which the attenuation arrangement 74 can act to attenuate energy from those devices relative to the IMD 62.

In some examples, the IMD 62 forms part of a system having at least some components implanted with patient 60 with such components including, but not limited to, the IMD 62. Moreover, it will be understood that in some examples the IMD 62 comprises a singular component while in some examples, the IMD 62 comprises at least two components which are separate but which are physically and/or electrically coupled together, either directly or indirectly.

Figure 2:
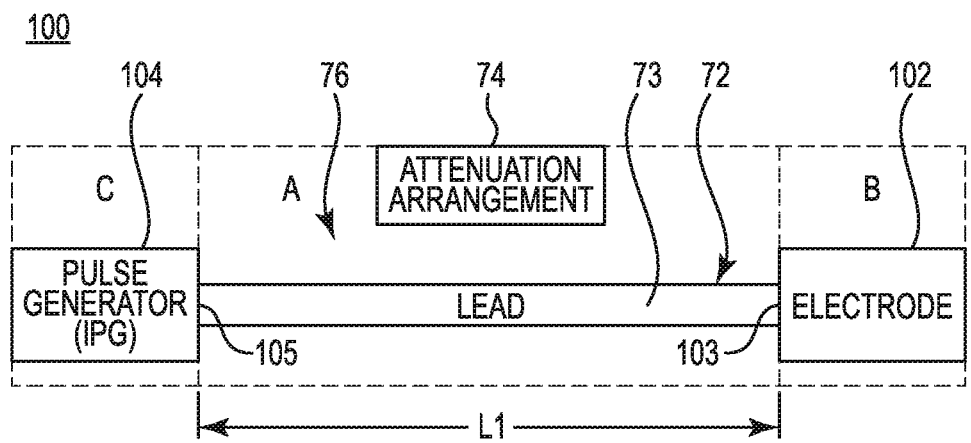
FIG. 2 is a block diagram including a side view schematically representing an implantable stimulation system including an associated attenuation arrangement, according to one example of the present disclosure.
Figure 3:
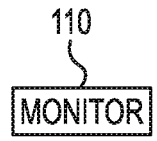
FIG. 3 is a block diagram schematically representing a block diagram of a monitor, according to one example of the present disclosure.

FIG. 2 is a block diagram 100 schematically representing one IMD 62 implemented as implantable system 76, according to one example of the present disclosure. As shown in FIG. 2, in some examples system 76 includes lead 72 interposed between electrode 102 and a pulse generator 104. The lead 72 has a first end 103 coupled relative to electrode 102 and an opposite second end 105 coupled relative to pulse generator 104. In some examples, such coupling includes both a mechanical connection and an electrical connection.

As further shown in FIG. 2, the attenuation arrangement 74 is associated with at least lead 72, as represented by zone A. In some examples, the attenuation arrangement 74 is further associated with electrode 102 (as represented by zone B) and/or further associated with pulse generator 104, as represented by zone C shown in FIG. 2.

In some examples, the attenuation arrangement 74 is coextensive with at least electrode 102. In one such example, as described later in association with at least FIG. 18B, at least a portion of the attenuation arrangement is embodied in a flexible printed electronic (FPE) assembly which is coextensive with at least the electrode 102. In some examples, a portion of the attenuation arrangement is separate from, and independent of, the FPE assembly. Via such arrangements, attenuation can be provided for electrode 102 which may be in direct contact with body tissues (e.g. a nerve or muscle), such as might occur for a neurostimulation lead for cardiac tissues, cranial tissues, nerves for treating sleep disordered breathing (SDB) such as obstructive sleep apnea. The attenuation arrangement 74 may minimize unwanted RF power deposition and heating of the electrode 102 thereby may prevent tissue damage that might otherwise occur in the absence of minimizing such heat via the attenuation arrangement 74.

In some examples, the attenuation arrangement 74 provides protection for some types of electrodes 102 which do not have stimulation as their primary function or which do not perform any stimulation. For instance, some electrodes 102 are used primarily for or exclusively for sensing. Accordingly, in some examples, the attenuation arrangement 74 may protect the sensing electrode 102 from potential damage or interference from the MRI-energy/field. This protective functionality also may be implemented when the sensing electrode 102 includes some form of circuitry beyond a mere conductive element, such as when a simple conductive element (defining electrode 102) is replaced with an accelerometer-based sensor, pressure sensor, etc.

In some examples, attenuation arrangement 74 is associated exclusively with lead 72, and not associated with electrode 102 and/or pulse generator 104.

In some examples, other configurations can be employed. For instances, in some examples attenuation arrangement 74 is associated exclusively with electrode 102 and not with lead 72 while in some examples, attenuation arrangement 74 is associated exclusively with pulse generator 104.

In other instances, attenuation arrangement 74 is associated with electrode 102 and pulse generator 104 but not with lead 72, such as when wireless communication and coupling exists between electrode 102 and pulse generator 104.

It will be further understood that in some examples, one of the components (72, 102, 104) of system 76 can be external to the patient's body, and therefore may be operatively decoupled from the implanted components of the system 76 such that the attenuation arrangement 74 is not employed for those external components of system 76.

In some examples, electrode 102 can function as a stimulation electrode and/or a sensor electrode 102. In some examples, system 76 includes multiple such electrodes 102. In some instances of having multiple electrodes, some electrodes 102 are dedicated to sensing while some electrodes are dedicated to stimulation.

In some examples, system 76 includes a dedicated sensor monitor 110 (FIG. 3) in place of pulse generator 104 or in addition to pulse generator 104, such that the attenuation arrangement 74 is associated with sensor monitor 110. It will be understood that pulse generator 104 can include sensor monitor functionality even in the absence of a separate, dedicated sensor monitor 110.

In some examples, monitor 110 can automatically sense or detect a MR signal and in response, may cause IPG 104 to transition into a special protection mode.

In some examples, additional electrodes 102 may be positioned along a length of lead 72.

In some examples, lead 72 is flexible yet is equipped to have sufficient pushability, steerability, torquability, flex resistance, etc. to be advanced and maneuvered within and through a patient's body via subcutaneous tunneling, transvenous delivery, and/or percutaneous access.

In some examples, lead 72 comprises an assembly of multiple components and accordingly may sometimes be referred to as a lead assembly 73. Moreover, as described later throughout the present disclosure, in some examples, at least some portions of such a lead assembly 73 may be implemented as a flexible printed electronic (FPE) assembly.

In some examples, forming at least a portion of the lead and/or other components (e.g. IPG 104, electrode(s) 102) via the FPE assembly may provide the ability to control the structure of the lead (and/or other components) and any associated attenuation arrangements more finely, more precisely, at a lower cost, and/or in a smaller package than non-FPE-based lead construction. Moreover, in some examples, constructing leads (and/or other components) with associated attenuation arrangements may enable increasing a density of a number and/or type of conductive features within a given volume within an implantable medical device, such as a lead. In some examples, a lead (and/or other components) constructed via a FPE assembly may have a cross-sectional area at least one order of magnitude less than a cross-sectional area of a non-FPE-based lead. In some examples, a lead (and/or other components) constructed via a FPE assembly may enable achieving the desired functionality while utilizing a volume of conductive material which is at least one order of magnitude less than a volume of conductive material used in non-FPE construction.

In some examples, the lead 72 and pulse generator 104 may be permanently coupled together, i.e. combined to act as a single component. In some examples, this single component also may comprise at least one electrode 102 coupled to the lead 72. In some examples, the combined lead 72 (and electrode(s) 102) and pulse generator 104 are embodied as a micro-element in which at least both the lead 72 and pulse generator 104 are sized to be implanted within a single region of the body, such as a head-and-neck region. In some such examples, the combined lead 72 (with electrode(s) 102) and pulse generator 104 are sized for percutaneous implantation at a single site and/or are sized for transvenous implantation.

In some such examples, the permanently coupled IPG 104 and lead 72 may be wholly or partially constructed via at least some aspects of an FPE assembly according to at least some of the examples described in association with FIGS. 1-35 throughout the present disclosure.

In some examples, portions of an implantable medical device 62, such as system 76, which may be exposed to contact with bodily tissues and/or fluids, are made of biocompatible material and/or coated with a biocompatible material. In some examples, the biomaterial comprises a platinum/iridium material or a platinum black-based material. For instance, electrode 102 and/or an external surface of IPG 104 may include at least some portions made of such biocompatible materials and/or coating.

In some examples, at least some portions of an implantable medical device 62 (e.g. system 76) and/or attenuation arrangement 74 are made from a flexible printed electronics (FPE) assembly, as further described below and throughout examples of the present disclosure. In some such examples, the exposed electrically conductive portions of such a FPE assembly and/or of attenuation arrangement 74 (e.g. those portions exposed to bodily tissues/fluids) also may be at least partially formed from and/or coated with a biocompatible material such as, but not limited to, platinum/iridium material or a platinum black-based material.

Figure 4:
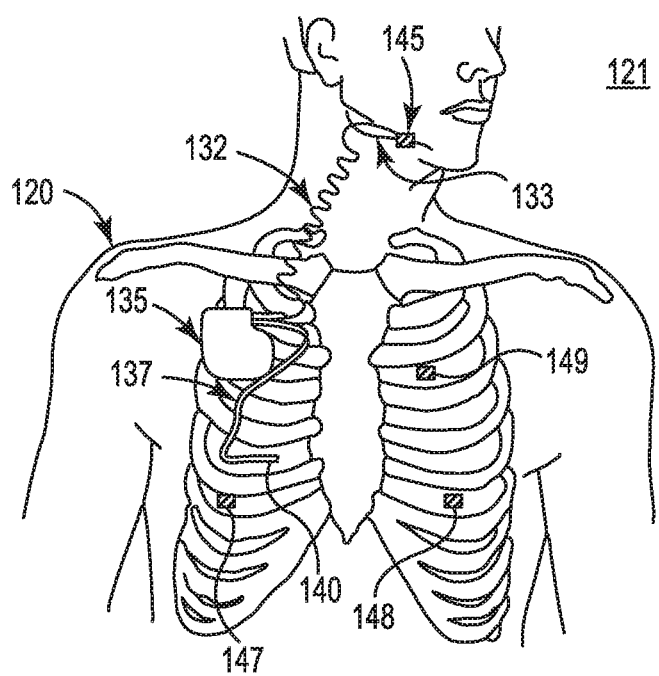
FIG. 4 is a diagram schematically representing an implantable stimulation system as deployed within a patient, according to one example of the present disclosure.

FIG. 4 is a diagram schematically representing a stimulation system 121 as deployed within a patient, according to one example of the present disclosure. As illustrated in FIG. 4, in some examples system 121 comprises an implantable pulse generator (IPG) 135, capable of being surgically positioned within a pectoral region of a patient 120, and a stimulation lead 132 electrically coupled with the IPG 135. In some examples, pulse generator 135 comprises at least some of substantially the same features and attributes as the pulse generator 104, as previously described in association with at least FIG. 2A and the various examples described throughout the present disclosure.

In some examples, at least some or all of the components of the implantable system 121 are considered to be an implantable medical device (IMD) 62 in FIG. 1.

As further shown in FIG. 4, the lead 132 includes a stimulation element 145 (e.g. electrode portion, such a cuff electrode) and extends from the IPG 135 so that the stimulation element 145 is positioned in contact with a desired nerve 133 to stimulate nerve 133 for restoring upper airway patency. In some examples, the desired nerve comprises a hypoglossal nerve. In some examples, stimulation element 145 comprises at least some of substantially the same features and attributes as the electrode 102, as previously described in association with at least FIG. 2, and the various examples described throughout the present disclosure.

One implantable stimulation system in which lead 132 may be utilized, for example, is described in U.S. Pat. No. 6,572,543 to Christopherson et al., and which is incorporated herein by reference in its entirety. In one example, device 121 comprises at least one sensor portion 140 (electrically coupled to the IPG 135 and extending from the IPG 135 via lead 137) positioned in the patient 120.

In some examples, sensor portion 140 provides one implementation of a lead having a sensor electrode as described in association with at least FIG. 2, and the various examples described throughout the present disclosure. As previously noted, in some such examples the attenuation arrangement is co-extensive with at least sensor portion 140, such as defined for zone A in FIG. 2.

In some examples, sensor portion 140 senses respiratory effort, such as via sensing respiratory pressure.

In some examples, the sensor portion 140 detects respiratory effort including respiratory patterns (e.g., inspiration, expiration, respiratory pause, etc.). In some examples, this respiratory information is employed to trigger activation of stimulation element 145 to stimulate a target nerve 133. Accordingly, in some examples, the IPG 135 receives sensor waveforms (e.g. one form of respiratory information) from the respiratory sensor portion 140, thereby enabling the IPG 135 to deliver electrical stimulation according to a therapeutic treatment regimen in accordance with examples of the present disclosure. In some examples, the respiratory information is used to apply the stimulation synchronously with inspiration or synchronized relative to another aspect of the respiratory cycle. In some examples, the respiratory sensor portion 140 is powered by the IPG 135.

In some such examples, sensor portion 140, including electrode 102 comprises an accelerometer.

In some examples, the sensor portion 140 comprises a pressure sensor. In one example, the pressure sensor in this example detects pressure in the thorax of the patient. In other examples, the sensed pressure can be a combination of thoracic pressure and cardiac pressure (e.g., blood flow). With this configuration, a controller associated with IPG 135 is configured to analyze this pressure sensing information to detect the respiratory patterns of the patient.

In some examples, the pressure sensor detects differential pressure.

In some other examples, the sensor portion represented via reference numeral 140 comprises a bio-impedance sensor or an array of bio-impedance sensors and can be located in regions other than the pectoral region. In one aspect, such an impedance sensor is configured to sense a bio-impedance signal or pattern whereby the control unit evaluates respiratory patterns within the bio-impedance signal. For bio-impedance sensing, in some examples electric current will be injected through an electrode portion within the body and an electrically conductive portion of a housing (i.e. case, can, etc.) of the IPG 135, with the voltage being sensed between two spaced apart stimulation electrode portions (such as stimulation element 145). In some examples, the voltage is sensed between one of the stimulation electrode portions and the electrically conductive portion of the case of IPG 135 to compute the impedance.

In some examples, system 121 comprises other sensors (instead of sensor portion 140) or additional sensors (in addition to sensor portion 140) to obtain physiologic data associated with respiratory functions and/or other physiologic functions. For instance, as shown in FIG. 4, in some examples system 121 may include various electrode portions 147, 148, 149 distributed about the chest area for measuring a trans-thoracic bio-impedance signal, an electrocardiogram (ECG) signal, or other respiratory-associated signals, other cardiac signals, etc.

In some examples, the various electrode portions 147, 148, 149 or even a single lead is used to measure trans-thoracic electrical bio-impedance. This measurement also can be used in combination with other parameters (e.g. cardiac, pulmonary, etc.) to determine respiratory effort and/or related health information.

In some examples, system 121 utilizes at least one accelerometer to obtain and provide sensing information regarding respiration and/or other conditions related to treating and/or evaluation sleep disordered breathing, such as obstructive sleep apnea.

In some such examples, the at least one accelerometer is incorporated into sensor portion 140 at the distal portion of sensing lead 137.

In some such examples, instead of having at least one accelerometer as part of sensor portion 140, an at least one accelerometer is directly coupled relative to the IPG 135. The accelerometer can be incorporated internally within a housing of the IPG 135 or can be affixed to an external portion of the IPG 135 in some fashion and electrically and communicatively coupled to circuitry within IPG 135.

In some examples, the system 121 can have at least one accelerometer as at least part of the distally-located sensor portion 140 and at least one accelerometer coupled to the IPG 135 in the manner noted above.

As in the other examples, in any of these sensing arrangements, an attenuation arrangement is provided to attenuate MRI-energy relative to such sensors whether they are in a single or multiple different locations. The attenuation arrangement may comprises a single type of attenuation or at least two types of attenuation. In some instances, one type of attenuation is deployed at one location (e.g. sensor portion 140) and a second different type of attenuation is deployed at a second location (e.g. IPG 135), such as when sensor portion 140 extends from lead 137. In some examples, both types of attenuation are deployed at both locations.

In some examples, the sensing and stimulation system for treating sleep disordered breathing (such as but not limited to obstructive sleep apnea) is a totally implantable system which provides therapeutic solutions for patients diagnosed with obstructive sleep apnea. In other examples, one or more components of the system are not implanted in a body of the patient. A few non-limiting examples of such non-implanted components include external sensors (respiration, impedance, etc.), an external processing unit, and/or an external power source. Of course, it is further understood that, in some examples, the implanted portion(s) of the system provides a communication pathway to enable transmission of data and/or controls signals both to and from the implanted portions of the system relative to the external portions of the system. The communication pathway includes a radiofrequency (RF) telemetry link or other wireless communication protocols.

Whether partially implantable or totally implantable, in some examples the system is designed to stimulate an upper-airway-patency-related nerve during some portion of the repeating respiratory cycle to thereby prevent obstructions or occlusions in the upper airway during sleep.

It will be understood that the implantable system 121 provides just one example of an IMD 62 for which an attenuation arrangement 74 attenuates MRI energy, and that many other types of implantable systems for different informational, diagnostic, and/or therapeutic purposes are suitable for deployment with an associated attenuation arrangement 74 of the examples of the present disclosure.

Figure 5A:
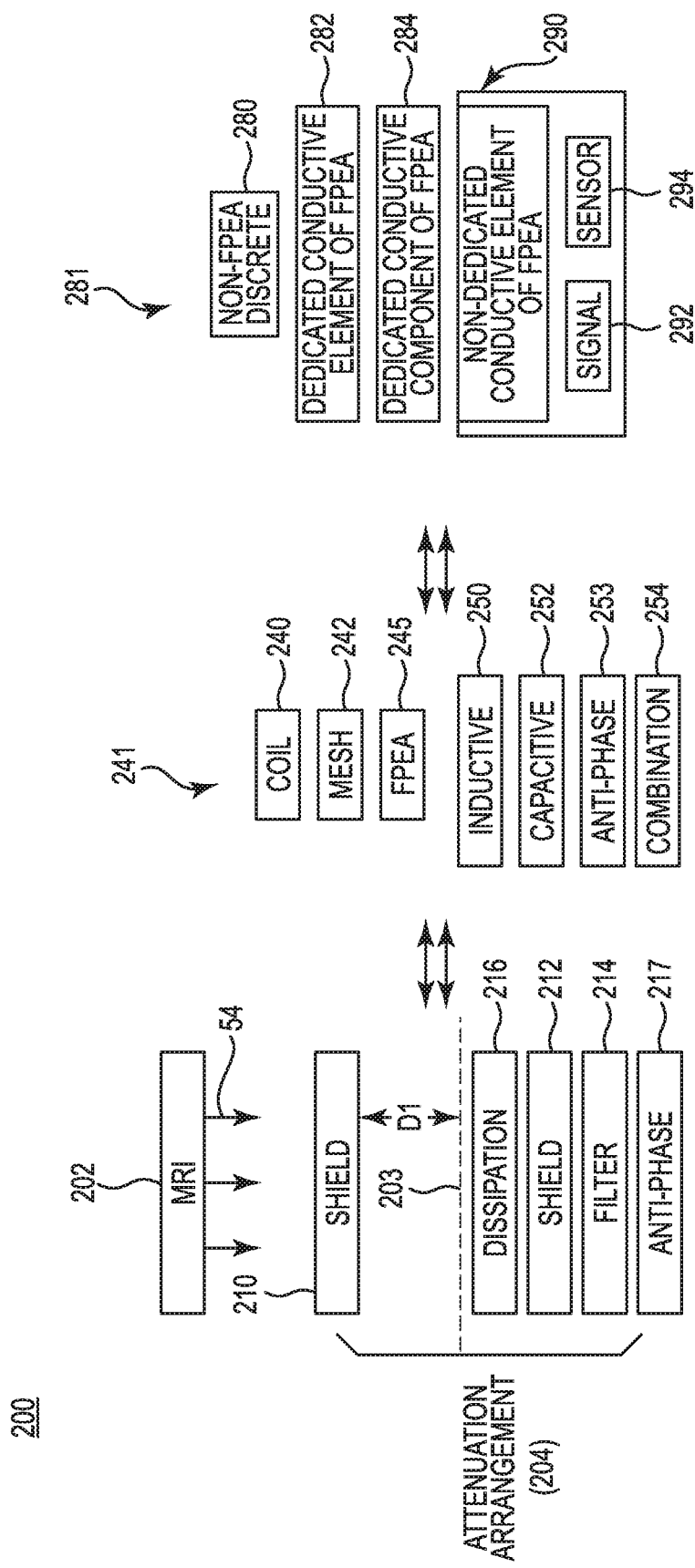
FIG. 5A is a block diagram schematically representing an attenuation arrangement relative to an MRI-energy field, according to one example of the present disclosure.

FIG. 5A is a block diagram 200 schematically representing an attenuation arrangement 204 deployable relative to an MRI field 54, according to one example of the present disclosure. In some examples, attenuation arrangement 204 comprises one example implementation of the attenuation arrangement 74 in FIGS. 1-2.

As shown in FIG. 5A, MRI device 202 produces a field 54, in a manner similar to that shown in association with at least FIG. 1. Meanwhile, attenuation arrangement 204 is associated with implantable system 76 (FIG. 2) to attenuate MRI-energy with respect to at least some portions of the implantable system 76.

As shown in FIG. 5A, such an attenuation arrangement 204 may comprise one modality or several different modalities, which in turn may be deployed separately or in combination. In some examples, such modalities include a first shield modality 210, a second shield modality 212, a filter modality 214, an antiphase modality 217, and a dissipation modality 216. In some examples, the respective modalities may be interrelated such as a shield modality blocking or absorbing MRI energy and facilitating dissipation of MRI energy. In another example, in some instances the anti-phase modality may sometimes be considered to be an expression of the dissipation modality 216, as described later in various examples. In some examples, some of the respective modalities may be independent of each other, either based on how they interact with the MRI energy and/or because of their respective positions within the patient's body. At least some specific example implementations of these attenuation modalities are described below with respect to FIG. 5A and later described in association with at least FIGS. 5B-33.

With regard to at least the dissipation modality 216, the example attenuation arrangements seek to dissipate the unwanted RF energy over the largest surface area possible such that the dissipated RF energy density may be minimized as much as possible.

In some examples, the anti-phase modality 217 and/or anti-phase element(s) 253 may address certain effects resulting from the presence of the implantable medical device (e.g. at least lead 72) within a MR field 54. For instance, at least some portion of the RF signals within the MR field may setup small e-fields along the lead 72 with at least some of the respective e-fields having a different magnitude and/or different phases. However, via employing at least an anti-phase modality 217 (e.g. via anti-phase elements 253) of an attenuation arrangement according to at least some examples of the present disclosure, anti-phase conductive structures may be incorporated into at least a portion of a shield structure and/or of other conductive attenuation arrangements. In some such examples, the anti-phase conductive structures (e.g. 253 in FIGS. 5A-5D may employ inversions (and/or manipulations) to create opposing phases of the e-fields, which in turn cancel each other out, thereby substantially eliminating the RF energy that would otherwise impact the lead (and/or other components). In some examples, such anti-phase modalities 217 and/or elements 253 (FIG. 5A) may be implemented according to at least the various examples later described in association with at least FIGS. 19A-19I and/or FIGS. 20A-20F.

With this in mind, in some instances it may be described that from the perspective of the signal conductor (e.g. therapy conductor), the MRI signal may be attenuated. In some instances, it may described that from the perspective of the attenuation arrangement, the MRI signal may be dissipated. In some examples of the attenuation arrangements, e-field shielding works by canceling the e-field by the shift of electrons within the shield. In some such examples, such cancellation of e-fields may be implemented via, and/or viewed as corresponding to, the anti-phase modality 217 (and/or anti-phase elements 253) in at least FIG. 5A.

For high-frequency applications, the e-field can be actually absorbed by the shield to some degree and so ought to be dissipated into the body over an appropriately sized surface. In some examples, the dissipation can occur at a point (e.g. the electrode in an un-shielded lead) such as the IPG or all along (or various points along) the entire shield if capacitively coupled to tissue.

With further reference to FIG. 5A, for illustrative clarity, diagram 200 includes a dashed line 203 to represent an outer portion or outer boundary of at least some portions of implantable system 76 (FIG. 2), such that the first shield 210 is external to and spaced apart from the outer portion of some components of implantable system 76.

On the other hand, any one or several of the other modalities (212, 214, 216, 217) are co-located directly with, or physically incorporated within, components of the implantable system 76 (FIG. 2) as represented by their being on an opposite side of dashed line 203 relative to shield 210.

In some examples, at least one instance of the first shield modality 210 may be positioned externally and spaced apart from an implantable system 76, as represented by distance D1.

As further shown in FIG. 5A, in some examples an array 241 of attenuation elements 240-254 can be utilized to implement the various attenuation modalities 210, 212, 214, 216, 217 according to one example of the present disclosure. As shown in FIG. 5A, in some examples the array 241 includes a coil element 240, a mesh element 242, a flexible printed electronics (FPE) assembly 245, an inductive element 250, a capacitive element 252, an anti-phase element 253, or a combination 254 of some of these elements.

In some examples at least some of these elements may be implemented in various combinations (254) and/or may be implemented simultaneously (even if independently) via a flexible printed electronics (FPE) assembly 245. By doing so, such combinations may be implemented at a reasonable cost and within a much smaller volume than at least some non-FPE constructions. Stated differently, with at least some non-FPE constructions, the cost and difficulty may increase substantially for each additional element employed (in combination) due to at least the materials, assembly cost, complexity of combining different elements, etc. In some instances, these challenges may make implementation of multiple modalities in a non-FPE construction to be impractical and cost prohibitive. However, by employing a FPE assembly 245 according to at least some examples of the present disclosure, a combination of elements (e.g. 240, 243, 250, 252, 253) of an attenuation arrangement 204 may be implemented in a lead assembly (or other implantable medical device) at a reasonable cost and within a reasonable volume without undue difficulty.

In some examples, as shown in FIG. 5A, a portion of implantable system 76 comprises a flexible printed electronic (FPE) assembly 245. A number of different detailed implementations of the FPE assembly 245 are described and illustrated later throughout examples of the present disclosure. However, it can be generally noted that in at least some examples, one or several of the modalities 210, 212, 214, 216, 217 of attenuation arrangement 204 can be incorporated within, defined by, and/or cooperative with such flexible printed electronic assemblies 245.

As further shown in FIG. 5A, the various attenuation elements of array 241 can be further specified with respect to how they relate to a FPE assembly 245. Accordingly, FIG. 5A depicts an array 281 of types of structures 280, 282, 284, and 290, which are identifiable and distinguishable based on their relationship to aspects of a FPE assembly 245.

As shown in FIG. 5A, in some examples array 281 includes a non-FPE assembly discrete structure 280. For instance, structure 280 may correspond to a discrete structure which is not formed as part of a FPE assembly 245 and which can be used to attenuate MRI-energy relative to at least a portion of an implantable system 76. In some examples, a conductive coil 240 or conductive mesh 242 can be formed as discrete elements, which are not part of a FPE assembly 245. In some instances, coil 240 and/or mesh 242 can define an external shield represented via first shield modality 210.

However, in some examples, an external shield (e.g. 210 in FIG. 5A) also can be at least partially defined by a FPE assembly 245, which is distinct and separate from a FPE assembly 245 which forms a lead 72, electrode 102, etc.

As further shown in FIG. 5A, in some examples array 281 includes a dedicated conductive structure 282 of a FPE assembly 245. In such examples, a FPE assembly 245 can be formed to include an attenuation element which takes the form of a dedicated conductive structure in the FPE assembly 245. For instance, a FPE assembly 245 can be formed to include an inductive element 250 and/or capacitive element 252, which are physically separate from, and independent of, other conductive elements of the FPE assembly 245, such as stimulation signal conductive elements and/or sensor signal conductive elements of the FPE assembly 245.

In some examples, array 281 includes a dedicated discrete structure (e.g. component) 284. In some examples, such discrete components 284 are formed as an independent circuit element such as an application specific integrated circuit (ASIC) or field-effect transistor (FET), which is mounted to the FPE assembly 245 (e.g. its substrate) and/or which are at least partially defined by a FPE assembly 245. In some examples, the active element 1125 in FIG. 18A corresponds to a dedicated discrete component 284.

In some examples, array 281 includes a non-dedicated conductive structure (e.g. element) 290 of the FPE assembly. In other words, one of the various attenuation elements of array 241 is formed via a conductive element of the FPE assembly 245, which already has another function. For instance, certain conductive elements of the FPE assembly 245 may already define a signal conductive element for conveying signals for sensing (294) and/or stimulation (292) through a lead 72. In some examples, such conductive elements may be arranged to provide inductive functionality (250) and/or capacitive functionality (252) even though such functionality is implemented via dedicated conductive components physically separate signal conductive element(s). In other words, in such examples, no additional conductive elements are dedicated solely to defining an inductive component and/or to defining a capacitive component to act as an attenuation element. Rather the routing, size, and/or shape of the signal conductive elements (used to convey a stimulation signal and/or a sensor signal) is configured to cause or enable inductive behavior and/or capacitive behavior. This behavior can attenuate MRI-energy according to a shield, filter, dissipation, and/or anti-phase modality (e.g. 212, 214, 216, 217).

FIG. 5B is a block diagram 300 schematically representing an attenuation arrangement in association with a lead assembly 302, according to one example of the present disclosure. As shown in FIG. 5B, lead assembly 302 includes lead 72 and electrode 102. The lead 72 extends between a proximal end 105 and a distal end 103, with electrode 102 connected to the distal end 103. It will be understood that, in some examples, at least lead 72 is formed of a FPE assembly (245 in FIG. 5A) to implement an attenuation arrangement (204 in FIG. 5A). As shown in FIG. 5B, in some examples the attenuation arrangement comprises at least an array 305 of inductive elements (L) arranged along lead 72, and thereby implementing the inductive modality 250 in FIG. 5A. The inductive elements L are spaced apart from each other by a distance D2 as they extend along length L1 of lead 72. Distance D2 can be uniform between all the inductive elements L or can be different between some adjacent inductive elements in order to meet attenuation design goals.

In some examples, lead 72 is formed as an FPE assembly comprising a layered stack of signal conductive elements, insulative elements, shield conductive elements, etc. (as later described in association with at least FIGS. 6A-33). The inductive elements L can be positioned between adjacent layers, within a single layer, and/or extend from one layer to another layer, etc. in order to arrange for a target inductance at certain locations along lead 72 and/or to achieve an overall pattern of inductance. In one aspect, the deployment of such inductive elements L may be considered a form of passive filtering of MRI energy.

In one aspect, such arrangements of inductive elements may reduce a magnitude of MRI energy that would otherwise tend to dissipate into the body 72 as a result of the MRI magnetic field inducing an electric field in the patient's body. In particular, the particular arrangement of inductive elements L along lead 72 can work to modify the transfer function associated with such coupling (of the e-fields onto the lead 72) resulting in a strategic reduction in a magnitude and/or altered phase of the transfer function. In some examples, the transfer function may be at least partially defined based on a relationship between a tangential electric field (E-tan) along the lead body (e.g. 72) and an RF energy dissipated at the lead electrodes 102 and/or heating at the lead electrodes 102.

In some examples, the deployment of inductive elements L corresponds to the filter modality 214 in FIG. 5B with such inductive elements L sometimes being referred to as a passive component. In some examples, placement of at least one inductive element L at the end of conductive elements of lead 72 may help filter out MRI energy. In some examples, such placement of inductive element(s) L may combine with an electrode-tissue capacitance and/or resistance to function as a low pass filter, thereby attenuating the MRI/RF energy. However, such a filter may not attenuate a stimulation signal in lead 72 because the dominant frequency components of the stimulation signal are at least one order of magnitude lower in frequency than the filter cutoff.

In some examples, a transistor such as field effect transistor (FET) also may produce similar results in filtering MRI energy.

FIG. 5C is a block diagram 320 schematically representing an attenuation arrangement in association with a lead assembly 322, according to one example of the present disclosure. In some examples, lead assembly 322 comprises at least some of substantially the same features as lead assembly 302 in FIG. 5B, except having a more comprehensive attenuation arrangement 324. As shown in FIG. 5B, an array 323 of attenuation elements A are shown positioned along a length L1 of the lead 72 and along a length L2 of the electrode 102.

As shown in FIG. 5C, the attenuation arrangement 324 may include one type of element or a combination of several different types of elements, including inductive elements L, capacitive elements C, resistance elements R, anti-phase elements (AP), shield elements (S) and/or circuitry combined in an application specific integrated circuit (ASIC) or in a field effect transistor (FET).

It will be understood that, in some examples just some of the attenuation elements A are implemented and the spacing (D2) among multiple attenuation elements A may vary depending on the type and number of attenuation elements A. In some examples, the ASIC or FET may correspond to the active attenuation element as later described in association with FIG. 18A.

Moreover, in some examples, attenuation elements A are implemented solely with respect to electrode 102 in zone B or attenuation elements A are implemented solely with respect to lead 72.

In some examples, at least some shield elements (S) may be implemented along at least the lead 72 with such shield element(s) being in contact with surrounding bodily tissues and/or fluids. In some such examples, at least some capacitive elements (C) may be implemented as part of lead 72 and/or at part of a connecting block (e.g. header) of the IPG 104 with such capacitive elements (C) acting to present a short at MRI RF frequencies between signal conductors (e.g. for sensing and/or stimulation) and the shielding element(s).

In some examples, at least some shield elements (S) may be implemented along at least the lead 72 with such shield element(s) being in contact with, or adjacent to, surrounding bodily tissues and/or fluids. In some such examples, at least some capacitive elements (C) may be implemented as part of lead 72 and/or at part of a connecting block (e.g. header) of the IPG 104 with such capacitive elements (C) acting to present a short at MRI RF frequencies between the conductive case of the IPG 104 and the shielding element(s). In this way, the RF energy present on the shield is dissipated by the case (e.g. external housing) of the IPG (e.g. 104 in FIG. 2, 135 in FIG. 4, 760 in FIG. 11) while not affecting the normal therapy function of the case of the IPG (e.g. 104, 135, 760), such as when using at least a portion of the case as a stimulation electrode (e.g. an anode).

In some examples, the effective length of the lead at the frequency of the MRI RF energy may be chosen as one-half the wavelength of the MRI RF energy. In this way, the conductors form an anti-phase attenuation arrangement by virtue of the anti-resonant properties of the conductor at this wavelength. It should be noted that the wavelength of the MRI RF energy in tissue is shorter than in air, as the permittivity of tissue is roughly two orders of magnitude larger than in air. Accordingly, the wavelength of the MRI RF energy in tissue is roughly one order of magnitude shorter than in air as the wavelength is proportional to the inverse of the square root of the permittivity.

Figure 6A:
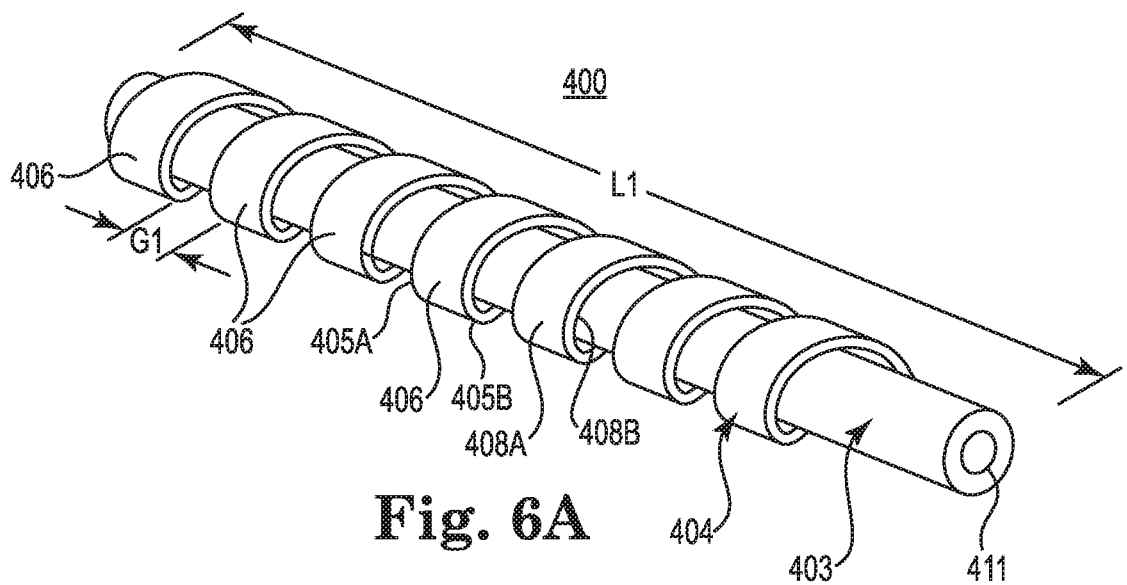
FIG. 6A is a perspective view schematically representing an implantable lead assembly including a flexible printed electronics (FPE) assembly in a helically wound configuration relative to an elongate support member, according to one example of the present disclosure.

FIG. 6A is a perspective view schematically representing an implantable lead assembly 400 including a FPE assembly 404 in a helically wound configuration, according to one example of the present disclosure. As shown in FIG. 6A, lead assembly 400 includes an elongate support member 403 about which FPE assembly 404 is helically wound. In some examples, FPE assembly 404 comprises at least some of substantially the same features and attributes as a FPE assembly 245 in association with at least FIGS. 5A-5C and/or as later described in association with at least FIGS. 6B-33. In some examples, the elongate support member 403 comprises a flexible, resilient member to provide strength, which can enhance flex resistance, handling, and/or durability. In some examples, the elongate support member 403 is non-conductive, e.g. electrically insulative.

Figure 6B:
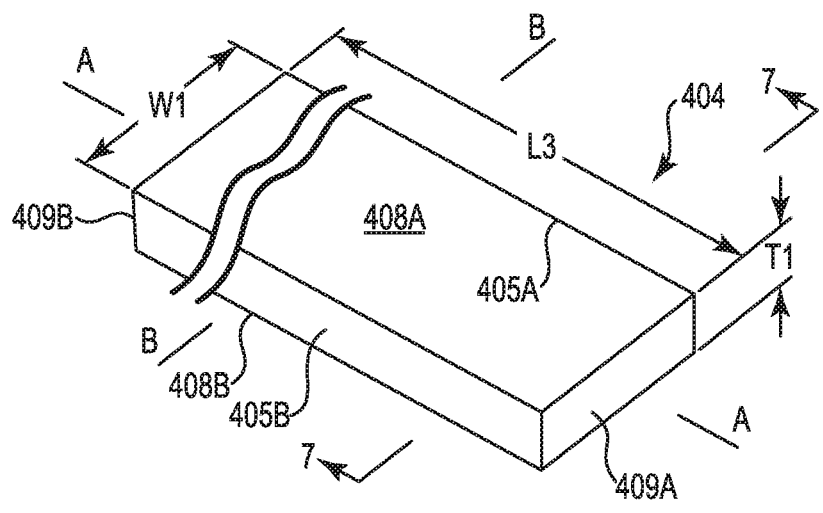
FIG. 6B is a perspective view schematically representing an implantable lead assembly including a FPE assembly in an un-wound configuration, according to one example of the present disclosure.

However, prior to further describing the lead assembly 400, reference is made to the perspective view of FIG. 6B which schematically represents the FPE assembly 404 in its unwound (e.g. straight) configuration. As shown in FIG. 6B, in some examples the FPE assembly 404 defines a relatively thin, elongate rectangular member which extends lengthwise (L3) between opposite ends 409A, 409B and has a width W1 between opposite sides 405A, 405B. FPE assembly 404 also has a top surface 408A and an opposite bottom surface 408B, which define a thickness T1 therebetween. In some examples, the width W1 is substantially greater than the thickness T1 and in some examples, the width W1 may be at least one order of magnitude greater than the thickness T1. In some examples, the length L3 is substantially greater than the thickness T1 or width W1, and in some examples, the length L3 may be at least one order of magnitude greater than the thickness T1 or width W1. In some examples, length L3 may be at least two orders of magnitude greater than the thickness T1 or width W1.

As further shown in FIG. 6B, a length of the FPE assembly 404 extends in a first orientation A parallel to a longitudinal axis of the FPE assembly 404, while a width of the FPE assembly 404 extends in a second orientation B transverse to orientation A.

Moreover, it will be understood that the length L3 of the FPE assembly 404 prior to being helically wound as in the example of FIG. 6A, will be substantially greater than the length L1 of the lead assembly 400. In some examples, the length L3 may be at least one order of magnitude greater than the length L1.

Meanwhile, the FPE assembly 404 comprises an array of signal conductive elements such that, via FPE assembly 404, lead assembly 400 can convey stimulation signals and/or sensor signals along a length (L1) of the lead assembly 400 such as from an IPG 104 to an electrode 102.

It will be understood that FPE assembly 404 can have a wide variety of configurations of signal conductive elements and non-signal conductive elements, with at least some examples of such configurations described throughout the present disclosure.

In some examples, a FPE assembly 404 may comprise electronic structures formed via printing the respective insulative and conductive elements as layers with at least some of the insulative material corresponding to a flexible substrate generally supporting and/or forming the entire assembly 404. While the flexible substrate may allow some bending and flexing, it exhibits enough resilience to withstand repeated flexing and bending while maintaining its structural integrity and maintaining the adhesion of conductive elements printed relative to the substrate. Moreover, by employing the substrate (in a FPE assembly 404) in a coiled configuration as shown in at least FIG. 6A, the coiled configuration may enhance protecting the structural integrity of the substrate and FPE assembly 404 during flexing, bending, stretching, etc.

In some examples, the substrate can be formed from a liquid crystal polymer (LCP) material, a polyimide material, a polyether ether ketone (PEEK) material, and other dielectric polymers.

In some examples, the flexible substrate may enable complex geometries that can be folded, stacked, molded over, and curved around the lead bodies. This capability allows many configurations of printed components and elements, thereby enabling close control over target parameters in design of a lead assembly to meet MRI energy attenuation goals and to keep lead manufacturing repeatable and low cost.

In forming this assembly 404, whole or partial layers are printed of the various materials to define a monolithic structure, which is inclusive of the targeted physical and electrical functionality to perform electronic functions, such as conveying signals and/or other more complex electronic functions.

With this in mind, further reference is made to the perspective view in FIG. 6A of lead assembly 400. In the helically wound configuration, the FPE assembly 404 defines a plurality of windings 406, with each winding having a pair of opposite outer edges 405A, 405B. A gap G1 is formed between adjacent windings 406.

The elongate support member 403 comprises a generally cylindrical member. In some examples, support member 403 defines a lumen 409 extending throughout a length of support member 403. Via this arrangement, the elongate support member 403 has greater flexibility and exhibits the same general functionality but while using less material. In some examples, the elongate support member 403 defines a core of the lead assembly 400. In some examples, the elongate support member 403 is made from a material, such as silicone, polyurethane, etc. Via this arrangement, the elongate support member 403 helps to prevent kinking of the lead assembly 402, provides increased flex resistance, and/or provides a feel to the operator that more closely resembles a traditional lead structure.

It will be understood that the terms insulative and insulator may be used interchangeably throughout the present disclosure, and generally refer to materials which are electrically non-conductive. In this regard, in some instances such insulative material may sometimes be referred to as a dielectric material or dielectric coating.

In some examples, the helically wound configuration of the FPE assembly 404, in combination with the elongate support member 403 provides for pushability, steerability, torquability, and sufficient flexibility to promote advancement and maneuvering the lead assembly 400 within a body portion. In some examples, the gap G1 is selected to provide enough flexibility to enable adequate maneuverability yet provide enough resilience (e.g. firmness or rigidity) to enable pushing and steering of the lead assembly 400.

Figure 6C:
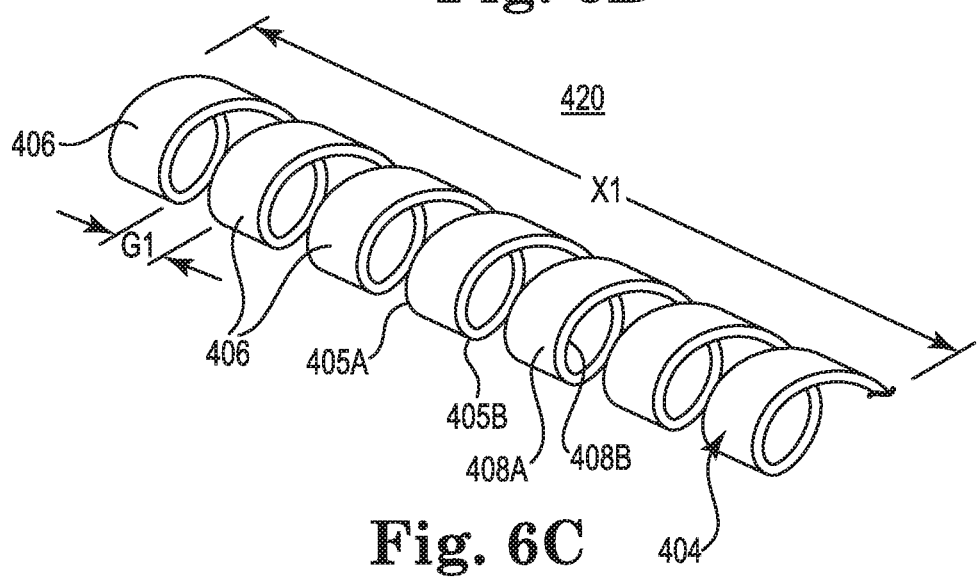
FIG. 6C is a perspective view schematically representing an implantable lead assembly including a FPE assembly and omitting an elongate support member, according to one example of the present disclosure

FIG. 6C is a perspective view of a lead assembly 420, according to one example of the present disclosure. In some examples, lead assembly 420 comprises at least substantially the same features and attributes as the lead assembly 400, except for the general arrangement omitting the elongate support member 403 such that the FPE assembly 404 comprises the sole component of lead assembly 420.

It will be further understood that in some examples, when FPE assembly 404 comprises the sole component of lead assembly 420, the FPE assembly 404 may have a straight configuration (FIG. 6B) or may have a three-dimensional shape configuration other than being helically wound, such as undulating, sinusoidal, folded, etc.

Figure 7A:
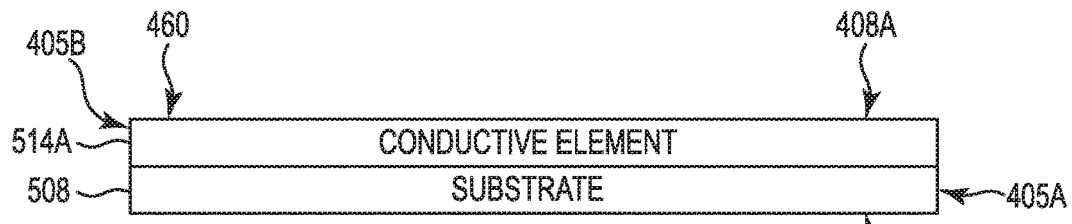
FIG. 7A is a sectional view schematically representing a FPE assembly, according to one example of the present disclosure.

FIG. 7A is a diagram including a sectional view schematically representing a FPE assembly 460, according to one example of the present disclosure, which is just one example implementation of FPE assembly 404 in FIGS. 6A-6C and 245 in FIG. 5A. As shown in FIG. 7A, in general terms FPE assembly 460 includes a conductive element 514A and a substrate 508 relative to which the conductive element 514A can be printed. Via this arrangement, the conductive element 514A can convey a signal along the length of the FPE assembly (e.g. 404 in FIG. 6A), thereby conveying the signal along the length L1 of the lead assembly (400 in FIG. 6A).

In some examples, the substrate 508 provides a foundation on which a signal conductive element 514A can be printed and relative to which other elements can be printed. In some examples, the substrate 508 and at least some other insulative materials of the various FPE assemblies (as described throughout examples of the present disclosure) comprise at least some of substantially the same features as the substrate described in association with at least FIG. 6A-6C.

It will be understood that, in some examples, the same material from which the substrate is formed also can be used to form an outer insulative layer of a FPE assembly, to insulate an entire lead assembly, etc.

As further described in association with at least FIGS. 7B-7E, 10-12, 15-16, 18D, in some instances at least a portion of the substrate 508 may be referred to as a base insulator 510.

Figure 7B:
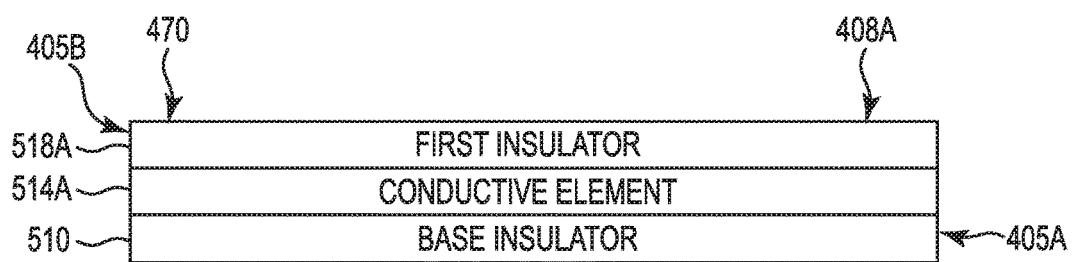
FIG. 7B is a sectional view schematically representing a FPE assembly, according to one example of the present disclosure.

FIG. 7B is a diagram including a sectional view schematically representing a FPE assembly 470, according to one example of the present disclosure, which is just one example implementation of FPE assembly 404 in FIGS. 6A-6C and 245 in FIG. 5A. The FPE assembly 47 comprises at least some of substantially the same features and attributes as the FPE assembly 460 (FIG. 7A), except further comprising a first insulator 518A such that signal conductive element 514A becomes common to, and sandwiched between, base insulator 510 and the first insulator 518A.

It will be understood that in some examples the signal conductive element 514A may not be entirely conductive. In other words, the signal conductive element 514A may comprise a layer of non-conductive material (e.g. a substrate) which carries or supports at least one conductive trace which serves as the signal conductor. In some examples, a printed circuitry construction may be employed in which the base insulator 510 may serve as the substrate onto which the conductive traces are printed such that conductive element 514A in FIG. 7B may be considered not to be a physically separate element from base insulator 510. In some examples, the at least one conductive trace may comprise several independent conductive traces which each carry different electric signals.

In some examples, the arrangement later described in association with FIG. 13 and/or FIG. 14 may comprise one example implementation of the conductive element 514A in FIG. 7B.

Figure 7C:
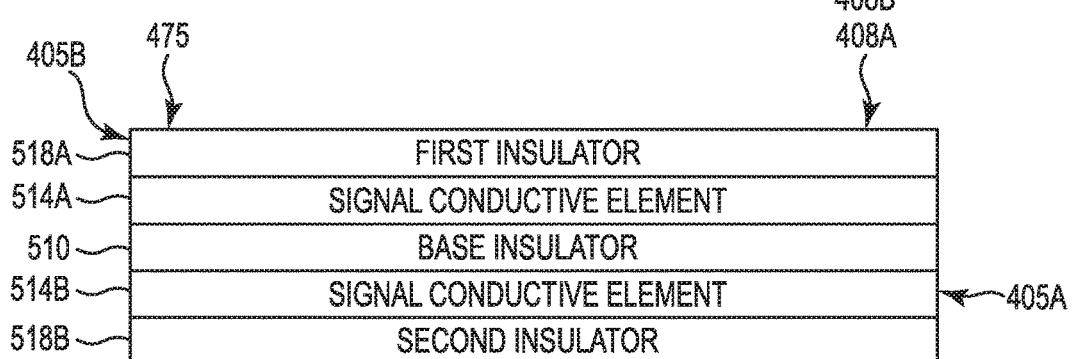
FIG. 7C is a sectional view schematically representing a FPE assembly including two signal conductive elements, according to one example of the present disclosure.

FIG. 7C is a diagram including a sectional view schematically representing a FPE assembly 475, according to one example of the present disclosure, which is just one example implementation of FPE assembly 404 in FIGS. 6A-6C and 245 in FIG. 5A. The FPE assembly 475 comprises at least some of substantially the same features and attributes as the FPE assembly 470 (FIG. 7B), except further comprising a second signal conductive element 514B, such that base insulator 510 becomes common to, and sandwiched between, the pair of signal conductive elements 514A, 514B. Meanwhile, as further shown in FIG. 7C, a pair of insulators 518A, 518B are external to the signal conductive elements 514A, 514B.

Figure 7D:
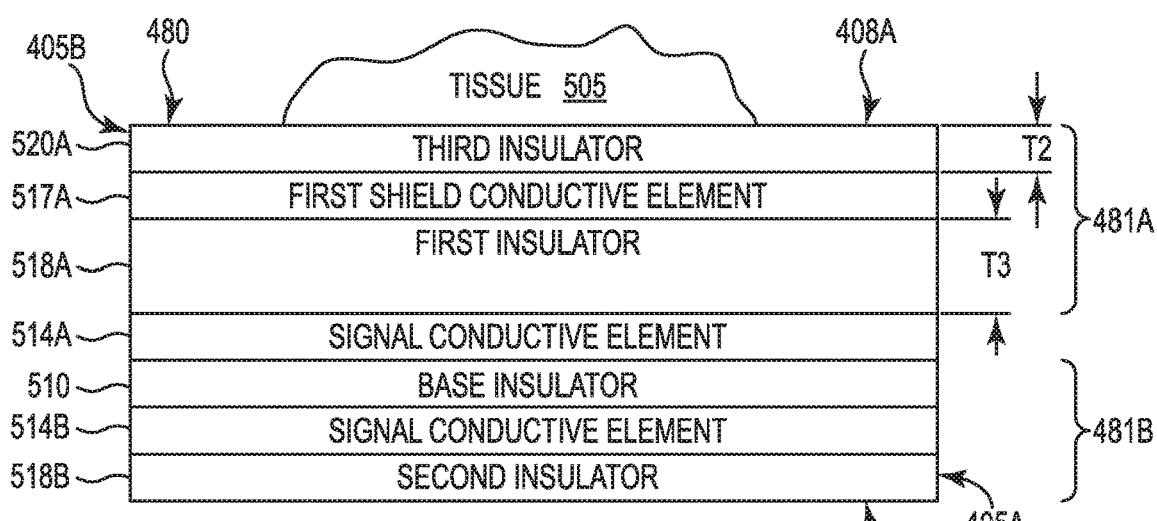
FIG. 7D is a sectional view schematically representing a FPE assembly including at least one shield conductive element, according to one example of the present disclosure.

FIG. 7D is a diagram 500 including a sectional view schematically representing a FPE assembly 480, according to one example of the present disclosure, which is just one example implementation of FPE assembly 404 in FIGS. 6A-6C and 245 in FIG. 5A. The FPE assembly 480 comprises at least some of substantially the same features and attributes as the FPE assembly 475 (FIG. 7C), except further comprising a first shield conductive element 517A as shown in FIG. 7D.

In some examples, the first shield conductive element 517A comprises the sole shield conductive element of the flexible printed electronic assembly. As shown in FIG. 7D, the first shield conductive element 517A is located on an upper portion 481A of the FPE assembly 480 to be located closer to an upper outer surface 408A of the FPE assembly 480. Via this arrangement, the flexible printed electronic assembly 480 does not include a comparable shield conductive element on lower portion 481B at a position interior of the upper outer surface 408A of FPE assembly 480.

In some examples, the first shield conductive element 517A may be in indirect contact with bodily tissues and/or body fluids. In some examples, this indirect contact may be achieved via placing small holes (e.g. pin size) in the third insulator 520A to thereby enhance coupling of the RF energy to the first shield conductive element 517A.

In some examples, the arrangement of FIG. 7D is deployed in at least some examples in which the FPE assembly 480 is in a helically wound configuration with the outer surface 480A defining the outermost surface of the FPE assembly 480. In this way, shielding is provided for the interiorly located signal conductive elements 514A, 514B, as described and/or illustrated in association with at least FIGS. 6A, 6C, 19-21, 23, and 25.

In some examples, the example arrangement of FIG. 7D is deployed in at least some examples in which the FPE assembly 480 is in a straight configuration (e.g. not helically wound) with the outer surface 480A defining the outermost surface of the FPE assembly 480 to shield the interiorly located signal conductive elements 514A, 514B.

In some examples, in which a FPE assembly such as FPE assembly 480 acts solely as a shield structure (e.g. not to convey a signal), then a similar arrangement of a single shield conductive element can be implemented. In some such examples, the FPE assembly can adopt the arrangement of either FIG. 7A or FIG. 7B in which the conductive element 514A is implemented as a shield conductive element and not to convey a signal.

As further shown in FIG. 7D, in some examples of the FPE assembly 480, a first insulator 518A has a thickness T3, which is substantially greater (e.g. 2×, 3×) a thickness T2 of a third insulator 520A in contact with tissue 505. Via this arrangement, in some examples, the thickness T2 of the third insulator 520A is relatively thin (e.g. minimized) to increase capacitance between the first shield conductive element 517A and the body tissue 505, which thereby facilitate dissipation of energy from the first shield conductive element 517A upon its absorption of MRI RF energy. Meanwhile, in one aspect, the relatively larger thickness T3 of the first insulator 518A may decrease capacitive coupling from the first shield conductive element 517A to adjacent signal conductors, such as but not limited to at least signal conductive element 514A.

In some examples, a total surface area of the first shield conductive element 517A is formed as a contiguous sheet or layer of conductive material (e.g. not a mesh but a solid plane of conductive material) to increase capacitance between the first shield conductive element 517A and the body tissue 505.

Figure 7E:
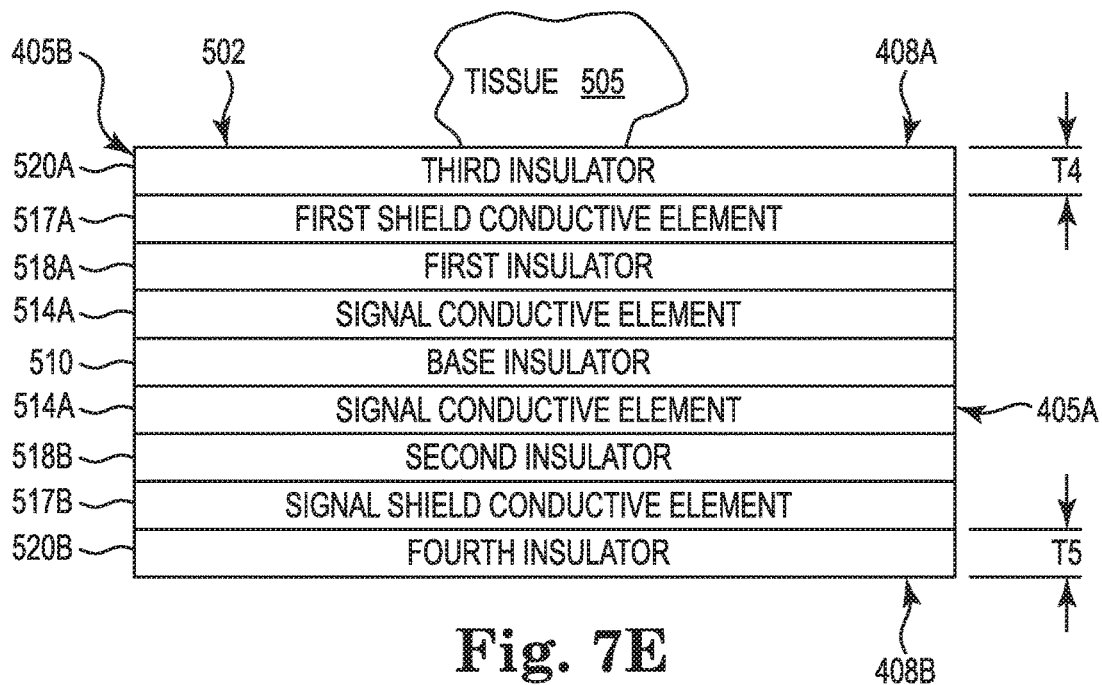
FIG. 7E is a sectional view schematically representing a FPE assembly including two shield conductive elements, according to one example of the present disclosure.

FIG. 7E is a diagram 500 including a sectional view schematically representing a FPE assembly 502, according to one example of the present disclosure, which is just one example implementation of FPE assembly 404 in FIGS. 6A-6C and 245 in FIG. 5A. As shown in FIG. 7E, in general terms FPE assembly 502 includes an array of elements (510, 514A, 514B, 518A, 518B, 517A, 517B, 520A, 520B) arranged as layers in a vertically stacked relationship.

The FPE assembly 502 comprises at least some of substantially the same features and attributes as the FPE assembly 480 (FIG. 7D), except further comprising a second shield conductive element 517A and a fourth insulator 520B as shown in FIG. 7E. The pair of shield conductive elements 517A, 518A are external to the first and second insulators 518A, 518B. The third and fourth insulators 520A, 520B are external to the respective shield conductive elements 517A, 517b and also define an outermost layer of the FPE assembly 502.

Meanwhile, the pair of shield conductive elements 517A, 517B at least partially surround the signal conductive elements 514A, 514B to attenuate MRI-energy relative to at least the signal conductive elements 514A, 514B. The shield conductive elements 517A, 517B correspond to at least the shield modality 212 in FIG. 5A.

In some examples, a FPE assembly 502 having a respective shield conductive element 517A. 517B on opposite sides of the signal conductive elements 514A, 514B can be used in one of the examples in which the FPE assembly 502 is deployed in a generally straight configuration (e.g. a non-helically wound configuration), such as later described in association with at least FIGS. 22-24.

In some examples, the shield conductive elements 517A, 517B comprise a mesh structure. However, in some examples, the shield conductive elements 517A, 517B can comprise a solid sheet of conductive material. In some examples, the solid sheet comprises a contiguous layer lacking holes, such as an uninterrupted plane of material.

In one aspect, to the extent that the entire FPE assembly 502 may be arranged in a helically wound configuration as in the lead assembly 400 of FIG. 6A, then the shield conductive elements 514A, 514B also can be understood to define a coil (240 in FIG. 4). Accordingly, in some examples, the gap G1 between windings 406 in FIG. 6A is at least one order of magnitude less than a wavelength of MRI field signals (within the body).

In some examples, the FPE assembly 502 is configured to provide RF shielding by providing a path for RF-induced e-fields (MRI-energy) to be dissipated. In particular, in one aspect the shield conductive elements 517A are provided beneath a third insulator 520A having a relatively small thickness (T4) such that the electrical energy absorbed by the shield conductive element 517A is dissipated via a passive high-pass filter (capacitor) created between the shield conductive element 517A and the surrounding tissue 505.

In one aspect, by implementing this shielding arrangement of a shield conductive element 517A covered by a thin insulator 520A as part of a FPE assembly, precise control over the parameters of the shield design can be achieved. In particular, in some examples insulator 520A would have a thickness (T4) on the order of less than 0.1 millimeters with a tolerance of less than 0.1 millimeters.

Accordingly, by constructing the shield conductive element 517A and covering insulator 520A via printing those elements as part of the FPE assembly, one can tightly control the thickness (T4, T5) of the insulator 520A, 520B. By doing so, the relatively thin layer of insulative material between the shield and the patient's tissue 505 may ensure that high frequency energy is effectively dissipated by the shield into the body by virtue of the capacitance formed between the tissue and insulators 520A, 520B, which presents a low impedance to high frequency RF energy. In this way, the shield conductive elements 518A, 518B exhibit both a shield (e.g. blocking) modality 212 and a dissipation modality 216 (FIG. 5A).

Figure 17A:
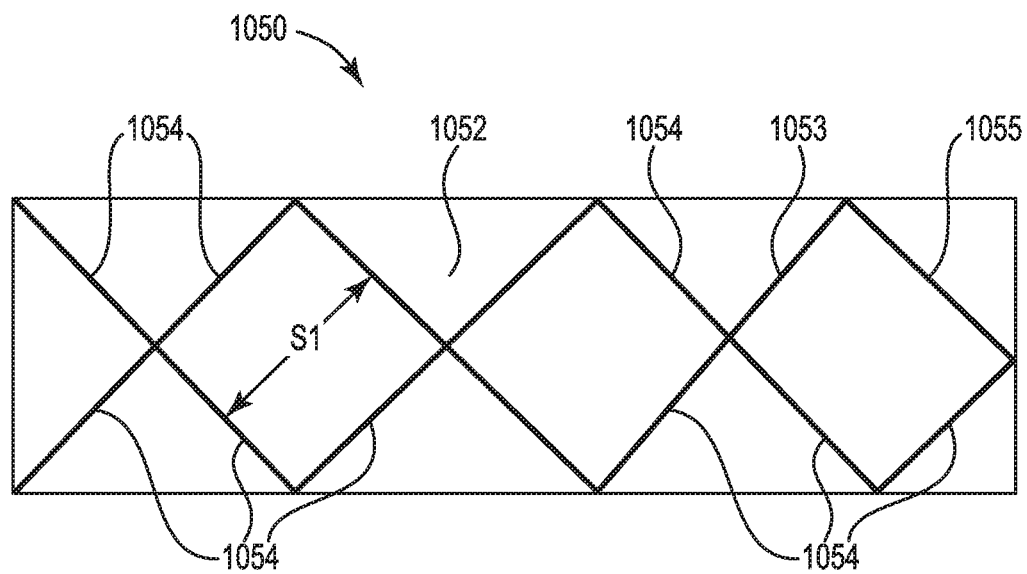
FIG. 17A is a top view schematically representing a portion of a FPE assembly including a signal conductive element arranged in a mesh pattern, according to one example of the present disclosure.

In some examples, the shield conductive element 517A is formed as a mesh, such as a pattern of conductive elements defining a network of apertures or spacings at least one order of magnitude less than the wavelength of the targeted RF energy (within the body). In some examples, the RF energy can be 64 MHz for a 1.5T scanner or can be 128 MHz for 3T scanner. This arrangement may prevent the shield conductive element 517A from acting an RF-energy attracting antenna. In some examples, the shield conductive element 517A can take the form of a mesh as shown in FIG. 17A or as in FIG. 8A.

In some examples, the base insulator 510 may be considered a substrate on which the signal conductive elements 514A, 514B are printed and relative to which other elements are printed. In some examples, the base insulator and at least some other insulative materials of FPE assembly 502 comprise at least some of substantially the same features as the substrate described in association with at least FIG. 6A-6C.

Figure 8A:
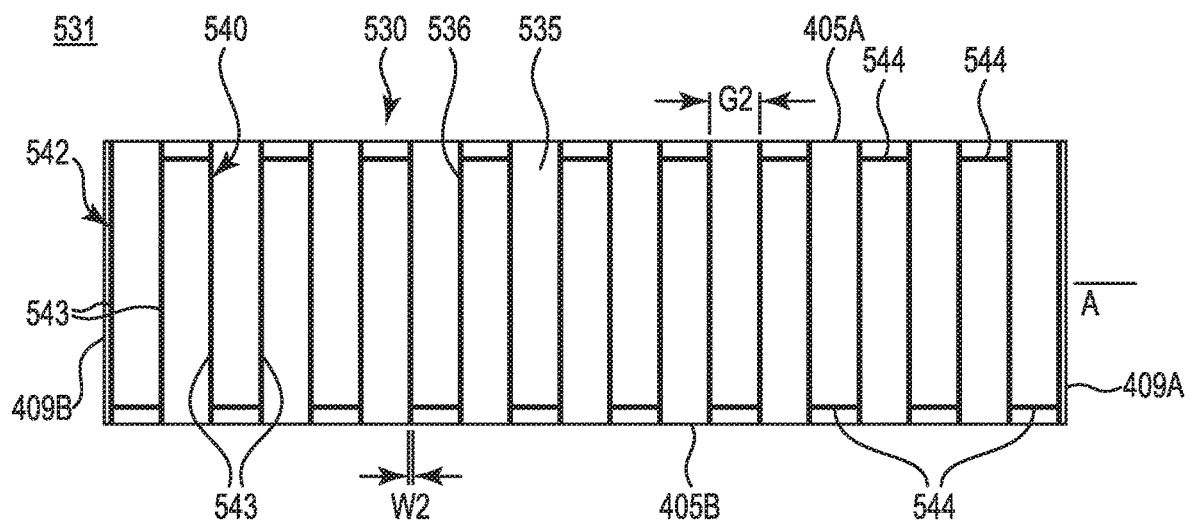
FIG. 8A is a top view schematically representing a portion of a FPE assembly including a conductive element arranged as a mesh on an insulator, according to one example of the present disclosure.

FIG. 8A is a top view schematically a portion of a FPE assembly 530 including a conductive element on an insulator, according to one example of the present disclosure. In some examples, this arrangement may be deployed as one of the shield conductive elements of the 517A, 517B or as one of the signal conductive elements 514A, 514B of the FPE assembly 502 in FIG. 7E. When used as a signal conductive element, this structure may provide improved filtering relative to a linear conductor by virtue of the increased inductance of the conductor.

As shown in the diagram 531 of FIG. 8A, a portion of a FPE assembly 530 includes an insulator element (e.g. layer) 535 on which a conductive element 536 has been printed in a pattern 540. In such examples, the insulator layer 535 in FIG. 8A may correspond to one of the insulators (518A, 518B) in FIG. 7 and the conductive element 536 defining the pattern 540 in FIG. 8A may correspond to a respective one of the shield conductive elements (517A, 517B) in at least FIG. 7E.

Figure 8B:
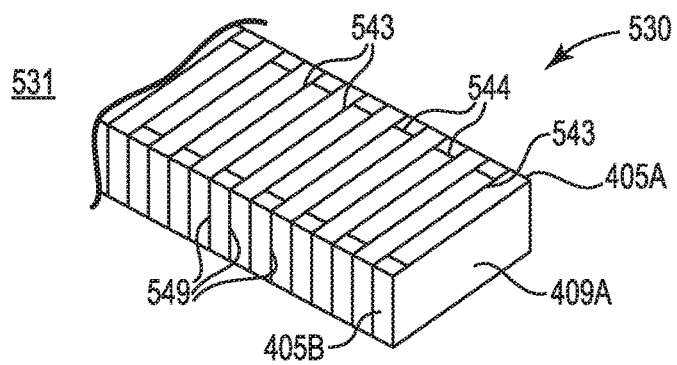
FIG. 8B is a perspective view schematically representing the portion of the FPE assembly in FIG. 8A, according to one example of the present disclosure.

As shown in FIG. 8A-8B, in some examples the pattern 540 comprises an array 542 of struts 543, which are spaced apart from each other and extend general parallel to each other in an orientation B (FIG. 6B), which is transverse to a longitudinal axis (e.g. orientation A in FIG. 6B) of the FPE assembly. The pattern 540 also comprises an array of cross members 544 which are aligned generally transverse to the struts 543, with each cross member 544 connecting an adjacent pair of struts 543. In one aspect, in some examples, via this pattern 540, the various struts 543 and cross members 544 define a single connected conductive element which can function as a mesh 242 (FIG. 4) and shield conductive element (517A or 517B) or signal conductive element 514A, 514B. Accordingly, in some examples, a spacing G2 is at least one order of magnitude less than such wavelengths of the MRI field signals (within the body). In some examples, such spacing G2 is at least two orders of magnitude less than such wavelengths of the MRI field signals (within the body).

Via this arrangement, a shield modality 212 or a filter modality 214 of an attenuation arrangement 204 in FIG. 5A is implemented via a mesh 242 type of attenuation element. An FPE assembly 245 (FIG. 5A) with conductive element 536 in FIG. 8A is one implementation of a dedicated conductive structure 282 (of an FPEA) as represented in FIG. 5A.

In one aspect, the pattern 540 in FIG. 8A can be viewed as providing a serpentine looping configuration which can increase inductance of the signal conductive element 514A, 514B, thereby enhancing attenuation of the MRI-energy field signals. In some examples, a width W2 of the conductive struts 543 and/or a width of the cross members 544 can be reduced to further increase the inductance, and thereby further enhance such attenuation.

In some examples, as shown in the perspective view of FIG. 8B, the printed pattern 540 also comprises a plurality of printed vias 549 extending (vertically) on, and partially defining, the sides 405A, 405B of the FPE assembly 530. The vias 549 further surround the signal conductive elements 514A, 514B within a shielding structure to enhance attenuate MRI-energy relative to the signal conductive elements 514A, 514B.

As will apparent from additional examples, additional insulative structures, such as but not limited to, insulators 520A, 520B in FPE assembly 502 in at least FIG. 7E can be used to control capacitive coupling of the shield pattern 540 relative to surrounding tissue 505.

FIG. 9 is a diagram 590 including a perspective view schematically representing a portion 591 of a FPE assembly including a conductive element 592 forming a three-dimensional (3D) coil structure 593 relative to an insulator portion 595, according to one example of the present disclosure.

In some examples, this arrangement may be deployed to implement at least the shield conductive elements 517A, 517B of the FPE assembly 502 in FIG. 7. In some examples, this arrangement may be deployed to implement other conductive elements, such as but not limited to a signal conductive element of an FPE assembly in some examples of the present disclosure.

As shown in FIG. 9, the insulator portion 595 includes at least a top surface 597 and a bottom surface 598, and in some examples, the top surface 597 corresponds to an exposed insulator layer 518A in FIG. 7 and the bottom surface 598 corresponds to an exposed insulator layer 581B in FIG. 7. Meanwhile, a pattern 605 of conductive material is arranged in the 3D coil structure 593 relative to the insulator portion 595.

In some examples, as shown in FIG. 9 the 3D coil structure 593 includes a conductive strut 610 on top surface 597, and conductive strut 612 (shown in dashed lines) is on bottom surface 598. In some examples, each respective strut 610, 612 includes a first portion 611 with both first portions 611 extending general parallel to each other in the second orientation B, which is transverse to the first orientation A which extends parallel to a longitudinal axis of the FPE assembly (as represented by directional arrow A).

In some examples, each strut 610, 612 may correspond to a layer such as a shield conductive element 517A, 517B, respectively or such as signal conductive element 514A, 514B, respectively.

Each strut 610, 612 also includes a second portion 613 extending in the first orientation (A) generally transverse to main portion 611, with vertically extending conductive struts 620 connecting the second portions 613 of the respective top and bottom conductive struts 610, 612. As shown in FIG. 9, together these struts 610, 612, 620 form the 3D coil structure 593, which can act as a filter, such as filter modality 214 of the attenuation arrangement 204 in FIG. 4. In some examples, the coil structure 593 may serve to increase the inductance of the conductor, thereby increasing the impedance of the conductor at high frequencies, thereby forming a filter for RF energy. The vertically extending struts 620 may sometimes be referred to as vias.

In some examples, a spacing G3 is at least one order of magnitude (or at least two orders of magnitude) less than a wavelength of the MRI-energy field signals (within the body).

In some examples, the conductive structures as described and illustrated in association with FIGS. 8A, 8B, 9 may further embody an arrangement of multiple conductive elements carrying independent signals in a manner substantially similar to the arrangement as later described in association with FIG. 13. In some examples, the conductive structures as described and illustrated in association with FIGS. 8A, 8B, 9 may further embody an arrangement of multiple conductive elements carrying the same signal in a manner substantially similar to the arrangement as later described in association with FIG. 14.

FIG. 10 is a diagram including a sectional view schematically representing a FPE assembly 700, according to one example of the present disclosure. In some examples, FPE assembly 700 comprises at least some of substantially the same features as FPE assembly 502 of FIG. 7E, except for additionally comprising additional layers of shield conductive elements 718A, 7186 and an additional layer of outer insulators (720A, 720B).

In particular, layered externally to third and fourth insulators 520A, 520B, the FPE assembly 700 includes a third shield conductive element and a fourth shield conductive element 718A, 7186, with fifth and sixth insulators 720A, 720B being provided as outer insulative covers.

In some examples, the third and fourth shield conductive elements 718A, 718B comprise at least substantially the same feature and attributes as the first and second shield conductive elements 517A, 517B (FIG. 7E). In some examples, the third and fourth shield conductive elements 718A, 718B comprise at least some features and attributes different than the first and second shield conductive elements 517A, 517B. In some examples, such differences may include having a different type of mesh, being a solid sheet, or one pair of shield elements (inner or outer) being formed as a three-dimensional coil structure as in FIG. 9 and the other pair shield element being formed as mesh or some other shielding structure.

Via the arrangement in FIG. 10, a double layer of shielding is provided to further enhance attenuation of MRI energy such as via enhancing capacitive coupling to the surrounding tissue. In one aspect, the capacitance value is controlled by selecting a size or area of the shield conductive elements 517A, 718A, and 517B, 718B, their shape, and a separation between the layers, such as between the first and third shield conductive elements 517A, 718A and between the second and fourth shield conductive elements 517B, 718B. The separation is controlled via selecting a thickness (T4, T5) of the respective third and fourth insulators 520A, 520B.

In some examples, the shielding arrangement in FIG. 10 corresponds to at least the shield modality 212 and/or dissipation modality 216 and/or antiphase modality 217 in the attenuation arrangement of FIG. 5A.

FIG. 11 is diagram 750 including a sectional view schematically representing a FPE assembly 502 and a block diagram of an implantable pulse generator (IPG) 760 to which the FPE assembly of an implantable lead assembly is coupled, according to one example of the present disclosure. In some examples, the FPE assembly 502 comprises at least some of substantially the same features as FPE assembly 502 in FIG. 9. In some examples, the IPG 760 comprises at least some of substantially the same features and attributes as IPG 104 in FIG. 2.

As shown in FIG. 11, in some examples the first shield conductive element 517A and the second shield conductive element 517B are physically and electrically coupled via elements 752A, 752B to an external conductive surface 764 of a housing 762 of the IPG 760. Via this arrangement, the MRI-energy may be dissipated over a larger surface area within the body than attempting dissipation solely at an electrode or at the lead. In other words, the housing 762 of the IPG 760 may act as an energy sink for the MR energy collected by the shield (e.g. shield conductive elements 517A, 517B) of the FPE assembly (or even external shield). The extent to which the IPG housing 762 may act as an energy sink may depend on the length of the associated lead assembly, magnitude of MR energy, surface area of the IPG housing 762, and type of tissues surrounding the IPG housing 762.

Accordingly, in one respect, the shield conductive elements correspond to the shield modality 212 of the attenuation arrangement 204 in FIG. 4, while their coupling to the IPG corresponds to the dissipation modality 216 of the attenuation arrangement 204 in FIG. 4.

In some examples, the two conductive elements 752A, 752B may be coupled together before being coupled to the housing 762, such as via a common node or connector. Via this arrangement, coupling to the housing 764 of the IPG 760 may be simplified.

In some examples, the IPG housing 762 and/or its header 765 comprises a dedicated port 768 to receive a connector from the conductive elements 752A, 752B to ensure a robust mechanical and electrical coupling of the conductive elements 752A, 752B relative to IPG 760 and therefore relative to the conductive surface 764.

As noted in association with some other examples throughout the present disclosure, it will be understood that the FPE assembly 502 may in some examples extend an entire length (L1 in FIG. 2) of a lead 72 such that the length of elements 752A, 752B is rather small. However, in some examples, the FPE assembly 502 may extend just along a portion of the lead 72 or just along a length of the electrode 102 (FIG. 2) such that the respective conductive elements 752A, 752B may have a relatively large length.

Figure 12:
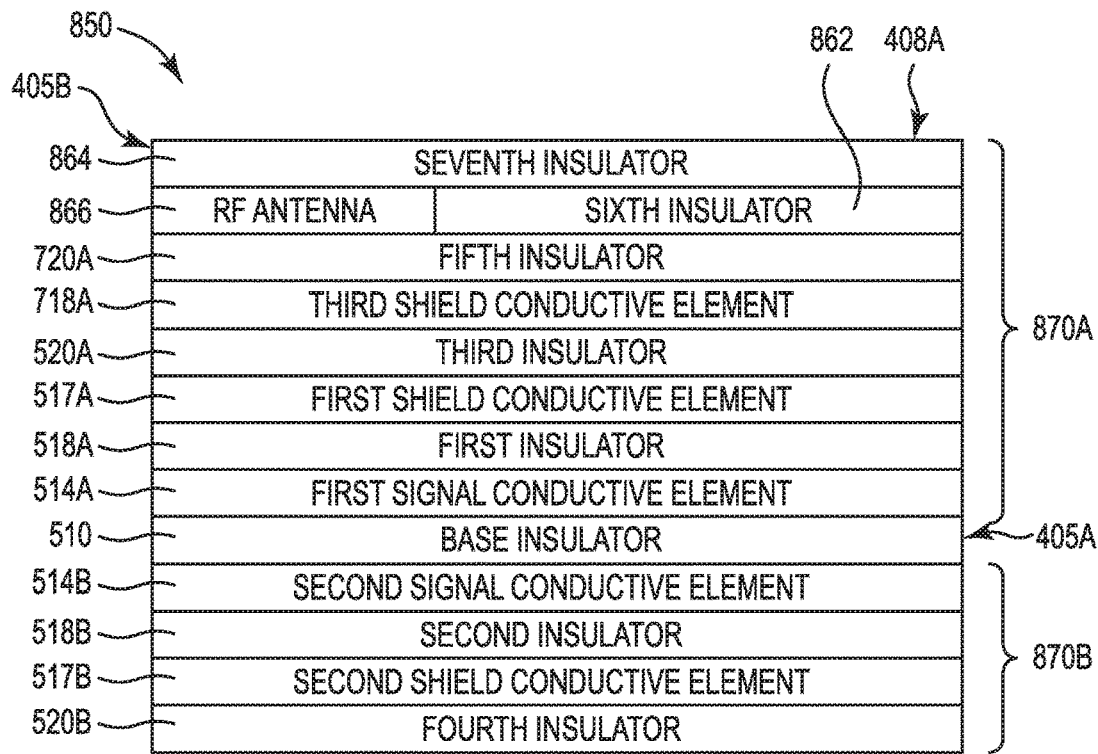
FIG. 12 is a sectional view schematically representing a FPE assembly including an RF antenna, according to one example of the present disclosure.

FIG. 12 is a sectional view schematically representing a FPE assembly 850 (of an implantable medical device IMD 62 in FIG. 1) including a radiofrequency (RF) antenna, according to one example of the present disclosure. In some examples, FPE assembly 850 comprises at least some of substantially the same features and attributes as FPE assembly 700 in FIG. 10, except for further comprising an RF antenna 866. The RF antenna 866 may be used for communicating with other implanted devices and/or to communicate with devices external to the patient's body.

However, in order to maintain sufficient attenuation of MRI-energy relative to the signal conductive elements 514A, 514B, FPE assembly 850 includes additional insulative structures.

Accordingly, in comparison to FPE assembly 700 shown in FIG. 10, the FPE assembly 850 in FIG. 12 includes the same third shield conductive element 718A and fifth insulator 720A but omits fourth shield conductive element 718B and sixth insulator 720B. However, as shown in FIG. 12, the RF antenna 866 is printed on top of the fifth insulator 720A external to the third shield conductive element 718A. In addition, a sixth insulator 862 and a seventh insulator 864 further surround the RF antenna 866. It will be understood from FIG. 12 that, in at least some examples, the sixth insulator 862 and RF antenna 866 represent an arrangement in which the conductive portion of the RF antenna 866 is electrically isolated from surrounding body tissues and/or fluid, and that, in at least some examples, the sixth insulator 862 may not necessarily represent a separate structure from RF antenna 866 and/or from seventh insulator 864 and/or fifth insulator 720A.

Via this arrangement, the FPE assembly 850 is asymmetrical regarding the amount of shielding (per shielding modality 212) on a first portion 870A of FPE assembly 850 than on second portion 870B. In particular the first portion 870A has substantially more shielding and substantially more insulative elements than second portion 870B. In one aspect, this arrangement may help to compensate for the increased coupling for MRI signals that would otherwise be expected due to the presence of RF antenna 866. Accordingly, first portion 870A enhances the attenuation arrangement relative to the signal conductive elements 514A, 514B. In addition, in some examples, the filtering modality (e.g. 214 in FIGS. 5A-5D) may be employed to prevent or minimize interference from MRI RF frequencies.

Figure 13:
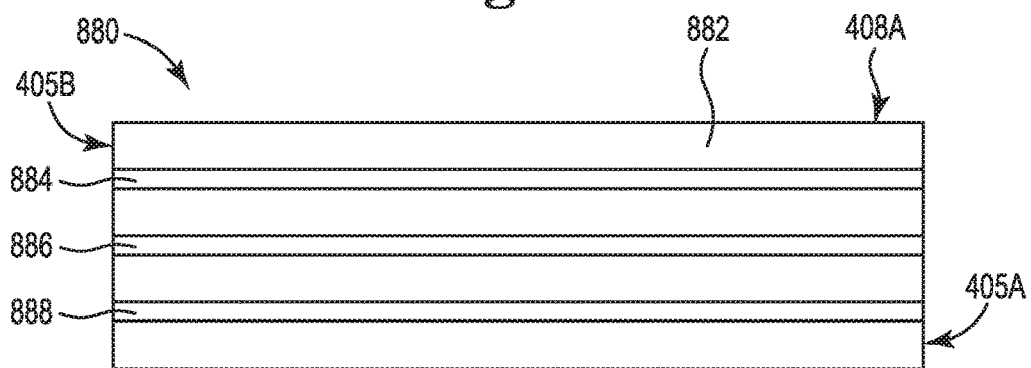
FIG. 13 is a top view schematically representing an array of signal conductive elements in one layer of a FPE assembly, according to one example of the present disclosure.

FIG. 13 is a top view schematically representing a portion 880 of a FPE assembly including at least a layer of separate signal conductive elements 884, 886, 888, according to one example of the present disclosure. In particular, as shown in FIG. 13, three distinct signal conductive elements 884, 886, 888 are printed onto an insulator 882 in a generally coplanar arrangement. In some examples, the insulator 882 corresponds to a base insulator 510 in one of the previously described examples while the three signal conductive elements 884, 886, and 888 may correspond to one or both of the shield conductive elements 517A, 517B.

Each respective signal conductive element 884, 886, 888 carries a separate signal independent of the other respective signal conductive elements 884, 886, 888.

Figure 14:
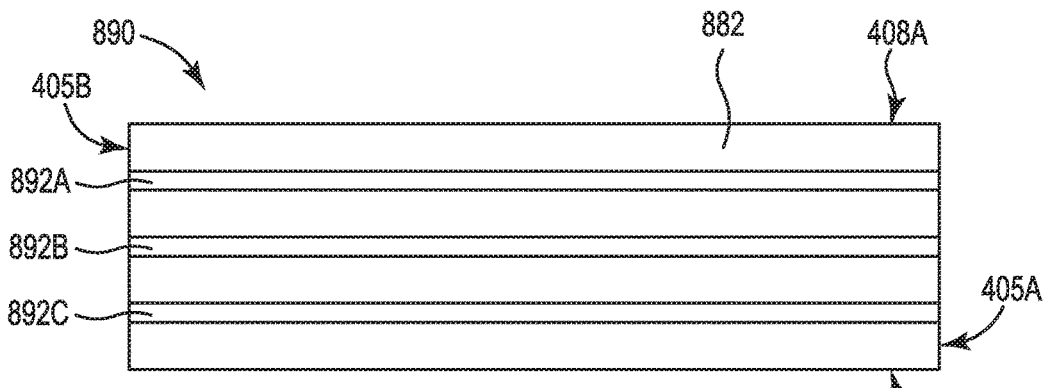
FIG. 14 is a top view schematically representing an array of signal conductive elements in one layer of a FPE assembly, according to one example of the present disclosure.

FIG. 14 is a top view schematically representing a portion 890 of a FPE assembly including at least a layer of separate signal conductive elements 892A, 892B, 892C, according to one example of the present disclosure. As shown in FIG. 14, portion 890 of the FPE assembly comprises substantially the same features and attributes as the portion 880 of the FPE assembly in FIG. 13, except that the three different signal conductive elements 892A, 892B, 892C carry the same signal. Via this arrangement, the same signal is carried via parallel routes to build redundancy into the FPE assembly. Accordingly, in the event that one of the signal conductive elements 892A, 892B, 892C may become inoperable, then two other signal conductive elements of the array already would be carrying the signal.

In some examples, the arrangement in FIG. 13 and/or FIG. 14 may comprise at least some of substantially the same features and attributes as previously described for signal conductive element 514A in association with at least FIG. 7B.

Figure 15:
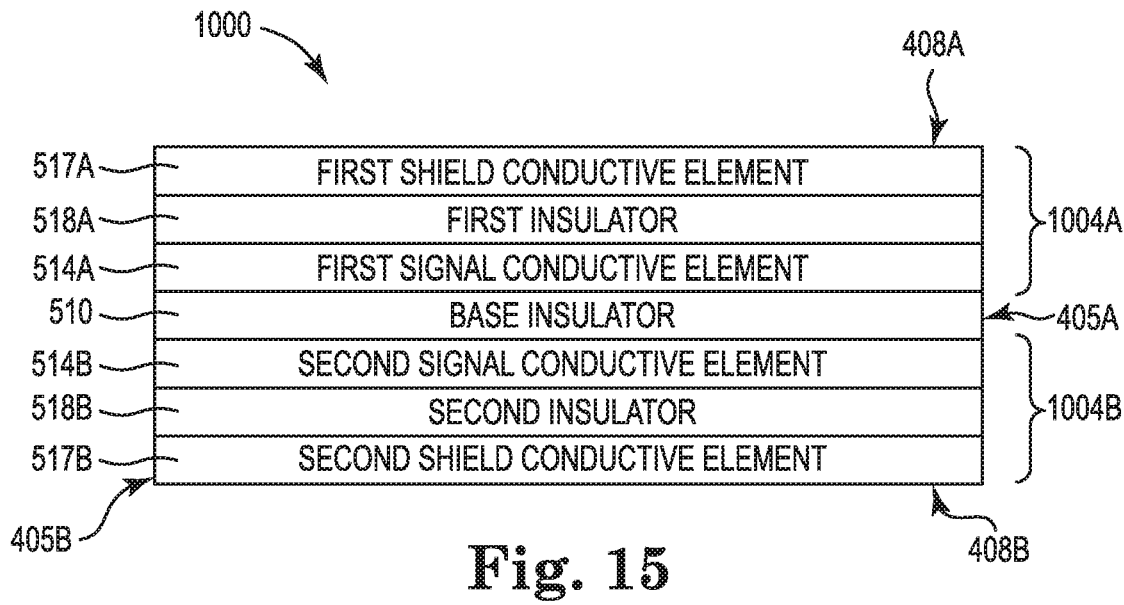
FIG. 15 is a sectional view schematically representing a FPE assembly including an exposed shield conductive element, according to one example of the present disclosure.

FIG. 15 is a sectional view schematically representing a FPE assembly 1000 including exposed shield conductive elements 517A, 517B, according to one example of the present disclosure. In some examples, FPE assembly 1000 comprises at least some of substantially the same features and attributes as FPE assembly 502 in FIG. 7E, except omitting the outermost insulators 520A, 520B such that the shield conductive elements 517A, 517B become exposed. In one respect, via this arrangement a greater exposure of the shield conductive elements 517A, 518B may enhance their ability to attenuate the MRI energy because those elements are directly coupled relative to the surround body tissue, thereby establishing a larger surface area over which the MRI-energy may be shielded and/or dissipated. Accordingly, via this arrangement, continual electrical contact is maintained between the body tissue and the shield conductive elements.

Figure 16:
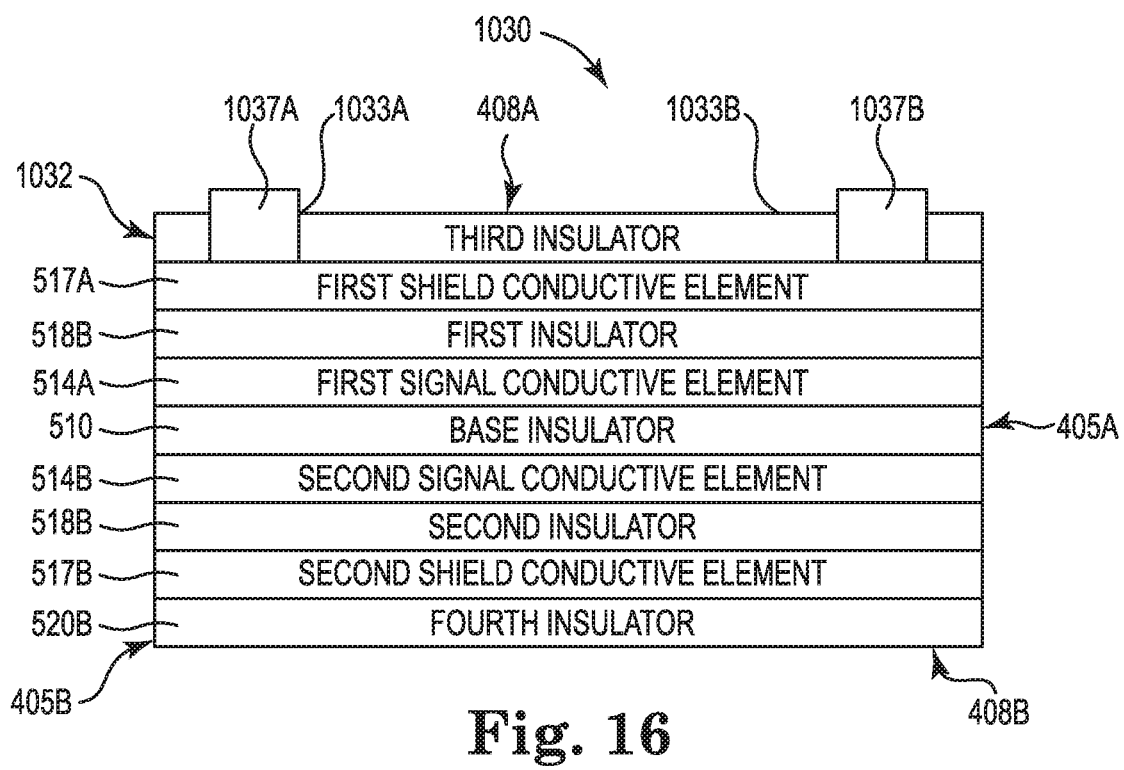
FIG. 16 is a sectional view schematically representing a FPE assembly including exposed vias coupled to a shield conductive element, according to one example of the present disclosure.

FIG. 16 is a sectional view schematically representing a FPE assembly 1030 including at least partially exposed vias 1037B coupled to a shield conductive element 517A, according to one example of the present disclosure. In some examples, FPE assembly 1030 comprises at least some of substantially the same features and attributes as FPE assembly 502 in FIG. 7E, except for modifying the upper outermost insulator (e.g. third insulator 520A) to form third insulator 1032 to accommodate vias 1037A, 1037B. In particular, in some examples the vias 1037A, 1037B are printed onto portions of the first shield conductive element and extend through apertures 1033A, 1033B of the outer-most insulator 520A such that a top surface of the vias 1037A, 1037B become directly exposed to an external environment for direct coupling to surrounding body tissue.

Via this arrangement, an insulator still generally covers the shield conductive element 517A but the vias provide paths by which the shield conductive element 517A can be coupled to the surrounding body tissue to increase the overall surface area over which the MRI-energy is dissipated. At the same time, the shield conductive element 517A (and shield conductive element 517B) attenuates the MRI energy.

Figure 22A:
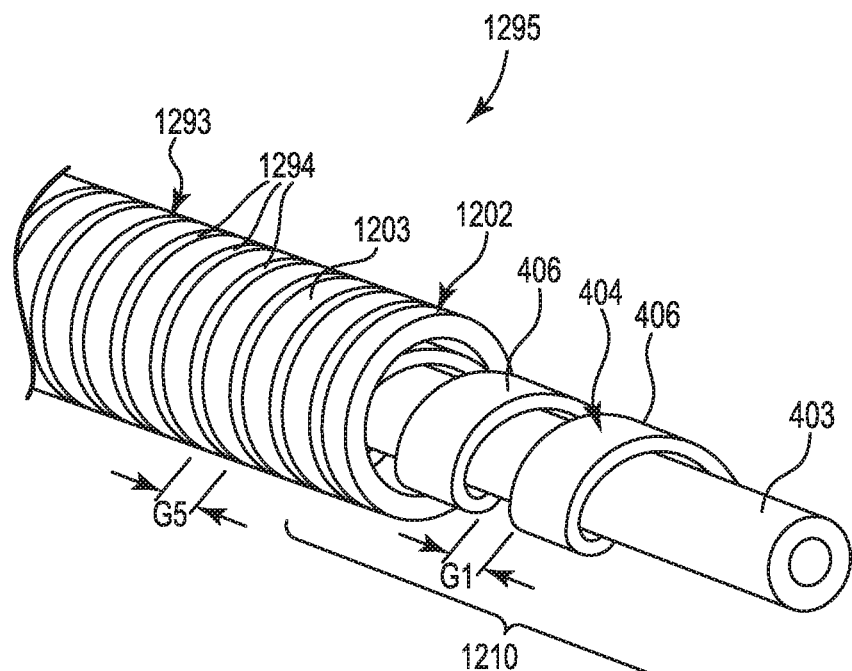
FIG. 22A is a perspective view schematically representing an implantable lead assembly including at least the FPE assembly of FIG. 21A, according to one example of the present disclosure.
Figure 22B:
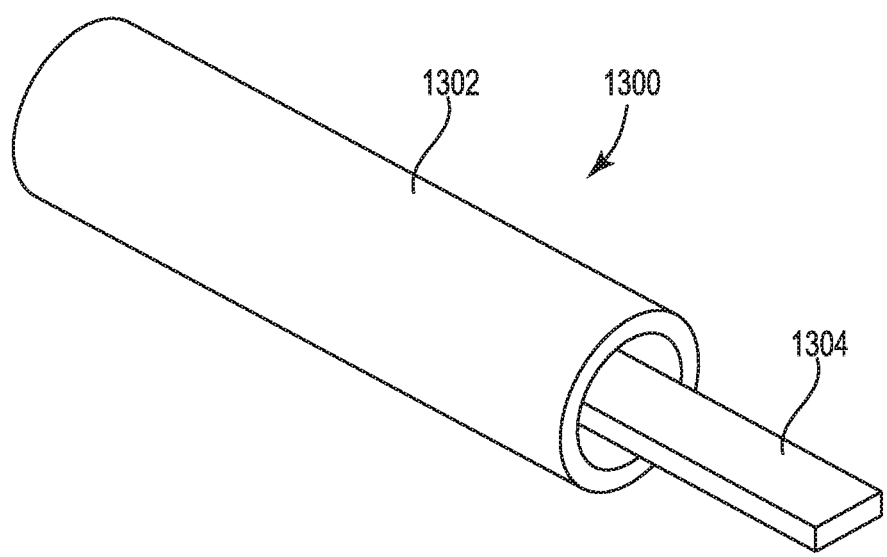
FIG. 22B FIG. is a perspective view schematically representing an implantable lead assembly including a FPE assembly extending within a lumen of an outer flexible tubular insulator, according to one example of the present disclosure.

In some examples, such as but not limited to the lead assembly 1300 of FIG. 22B, even when some conductive elements are exposed on an outer surface of the FPE assembly 1000 (FIG. 15) 1030 (FIG. 16), an outer tubular insulator is provided. In such arrangements, when the insulator 1032 (FIG. 16) is sufficiently thin, the arrangement can enhance the capacitive coupling of the shield conductive element 517A relative to the surrounding tissue, which in turn enhances dissipation of energy at shield conductive element 517A upon receiving MRI-energy, as previously described in association with at least FIG. 7.

With regard to the examples of FIG. 15 or FIG. 16, it will be understood that passive components, such as inductors or capacitors may be implemented as part of or connected to the shield conductive element 517A (FIG. 15) and/or the vias 1033A,1033B (FIG. 16). In one aspect, such arrangements may further enhance capacitive coupling relative to the surrounding body tissue, and thereby enhance energy dissipation from the shield conductive elements into the surrounding body tissue.

With regard to the example arrangements in FIG. 15 or FIG. 16, it will be understood that in some examples the second shield conductive element 517B (and outer insulator 520B in FIG. 16) can be omitted such that shielding functionality is provided on just one side of the respective FPE assemblies 1000, 1030. The asymmetric shielding arrangement in FIG. 7D provides one such example.

FIG. 17A is a top view schematically representing a portion of a FPE assembly 1050, according to one example of the present disclosure. In some examples, as shown in FIG. 17A the FPE assembly 1050 includes an insulator 1052 on which is printed a conductive element 1053 in a mesh pattern 1055. In some examples, the spacing S1 between adjacent struts 1054 of the mesh pattern is at least one order of magnitude less than the wavelength of the MRI-energy field signals (within the body), and in some examples, the spacing S1 is at least two orders of magnitude less than such wavelengths. In one aspect, this arrangement corresponds to at least the shield modality 212 and/or shield modality 210 in the attenuation arrangement 204 of FIG. 2. In some examples, via its mesh pattern 1055, the conductive element 1054 provides one example implementation of at least a respective one of the shield conductive elements 517A, 517B (or 718A in FIG. 12). It will be understood that FIG. 17A provides generous spacing between adjacent struts 1054 for illustrative purposes, but that an actual mesh would have an appearance of much closer spacing between adjacent struts 1054.

In some examples, the arrangement of the conductive element 1054 can be used as a signal conductive element, such as signal conductive element 514A and/or 514B (FIG. 7), instead of being used as shield conductive element (e.g. 517A, 517B). In such arrangements, the mesh pattern 1055 is defined by a single conductive element, wherein the mesh pattern 1055 provides a form of redundancy via the multiple pathways by which a signal may travel along the multiple different conductive struts 1054 of the mesh pattern 1055. Accordingly, this arrangement can mitigate fatigue of the conductive elements which may potentially arise due to flexing of the FPE assembly within the body, which may occur during initial implantation or during long term use.

Figure 17B:
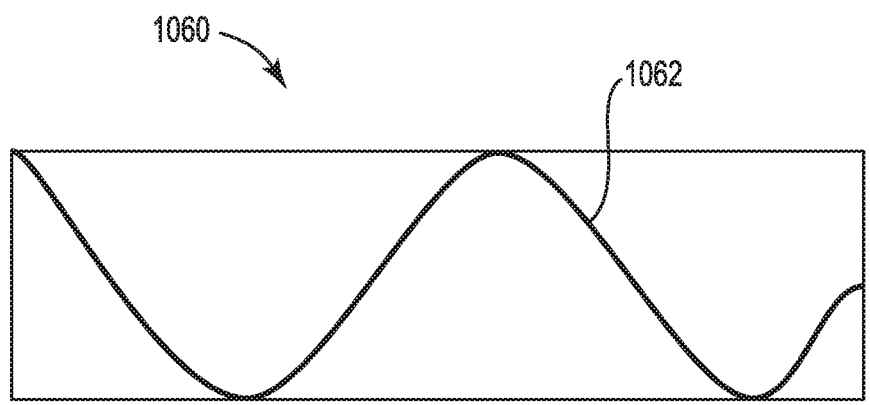
FIG. 17B is a top view schematically representing a FPE assembly including a signal conductive element arranged in a curved pattern, according to one example of the present disclosure.

FIG. 17B is a top view schematically representing a conductive element 1062 of a FPE assembly 1060, according to one example of the present disclosure. In some examples, the conductive element 1062 is arranged in a generally curved shape (e.g. sinusoidal) to minimize stress concentrations, which in turn may minimize crack propagation due to flexing of the lead assembly in the patient's body. In this way, the configuration of the conductive element potentially maximizes longevity of the conductive elements. In one aspect, the curved shape of the conductive element also can contribute to enhanced general flexibility of the FPE assembly 1060, as compared to other examples of an FPE assembly, which may (or may not) have arrangements of conductive elements exhibiting less flexibility. In some examples, when used as a signal conductive element, this structure may provide enhanced filtering relative to a linear conductor by virtue of the increased RF impedance of the conductor.

In some examples, such curved shapes may be implemented in a mesh configuration as described in association with FIG. 17A.

FIG. 18A is a block diagram 1100 schematically representing a lead assembly 1102 including an associated attenuation arrangement, according to one example of the present disclosure. In some examples, the lead assembly 1102 comprises a FPE region 1130 and a non-FPE region 1132 with dashed lines 1133 representing a boundary between the two respective regions 1130, 1132. The non-FPE region 1132 is co-extensive with the electrode portion 1122 and indicates that the portion of the lead assembly 1102 in non-FPE region 1132 is constructed via elements and techniques other than a FPE assembly (FIGS. 6A-17B). Meanwhile, the FPE region 1130 is co-extensive with the lead 1112 and active element 1125 and indicates that the portion of the lead assembly 1102 in region 1130 is at least partially defined by a FPE assembly. In some examples, such an FPE assembly may comprise at least some of substantially the same features and attributes as at least some of the FPE assemblies as previously described in association with at least FIGS. 2, 5A-17B, and 19-33. Accordingly, in some examples, in addition to active attenuation element 1125, the lead 1112 includes one or several attenuation modalities (at least 212, 214, 216, 217 in FIG. 5A).

As shown in FIG. 18A, lead 1112 extend between a proximal end 1115 and a distal end 1113 with active element 1125 at the distal end 1113 such that active element 1125 is interposed between the more proximal portions of lead 1112 and the non-FPE region 1132 of the lead assembly 1102. Among other potential components, lead 1112 includes at least a pair of signal conductive elements 1141, 1142 (e.g. 514A, 514B in FIG. 7) extending from proximal end 1115 to a position just short of the distal end 1113 at which the signal conductive elements are electrically and physically coupled to a proximal end 1127B of the active element 1125. Meanwhile, at its distal end 1127A the active element 1125 is physically and electrically coupled to the electrode portion 1122 via conductive elements 1151A, 1151B, 1153C to control contact electrodes E.

It will be understood that the number of conductive elements (e.g. 1141, 1142) in lead 1112 and the number of conductive elements (e.g. 1151A, 1151B, 1151C) in the non-FPE region 1132 may vary from the number shown in FIG. 18A.

In some examples, the active element 1125 may comprise a RF choke or active element that is normally open, but which may receive a signal from an IPG (e.g. 104 in FIG. 2) to isolate the lead 1112 from the electrodes E in electrode portion 1122.

In some examples, the active element 1125 may include circuitry to receive signals from the lead 1112 and process them before transmitting control signals to apply stimulation signal to electrodes E in a desired pattern to implement a stimulation therapy regimen via electrode portion 1122.

In addition, the active element 1125 electrically and physically isolates the conductive elements 1141, 1142 extending throughout the length of lead 1112 from the contact electrodes E in the electrode portion 1122. By doing so, the active element 1125 prevents the RF energy (that may become coupled to the much longer conductive elements 1141, 1142 of the lead 1112) from reaching the electrodes E, and thereby minimizes heating at electrodes E.

In this regard, it will be further noted that the conductive elements 1151A, 1151B, 1151C have a relatively short length (L4). In some examples, this length L4 is least one or two orders of magnitude less than a length L5 of the conductive elements 1141, 1142 of the lead 1112 and at least one or two orders of magnitude less than a wavelength of the MRI signals (within the body). Accordingly, given their relatively short length, it may be expected that a relatively small amount of RF energy could couple onto those conductive elements 1151A, 1151B, 1151C, and therefore an insignificant amount of heating may result. In some examples, the length L4 may be in the range of less than 5 centimeters.

Accordingly, because the conductive elements 1151A-1151C in the non-FPE region 1132 are relatively short and are electrically isolated from the relatively long conductive elements 1141, 1142 in lead 1112, this arrangement inhibits large amounts of MRI RF energy from becoming coupled onto conductive elements 1151A-1151C. This arrangement thereby also inhibits large amounts of MRI RF energy from becoming coupled onto electrodes E in electrode portion 1122.

In some examples, a combination of the electrodes E and the conductive elements 1151A, 1151B, 1151C have a relatively short length (L10) relative to the entire lead 1112. In some examples, this length L10 is least one or two orders of magnitude less than a length L5 of the conductive elements 1141, 1142 of the lead 1112 and at least one or two orders of magnitude less than a wavelength of the MRI signals (within the body). Accordingly, given this relatively short length, it may be expected that a relatively small amount of RF energy could couple onto those conductive elements 1151A, 1151B, 1151C and/or electrodes E, and therefore an insignificant amount of heating may result. In some examples, the length L10 may be in the range of less than 10 centimeters. In some examples, the length L10 may less than about 2 centimeters.

It will be understood that, in some examples the lead assembly 1102 can include other attenuation modalities embodied in the FPE assembly which at least partially defines the lead 1112, with such attenuation modalities (e.g. 210-217) being described in association with at least some of the examples in FIGS. 5A-33. Moreover, in some examples, the non-FPE region 1132 also can include some attenuation modalities, such as an external shield, some of which are described throughout at least some of examples throughout the present disclosure.

FIG. 18B is a block diagram 1150 schematically representing a lead assembly 1152 including an associated attenuation arrangement, according to one example of the present disclosure. As shown in FIG. 18B, in some examples substantially the entire length of the lead assembly 1152 is at least partially defined by a FPE assembly 1153, which comprises at least some of substantially the same features and attributes as at least some of the FPE assemblies as described in association with at least FIGS. 2, 5A-17B, and 19-33. As shown in FIG. 18B, in some examples an entire length of the lead assembly 1152 is defined by such a FPE assembly 1153.

Accordingly, as shown in FIG. 18B, even the region 1145 (dashed box) in which electrode portion 1157 is located is defined by an FPE assembly 1153. Stated differently, the FPE assembly 1153 is co-extensive with the electrode portion 1157 as well as with the lead 1142 proximal to the electrode portion 1157.

Figures 18C, 18D:
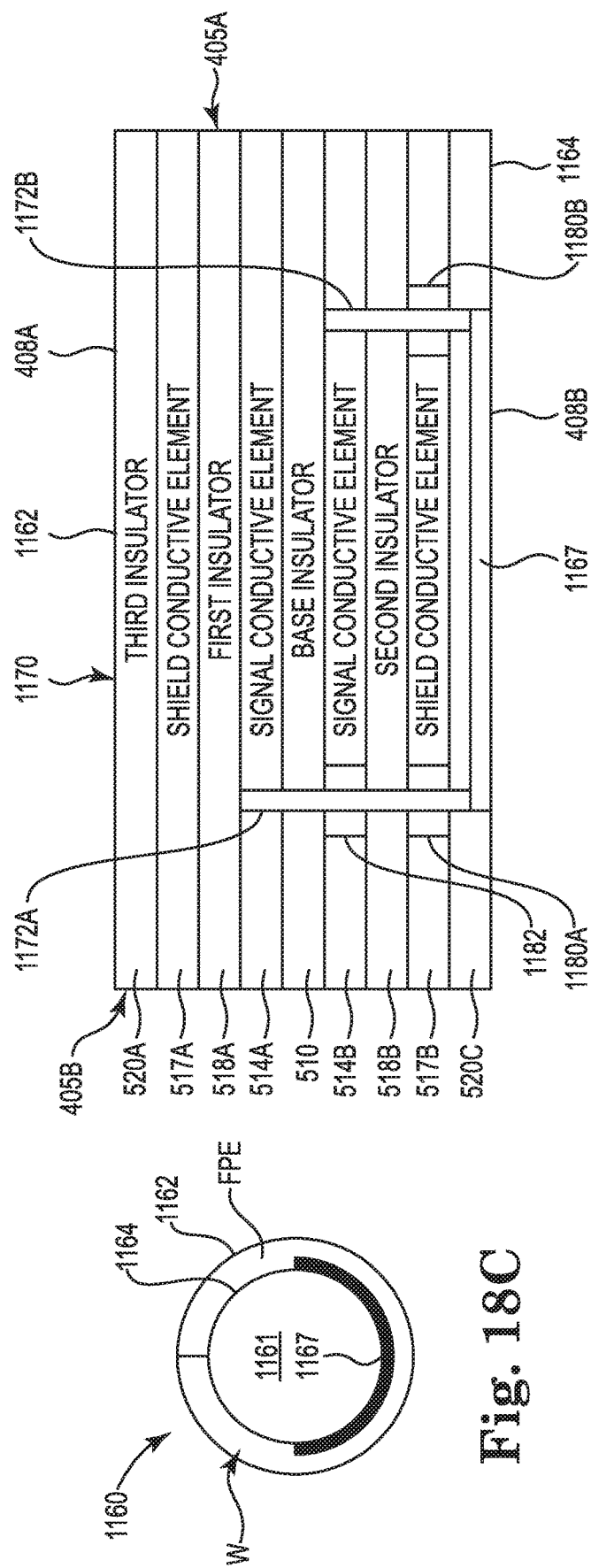
FIG. 18C is a sectional view of FIG. 18B as taken along lines 18C-18C and schematically representing a cuff electrode, according to one example of the present disclosure.
FIG. 18D is a sectional view schematically representing a FPE assembly including a contact electrode, according to one example of the present disclosure.

FIG. 18C is a sectional view of FIG. 18B as taken along lines 18C-18C and schematically representing a cuff electrode 1160 defined by a FPE assembly, according to one example of the present disclosure. As shown in FIG. 18C, cuff electrode 1160 comprises a generally circular cross-sectional shape having an outer surface 1162 and an inner surface 1164 defining a lumen 1161 sized for releasable engagement about a nerve or other body tissue. In some examples, the wall W of the cuff electrode 1160 is defined by a FPE structure (e.g. FPE assembly 1170 in FIG. 18D). In some examples the FPE structure comprises substantially the same features and attributes as the FPE assembly defining the lead assembly 1152. In some examples, the FPE structure defining the cuff electrode 1160 at least some features and attributes other than those of FPE assembly defining the lead assembly 1152.

In addition, in some examples, the electrode portion 1157 of lead assembly 1152 in FIG. 18B is embodied in a configuration other than a cuff electrode, and as such, can be a paddle electrode, etc.

As shown in FIG. 18C, a contact electrode 1167 extends along at least a portion of the inner surface 1164 of the cuff electrode 1160.

In some examples, the FPE structure defining the wall of the cuff electrode or defining the lead body may take the form shown in FIG. 18D. Accordingly, FIG. 18D is a sectional view schematically representing a FPE assembly 1170, according to one example of the present disclosure.

As shown in FIG. 18D, the FPE assembly 1170 comprises substantially the same features and attributes as FPE assembly 502 in FIG. 7E, except further comprising a contact electrode 1167. In some examples, the contact electrode 1167 may be used to transmit a stimulation signal to a body tissue, sense physiologic information from a body tissue, and/or for other purposes.

In some examples, the contact electrode 1167 is embedded within insulator 520C. In some examples, vias 1172A, 1172B extend internally and vertically from contact electrode 1167 to be electrically coupled relative to one or both of the signal conductive elements 514A, 514B. In some examples, an insulative region 1180A, 1180B electrically isolates the conductive vias 1172A, 1172B from the shield conductive element (e.g. layer) 517B. In some examples, when appropriate based on the type of signals being transmitted and/or received, an insulative region 1182 is provided to electrically isolate the conductive via 1172A from signal conductive element 514B.

In some examples, because the contact electrode 1167 is located on a bottom surface 408B of the FPE assembly 1170, which also defines the inner surface 1164 of the cuff electrode 1160, the contact electrode 1167 is generally shielded by the other shielding elements 517A, 517B of the FPE assembly 1170.

Accordingly, the contact electrode, signal conductive elements, and shielding functionality can be incorporated into a monolithic structure (e.g. a single unitary piece) defined by a FPE assembly.

Figure 18E:
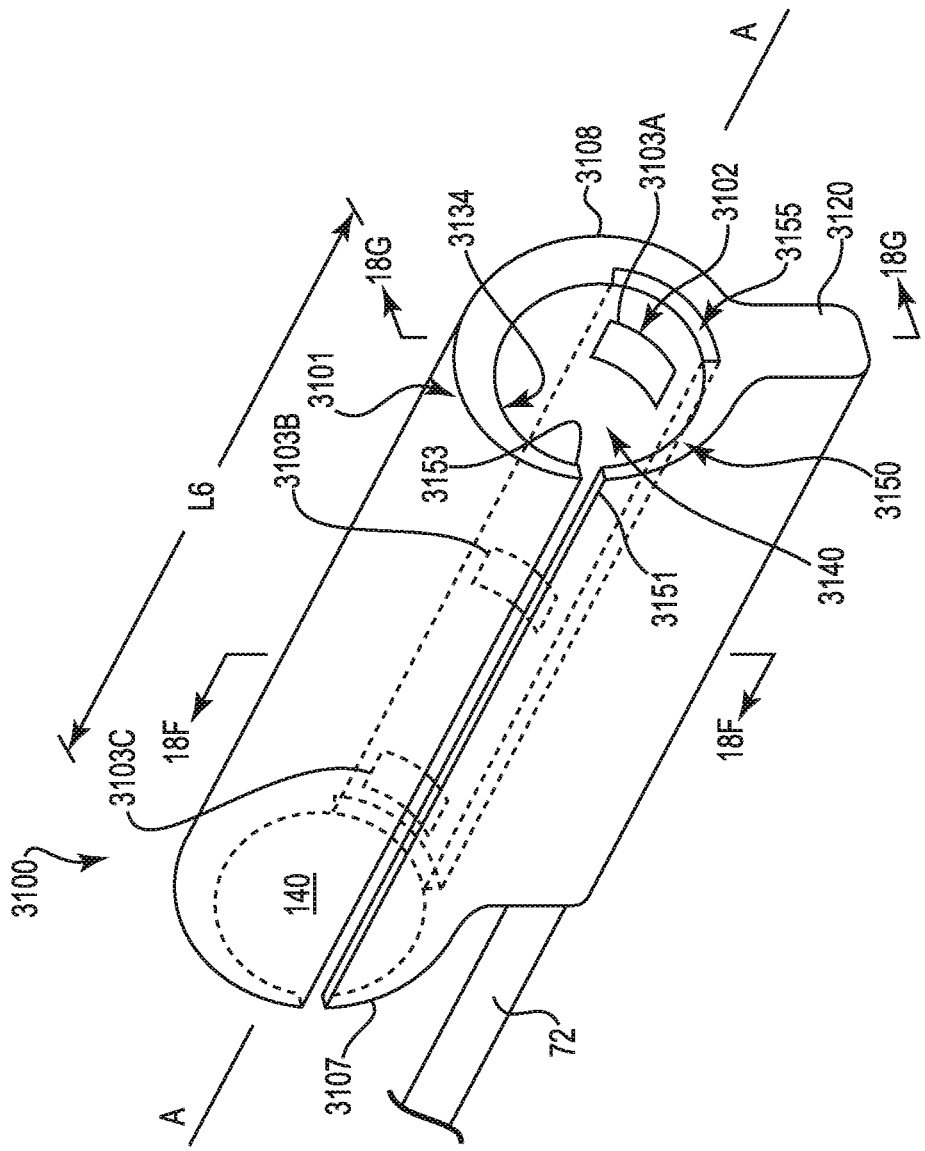
FIG. 18E is an isometric view schematically representing a cuff electrode incorporating a FPE assembly, according to one example of the present disclosure.
Figure 18K:
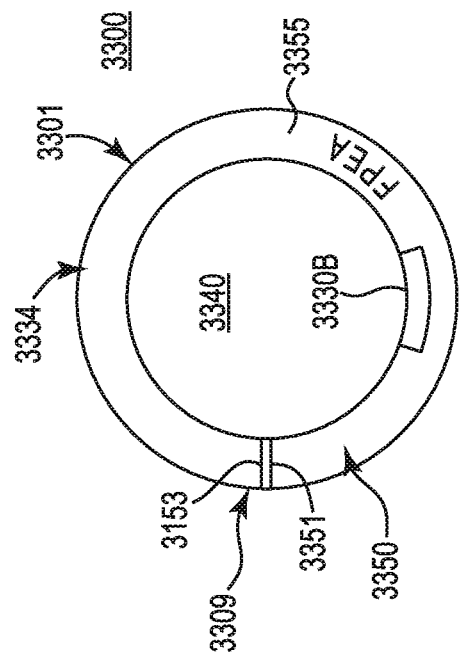
FIG. 18K is a sectional view as taken along lines 18K-18K of FIG. 18J and schematically representing a FPE assembly formed as a cuff electrode, according to one example of the present disclosure.
Figure 18M:
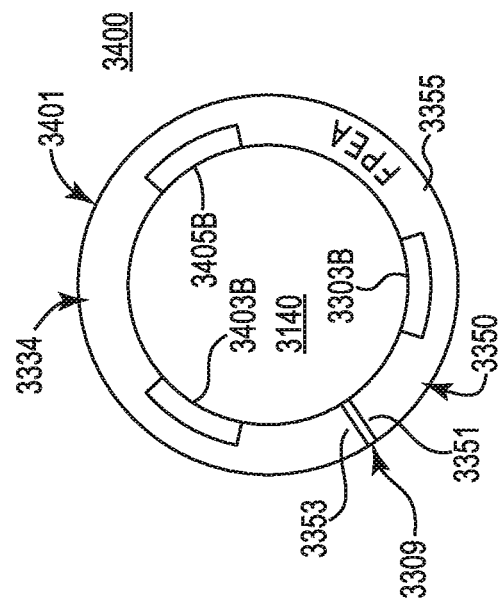
FIG. 18M is a sectional view as taken along lines 18M-18M of FIG. 18L and schematically representing a FPE assembly formed as a cuff electrode, according to one example of the present disclosure.
Figure 18J:
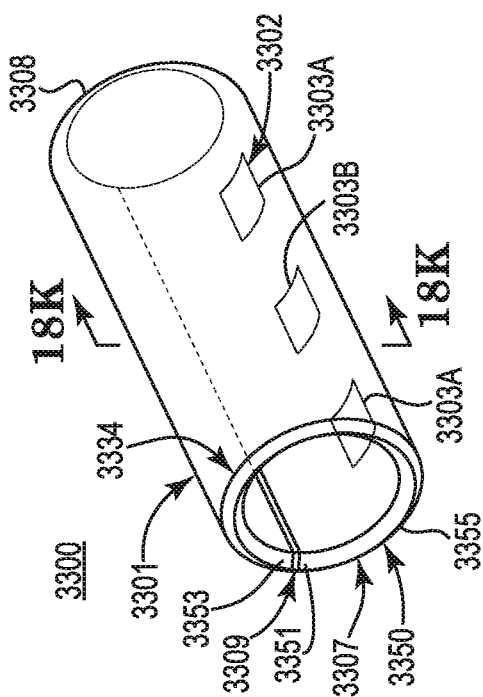
FIG. 18J is an isometric view schematically representing a FPE assembly formed as a cuff electrode, according to one example of the present disclosure.
Figure 18L:
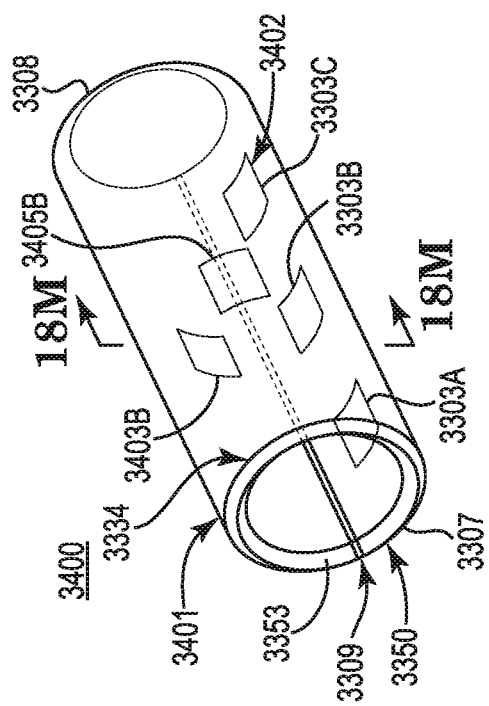
FIG. 18L is an isometric view schematically representing a FPE assembly formed as a cuff electrode, according to one example of the present disclosure.
Figure 18O:
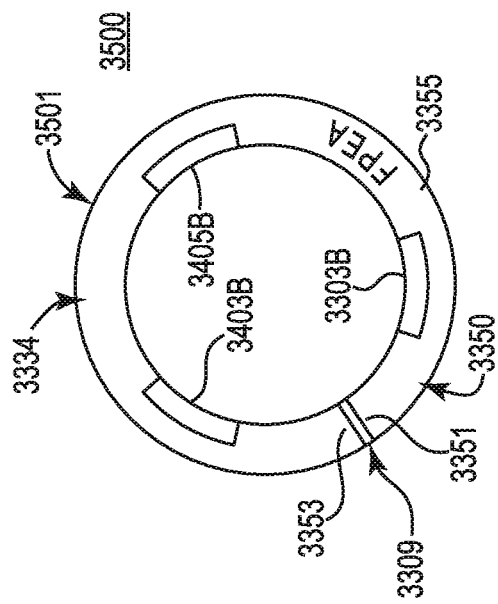
FIG. 18O is a sectional view as taken along lines 18O-18O of FIG. 18N and schematically representing a FPE assembly formed as a cuff electrode, according to one example of the present disclosure.
Figure 18N:
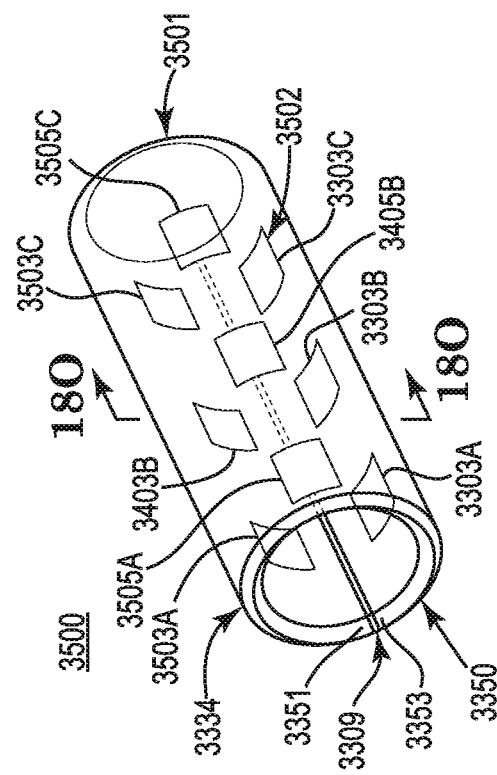
FIG. 18N is an isometric view schematically representing a FPE assembly formed as a cuff electrode, according to one example of the present disclosure.

In some examples, the electrode portion 1157 of lead assembly 1852 in FIG. 18B may comprise a cuff electrode arrangement having at least some of the features and attributes as cuff electrode 3100 in FIGS. 18E-18G, cuff electrode 3200 in FIGS. 18H-18I, cuff electrode 3300 in FIGS. 18J-18K, cuff electrode 3400 in FIGS. 18L-18M, and/or cuff electrode 3500 in FIGS. 18N-18O.

With this in mind, FIG. 18E is an isometric view of a cuff electrode 3100 which may serve as one implementation of electrode portion 1157 in FIG. 18B and/or electrode 102 (FIG. 2). As shown in FIG. 18E, cuff electrode 3100 comprises a cuff body 3101 defining a lumen 3140 via at least opposing, resilient flange members 3134 and 3150, which are each shaped, sized, and biased to cause their respective ends 3151 and 3153 to releasably contact each other (or nearly contact each other) at 3109. Via this arrangement, the cuff body 3101 may be self-sizing for differently sized nerves and/or to accommodate nerve swelling. An array 3102 of electrodes 3103A-3103C are spaced apart along a length (L6) of cuff body 3101 between ends 3107, 3108.

In some examples, cuff body 3101 may comprise a base 3120 which may contain electrical conductors for connecting lead 72 to the electrodes 3103A-3103C and/or to at least partially house elements which mechanically support electrodes 3103A-3103C.

In some examples, the electrodes 3103A-3103C form part of a flexible printed electronics (FPE) assembly 3155 such as FPE assembly 1170 (FIG. 18D). In at least one such arrangement, each electrode 3103A-3103C may comprise one example of a respective contact electrode 1167 in FIGS. 18C-18D. In some examples, FPE assembly 3155 in FIG. 18E may have a greater number or fewer number of conductors, insulators, and/or shield elements shown in FIG. 18D. Moreover, in some examples, FPE assembly 3155 also may implement at least one of the attenuation modalities, such as the filter, anti-phase, dissipation, shield modalities as described in association with at least FIGS. 5A-5D and elsewhere throughout examples of the present disclosure.

However, it will be understood that in some examples, FPE assembly 3155 does not define the entire cuff body 3101. Rather, cuff body 3101 is molded or otherwise formed to incorporate FPE assembly 3155 (including electrodes 3103A-3103C). In some examples, electrodes 3103A-3103C may be formed via a non-FPE structure and then electrically and mechanically attached to the FPE assembly 3155. However, in some examples, electrodes 3103A-3103C may be formed as part of and/or incorporated within the FPE assembly 3155. In some examples, FPE assembly 3155 may be considered to be integral with the rest of cuff body 3101.

In some examples, at least those portions of the electrodes 3103A-3103C and/or of the FPE assembly 3155, which may be exposed to contact with bodily tissues and/or fluids, are made of biocompatible material and/or coated with a biocompatible material. In some examples, the biomaterial comprises a platinum/iridium material or a platinum black-based material.

As further shown in the sectional view of FIG. 18F, in some examples, cuff body 3101 may comprise at least one resilient flange member 3160 biased to at least partially overlap flange members 3150, 3134 and the point of releasable contact 3109, thereby further defining lumen 3140 and providing for more robust releasable engagement about a nerve within lumen 3140. Meanwhile, FIG. 18G provides another sectional view of the cuff electrode 3100 illustrating the electrodes 3103A-3103C spaced apart longitudinally along cuff body 3101.

FIG. 18H is an isometric view schematically representing an example cuff electrode 3200 which comprises at least substantially the same features and attributes as cuff electrode 3100 (FIGS. 18E-18G), except with cuff body 3201 omitting a base like base 3120 in FIG. 18E. Instead, cuff body 3200 comprises a base 3220 which generally conforms to a generally uniform contour of the external surface 3223 of cuff body 3200. Like cuff electrode 3100, cuff electrode 3200 incorporates a FPE assembly 3155 as previously described in association with cuff electrode 3100. In some examples, the presence of the FPE assembly 3155 in cuff electrode 3200 may contribute to the omission of base 3120 (FIGS. 18E-18G) at least because FPE assembly 3155 already comprises signal conductors which were formerly conveyed to the electrodes 3103A-3103C via base 3120. Moreover, as previously mentioned in association with FIGS. 18E-18G, the FPE assembly 3155 in cuff electrode 3200 may incorporate various attenuation tools previously described in FIGS. 5A-5D and elsewhere throughout examples of the present disclosure.

As shown in FIG. 18I, in some examples, a third flange member 3260 (like 3160 in FIG. 18F) extends from, and is part of, flange member 3250. In some examples, a shelf 3251 is defined at junction of third flange member 3260 and flange member 3250 with shelf 3251 comprising an end of flange member 3250 at which releasable engagement of end 3153 of flange 3134 may take place.

FIG. 18J is an isometric view schematically representing another example cuff electrode 3300 which may be one implementation of the electrode portion 1157 in FIG. 18B to provide an array 3302 of electrodes 3303A-3303C longitudinally spaced apart between ends 3307 and 3308. In some examples, cuff electrode 3300 may be formed entirely or substantially entirely of a FPE assembly 3355, such as but not limited to FPE assembly 1170 in FIGS. 18C-18D. In such an arrangement, each electrode 3303A-3303C comprises a contact electrode 1167 of FPE assembly 1170 in FIGS. 18C-18D. In some examples, FPE assembly 3355 may comprise a greater or fewer number of the respective insulators, conductors, shield elements, etc. of FPE assembly 1170, as well as various elements to implement at least one of the filter, dissipation, shielding, and anti-phase modalities of the attenuation tools in FIGS. 5A-5D. FIG. 18K is a sectional view further illustrating one example arrangement of cuff body 3301 formed via FPE assembly 3355.

In some examples, additional flange members such as overlapping flange member 3260 (FIG. 18H-18I) may be formed as part of FPE assembly 3355 or overmolded onto FPE assembly 3355 so as to provide for releasable engagement and overlap relative to cuff body 3301, including point 3309 of releasable engagement of opposing ends 3353, 3351 of resilient arms 3334, 3335 of cuff body 3301.

FIGS. 18L-18M schematically represent a cuff electrode 3400, which provides another example implementation of the electrode portion 1157 in FIG. 18B, which may be formed as part of a FPE assembly 1153 (FIG. 18B), 1170 (FIG. 18D). Cuff electrode 3400 comprises at least substantially the same features as cuff electrode 3300 except further comprising additional electrodes 3403B, 3405B such that electrodes 3303B, 3403B, 3405B are arranged in a spaced apart circumferential pattern about cuff body 3401 as shown in FIG. 18L and the sectional view of FIG. 18M. Among other features, this arrangement may enable selective stimulation within and/or along a nerve via the independently activatable/programmable electrodes 3303A, 3303B, 3303C, 3403B, 3405B to achieve different selectable stimulation vectors.

FIGS. 18N-18O schematically represent a cuff electrode 3500, which provides another example implementation of the electrode portion 1157 in FIG. 18B, which may be formed as part of a FPE assembly 1153 (FIG. 18B), 1170 (FIG. 18D). Cuff electrode 3500 comprises at least substantially the same features as cuff electrode 3400 except further comprising additional electrodes 3503A, 3505A, 3503C, 3505C such that all of the respective electrodes on cuff body 3501 are arranged in a spaced apart circumferential pattern and/or spaced apart longitudinal pattern on cuff body 3501 as shown in FIG. 18N and the sectional view of FIG. 18O. Among other features, this arrangement may enable selective stimulation within and/or along a nerve via the independently activatable/programmable electrodes 3303A, 3303B, 3303C, 3403B, 3405B, 3503A, 3505A, 3503C, 3505C to achieve different selectable stimulation vectors.

FIG. 19A schematically represents at least some aspects of an attenuation arrangement 3610 for a lead 3600 and FIG. 19B is a partial sectional view of FIG. 19A, according to one example of the present disclosure. In some examples, lead 3600 may comprise at least some of substantially the same features and attributes as any one of the leads (and/or implantable medical devices) described in association with at least FIGS. 1-18O. In some examples, the attenuation arrangement 3610 may comprise one example implementation of at least the anti-phase modality 217 and/or anti-phase elements 253 in FIGS. 5A-5D. In some examples, the attenuation arrangement 3610 may serve to implement a combination of the at least the various modalities 212, 214, 216, 217 (FIG. 5A).

In some examples, FIG. 19A schematically represents a top view of lead 3600 demonstrating an attenuation arrangement 3610 extending longitudinally (along orientation F) along a length of lead 3600 and/or extending laterally (along orientation S) across a width of lead 3600. Moreover, it will be understood that in some examples the attenuation arrangement 3610 is incorporated within a non-conductive body 3603 of lead 3600, such that attenuation arrangement 3610 may be located just below an exterior surface of lead 3600. In some examples, FIG. 19A represents a top view of lead 3600 such that the portion of attenuation arrangement 3610 depicted in FIG. 19A would correspond to the attenuation arrangement 3610 generally extending over an entire top portion of lead 3600.

In some examples, the attenuation arrangement 3610 extends about an entire periphery of the lead 3600 to completely surround signal conductors and/or other elements within an interior of the lead 3600. Accordingly, the view in FIG. 19A may also schematically represent a bottom view, side view, etc. of lead 3600 and attenuation arrangement 3610 positioned near a bottom, side, etc. of lead 3600, respectively.

As further shown in FIG. 19A, in some examples attenuation arrangement 3610 comprises several rows 3620A, 3620B, 3620C, with each respective row comprising a plurality of conductive loops 3622 aligned generally parallel to a longitudinal axis of lead 3600 (along orientation F). In some examples, the respective conductive loops 3622 are joined together via straight conductive segments 3623 such that the conductive loops 3622 in a given row may comprise a continuous conductive element in some examples. In some examples, each row 3620A-3620C has length substantially the same as a length of lead 3600.

In some examples, the respective loops 3622 are spaced apart from each other both longitudinally and laterally. In some examples, each loop 3622 has a depth as shown in the sectional view of FIG. 19B corresponding to a single loop of conductive material before a straight segment 3623 provides a transition to an adjacent loop 3622 along the length or across the width of the lead 3600.

In some examples, the consecutive pattern of loops 3622 may be understood to proceed in a forward direction from one end of the attenuation arrangement (and therefore of lead 3600) to an opposite end of the attenuation arrangement (and therefore of lead 3600) by which the signal is pathway proceeds longitudinally forward. In some such examples, the continuous pattern of consecutive loops 3622 within a given row (e.g. 3630A, 3630B, 3630C) do not reverse course in an opposite direction and/or do not reverse course in an opposite direction in any significant way before resuming a forward direction again.

In some examples, the loop 3622 may be considered as providing an inductive effect with rows of loops 3622 (in the longitudinal and/or lateral orientation) thereby acting to dissipate RF energy from an external source, such as an MRI or other RF source. In particular, such an arrangement of loops 3622 may provide an anti-phase modality 217 (FIGS. 5A-5D) to effectively cancel RF energy which may otherwise propagate as e-fields along a length of lead 3600.

In some such examples, because the attenuation arrangement 3610 does not comprise a signal conductor, a continuous portion of a conductor which defines a given row (e.g. 3630A) of conductive loops 3622 may have ends which terminate without connection to an electrode or electrical contact. Stated differently, in at least some examples, each conductor(s) forming each respective row of conductive loops may sometimes be referred to as a non-signal conductor. In this way, in some instances the attenuation arrangement 3610 may be understood as being separate from, and independent of, any electrodes and/or electrical contacts to which a separate signal conductor is connected.

In some examples, a substrate (e.g. base insulator 508 in FIG. 7A, 510 in at least FIG. 7B) onto which loops 3622 are formed or printed does not reverse direction between the ends of the substrate, but rather extends in a single, forward direction.

However, in some examples, each conductive loop 3622 depicted in the view of FIG. 19A may comprise a plurality 3662 of spaced apart loops 3622 extending a greater depth, as shown in the sectional view of FIG. 19C, before a straight segment 3623 provides a transition to an adjacent loop 3622 along the length or across the width of the lead 3600.

In such arrangements, the plurality of loops 3625 extending for a depth at each position of the (main) loop 3622 may enhance the anti-phase and/or inductive influence on RF energy directed at the lead 3600.

It will be understood that in at least some examples, the rows 3620A, 3620B, 3620C of conductive loops of attenuation arrangement 3610 do not serve as signal conductors. In some examples, the rows of conductive loops of attenuation arrangement are independent of (e.g. not connected to) an electrode used for sensing and/or stimulation. Rather, instead the lead comprising the attenuation arrangement 3610 comprises other conductive elements which may serve as signal conductors.

FIG. 19D is a sectional view schematically representing at least some aspects of an attenuation arrangement 3680, according to one example of the present disclosure. In some examples, the attenuation arrangement 3680 comprises at least some of substantially the same features and attributes as attenuation arrangement 3660 (FIG. 19C), except including at least one capacitive structure 3682 among rows of pluralities 3625 of conductive loops 3622, which may act as inductive structures. In one aspect, the presence of at least some capacitive structures among the pluralities 3625 of conductive loops 3622 may contribute to the shield, filter, dissipation, and/or anti-phase modalities 212, 214, 216, 217 (FIGS. 5A-5D).

FIG. 19E schematically represents an attenuation arrangement 3690 comprising at least one row 3691 of generally rectangular-shaped conductive loops 3692, according to one example of the present disclosure. In some examples, attenuation arrangement 3690 comprises at least some of substantially the same features and attributes as at least one of the attenuation arrangements 3610, 3660, 3680 as described in association with at least FIGS. 19A-19D, except with conductive loops 3692 having a generally rectangular shape. In some examples, the respective straight segments 3693 connect adjacent loops 3692. In some examples, as compared to the generally circular-shaped loops described above, the generally rectangular shaped loops 3692 are more amenable to construction in an FPE assembly.

FIG. 19F schematically represents an attenuation arrangement 3700 comprising a row 3701 of overlapping circular-shaped conductive loops 3702 according to one example of the present disclosure. In some examples, attenuation arrangement 3700 comprises at least some of substantially the same features and attributes as at least one of the attenuation arrangements 3610, 3660, 3680 as described in association with at least FIG. 19A, except with conductive loops 3702 overlapping each other. Straight segments 3703 connect the loops 3702 together. Via such overlap, in some examples this arrangement may more efficiently dissipate local RF energy along the lead body at the stimulation electrode and/or provide a greater inductance and therefore enhanced filtering of RF energy.

Figure 19G:
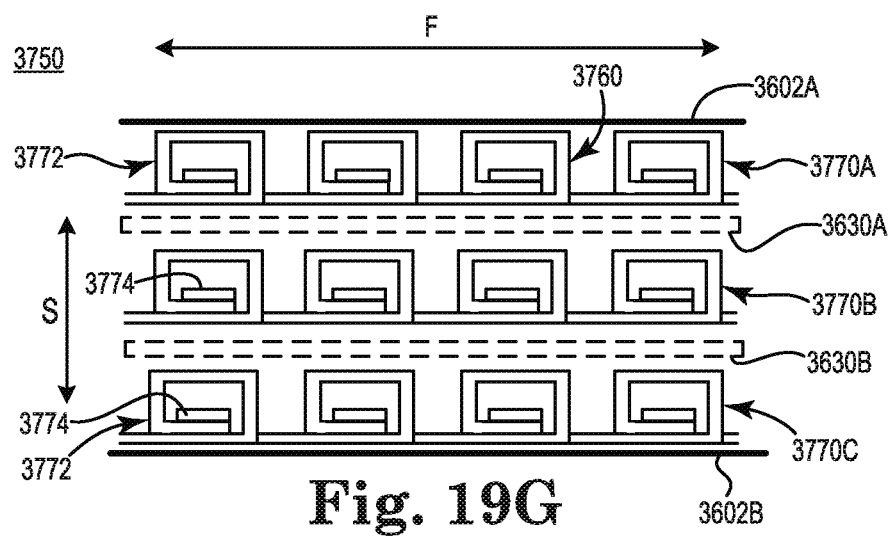
FIG. 19G is a view schematically representing an array of integrated passive devices in a portion of a lead, according to one example of the present disclosure.

FIG. 19G schematically represents a lead 3750 comprising an attenuation arrangement 3760 and signal conductors 3630A, 3630B, according to one example of the present disclosure. In some examples, the attenuation arrangement 3760 comprises rows 3770A-3770C of conductive partial loops 3772. In some examples, the attenuation arrangement 3760 comprises at least some of substantially the same features and attributes as the attenuation arrangements 3610 (FIG. 19A), except with each conductive partial loop 3772 comprising at least one integrated passive device 3774. In some examples, the integrated passive device 3774 comprises an inductive element (e.g. 250 in FIGS. 5A-5C). In some examples, the integrated passive device 3774 comprises elements other than an inductive element which may contribute to at least the anti-phase modality 217 (FIGS. 5A-5D), among other attenuation modalities 212, 214, 216 (FIGS. 5A-5D).

Figure 19H:
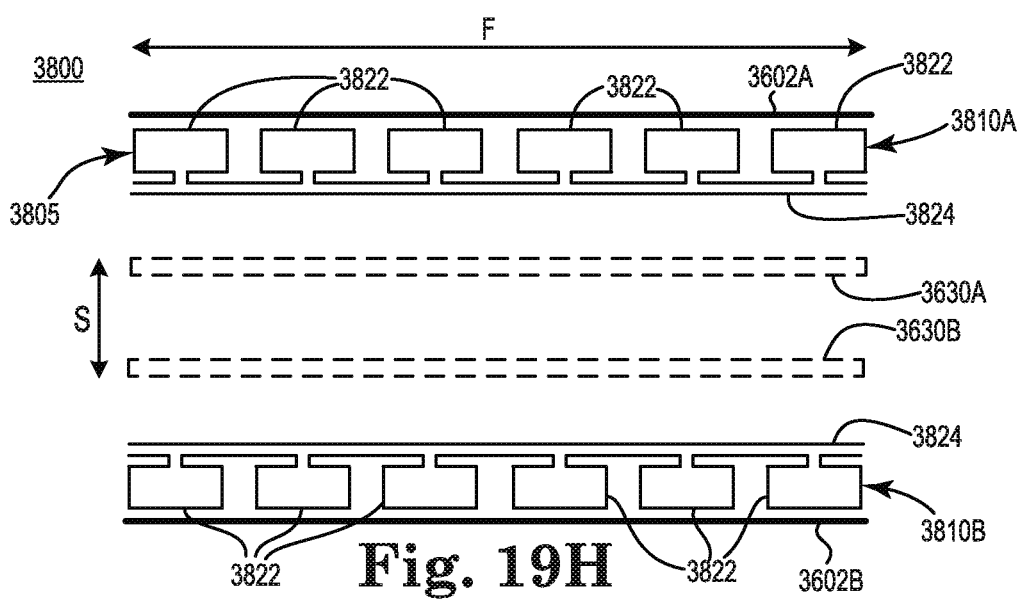
FIG. 19H is a view schematically representing arrays of capacitive structures in a portion of a lead, according to one example of the present disclosure.

FIG. 19H schematically represents a lead 3800 comprising an attenuation arrangement 3805, according to one example of the present disclosure. As previously noted in association with FIG. 19A, the view in FIG. 19H may represent a top view, side view, or bottom view of the lead 3800. As shown in FIG. 19H, lead 3800 comprises at least one signal conductor 3630A, 3630B extending along a length of lead 3800 (extending in orientation F) and with the attenuation arrangement 3805 positioned to intercept RF energy and prevent or minimize its coupling onto the signal conductors 3630A, 3630B.

As shown in FIG. 19H, the attenuation arrangement 3810 comprises rows 3810A, 3810B of capacitive conductive structures 3822 (relative to a continuous straight segment 3824) positioned near an exterior surface (e.g. a side, top, etc.) 3602A, 3602B of the lead 3800. In one aspect, the conductive structures 3822 may implement at least a shield modality (212 in FIGS. 5A-5D) while capacitively coupling the shield (structures 3822) relative to surrounding tissue to facilitate dissipation of the unwanted RF energy into the tissue and away from signal conductors 3630A, 3630B (and/or electrodes) in lead 3800.

Figure 19I:
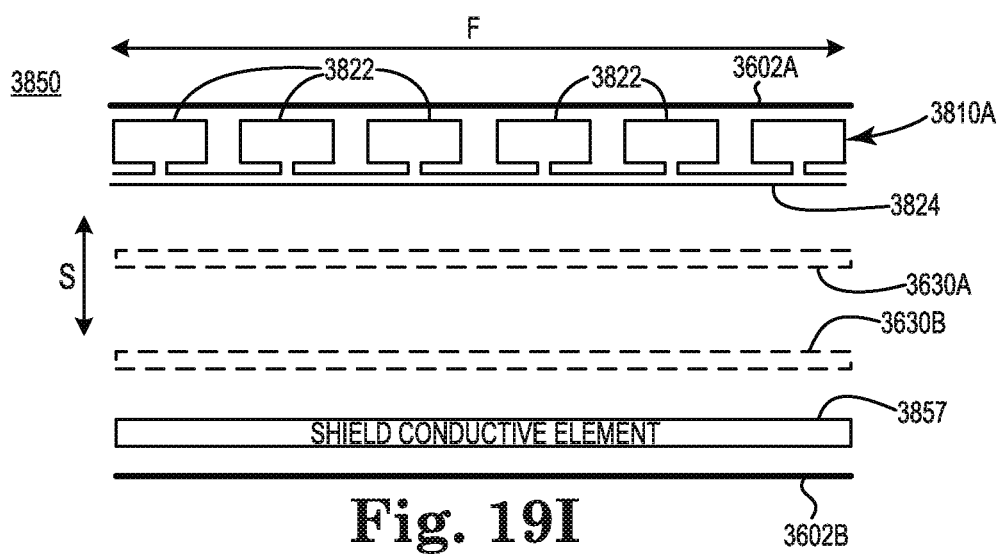
FIG. 19I is a view schematically representing at least one array of capacitive structures in a portion of a lead, according to one example of the present disclosure.

FIG. 19I schematically represents a lead 3850 comprising an attenuation arrangement 3855, according to one example of the present disclosure. In some examples, lead 3850 comprises at least some of substantially the same features and attributes as lead 3800 (FIG. 19H), except for omitting the capacitive structures 3822 near at least one outer wall (e.g. 3602B) of the lead 3850. Instead, a shield conductive element 3857 having a structure other than capacitive structures 3822 is positioned near one outer wall (e.g. opposite side or bottom 3602B). In this arrangement, the shield conductive element 3857 may be capacitively coupled to interstitial fluid, while the row of conductive structures 3822 facilitate capacitive coupling relative to surrounding tissues adjacent surface 3620A of lead 3850 such that row 3810A may act as a shield while directing energy for dissipation in the surrounding tissue.

Figure 20A:
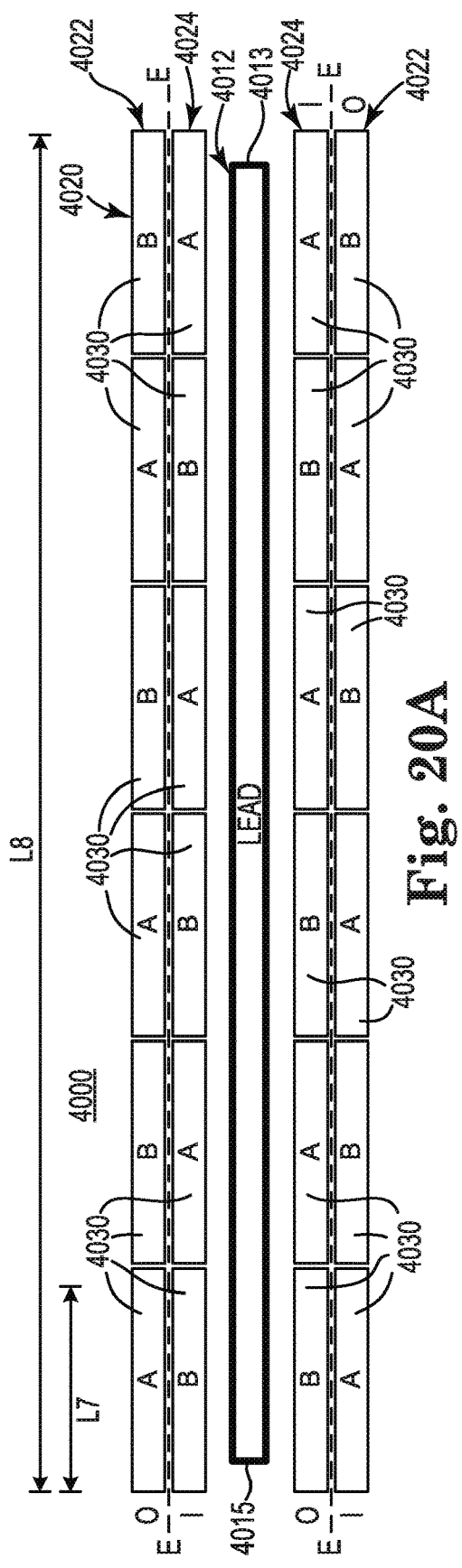
FIG. 20A is a side sectional view schematically representing an attenuation arrangement external to a lead, according to one example of the present disclosure.

FIG. 20A is side view schematically representing a lead assembly 4000, according to one example of the present disclosure. In some examples, lead assembly 4000 comprises a lead 4012 and a conductive arrangement 4020 circumferentially surrounding the lead 4012. In some examples, at least some aspects of the lead assembly 4000 comprises at least some of substantially the same features and attributes as the various leads and lead assemblies, including an attenuation arrangement, as described in association with at least FIGS. 1-19O. In some examples, lead 4012 may incorporate at least some aspects of an attenuation arrangement and in some examples, lead 4012 may omit aspects of an attenuation arrangement.

As shown in FIG. 20A, in some examples the conductive arrangement 4020 may be located external to lead 4012 and extend generally parallel to lead 4012 and at least between opposite ends 4013, 4015 of lead 4012. In some examples, conductive arrangement 4020 comprises an array 4022 of outer (O) conductive structures 4030 and an array 4024 of inner (I) conductive structures 4030 with dashed line E providing a reference point relative to which the respective inner positions and outer positions are identified. In some examples, a first plurality of substantially identical conductive structures 4030 at least partially defines array 4022 and a second plurality of substantially identical conductive structures 4030 at least partially defines array 4024. In some examples, some conductive structures 4030 identified via reference A may define conductive structures which have electrical continuity with each other along a length (L8) of the lead assembly 4000, with these conductive structures (A) alternating between having an inside (I) and an outside (O) position relative to reference line E. Similarly, in some examples, some conductive structures 4030 identified via reference B may define conductive structures which have electrical continuity with each other along a length (L8) of the lead assembly 4000, with these conductive structures (B) alternating between having an inside and an outside position relative to reference line E. Via this arrangement, in some examples the "A" conductive structures 4030 form a repeating pattern of alternating inside and outside position. In some instances, the inside position (I) of the "A" conductive structures 4030 may be sometimes be referred to being inverted relative to the outside position (O), or vice versa. Similarly, in some instances, the inside position (I) of the "B" conductive structures 4030 may be sometimes be referred to being inverted relative to the outside position (O), or vice versa. Moreover, in some instances, each switch or inversion of the "A" structures and "B" structures may sometimes be referred to as a transition.

In some examples, each conductive structure 4030 (A and/or B) comprises some conductive elements (e.g. wire, conductive trace, etc.) arranged in a pattern adapted to attenuate RF energy in some manner.

In some examples, at least the "A" conductive structures 4030 together form a single conductive structure extending the length of the lead 4012. In some examples, at least the "B" conductive structures 4030 together form a single conductive structure extending along the length of the lead 4102. In some such examples, the "A" conductive structures 4030 and the "B" conductive structures 4030 together form a single conductive structure, such as a coil. As described in further detail later in association with at least FIG. 20E, in some examples the "A" conductive structures 4030 and "B" conductive structures 4030 may be implemented via a single coil or multiple coils which are formed to alternate between an inside and an outside position.

In some examples, as later shown in the diagram FIG. 20G, the entire attenuation arrangement 4020 may be understood as being formed from or as a single continuous conductive element 4830 which travels a full length (L20) of the attenuation arrangement 4020A (and therefore a full length of at least the protected portion of the lead) twice, with the single continuous conductive element extending from an initial end 4810 in a first (e.g. forward FWD) direction before making a single reversal of direction 4802 one time at one end 4805 of the attenuation arrangement (and therefore one end of at least the protected portion of the lead) before extending in an opposite, second (e.g. reverse) direction (R) to the initial end 4810 of the attenuation arrangement. In doing so, in at least some such examples, the single conductive element forming attenuation arrangement does not change direction again to resume travel in the first/forward direction after the attenuation arrangement completes the initial reversal in direction. Stated differently, the opposite terminal ends 4812A, 4812B of the conductor forming the attenuation arrangement are located at the same end 4810 of the lead. It will be understood that FIG. 20G omits features such as coils and/or position inversions for illustrative simplicity and/or clarity in order to demonstrate the above-described general relationships exhibited in an attenuation arrangement (e.g. 4020 in FIG. 20A) in at least some examples of the present disclosure.

In some instances, at least some of the example arrangements described in association with FIG. 20A may comprise one implementation of at least shield modality 210 and/or an anti-phase modality 217 (e.g. also element 253), as described in association with at least FIGS. 5A-5D. In particular, the repeating pattern of alternating inside/outside positions of the "A" and "B" conductive structures 4030 may cause phases of RF e-fields to be in opposition such that phases on inside and outside (relative to reference line E) cancel each other. As such, the alternating patterns of "A" conductive structures 4030 and "B" conductive structures 4030 of conductive arrangement 4020 may sometimes be referred to as an anti-phase arrangement or as a phase-cancellation arrangement.

As shown in FIG. 20A, each "A" or "B" conductive structure 4030 has a length L7 which forms a portion of a total length L8 of the entire conductive arrangement 4120. In some examples, the length L7 may comprise about 5 percent to about 20 percent of the total length L8 of conductive arrangement 4120, such that inversions (of the "A" or "B" conductive structures 4030) between the respective inside (I) and outside (O) positions occur with a frequency based on the length L7. For instance, if length L7 is about 5 percent of the total length L8, then about 20 inversions (e.g. switches between the inside and outside position) would occur for "A" conductive structures 4030 (or for "B" conductive structures 4030) over the entire length of the conductive arrangement 4020. In some examples, the length L7 is the same for each conductive structure 4030. However, in some examples, some conductive structures 4030 may have lengths other than a length L7.

In some examples, the length L7 of the "A" or "B" conductive structures 4030 may comprise about two to three percent of the total length L8 such that much higher frequency of inversions take place for the "A" and "B" conductive structures 4030. For instance, if length L7 is about 2 percent of the total length L8, then about 50 inversions (e.g. switches between the inside and outside position) would occur for the "A" and "B" conductive structures 4030 over the entire length of the conductive arrangement 4020. Because of the high frequency of position inversions, such example arrangements may be more readily implemented via one of the example flexible printed electronic (FPE) assemblies, whether the FPE assembly is separate from the lead 4012 (e.g. FIG. 20A) or the FPE assembly is at least partially incorporated into the lead (e.g. FIG. 20B, 20C), such as when the lead is formed as a FPE assembly.

However, it will be understood that the attenuation arrangement 4020 may be implemented in non-FPE arrangements, i.e. structures which do not employ an FPE assembly to form the conductive arrangement 4020 and/or for the lead 4012. For instance, at least some of the examples described in association with at least FIGS. 21A-33, which may comprise a coil structure, may be implemented in an attenuation arrangement such as in FIG. 20A to implement an anti-phase modality 217 (FIG. 5A-5D).

Figure 20B:
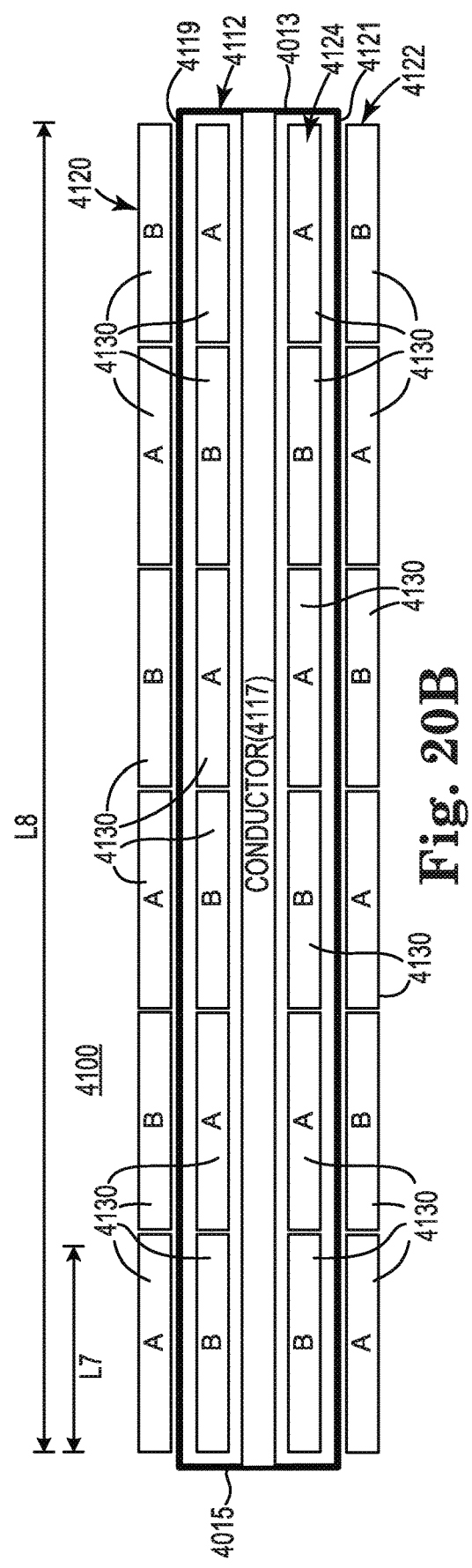
FIG. 20B is a side sectional view schematically representing an attenuation arrangement at least partially external to a lead, according to one example of the present disclosure.

FIG. 20B is a side view schematically representing a lead assembly 4100, according to one example of the present disclosure. In some examples, lead assembly 4100 comprises a lead 4112 and a conductive arrangement 4120 circumferentially surrounding the lead 4012 with at least a portion of conductive arrangement 4120 incorporated within a portion of lead 4112. Accordingly, in some examples lead assembly 4100 comprises at least some of substantially the same features and attributes as lead assembly 4000 (FIG. 20A), except with a portion (e.g. array 4122 of alternating "A", "B" conductive structures 4130) of arrangement 4120 external to lead 4112 while another portion (e.g. array 4124 of alternating "A", "B" conductive structures 4130) of conductive arrangement 4120 is internal to or incorporated within lead 4112.

In some examples, the conductive arrangement 4120 provides one example implementation of at least shield modality 210 and/or an anti-phase modality 217 (or element 253), as described in association with at least FIGS. 5A-5D, which may be employed to minimize the impact of external RF energy on conductors 4117 within lead 4112.

Figure 20C:
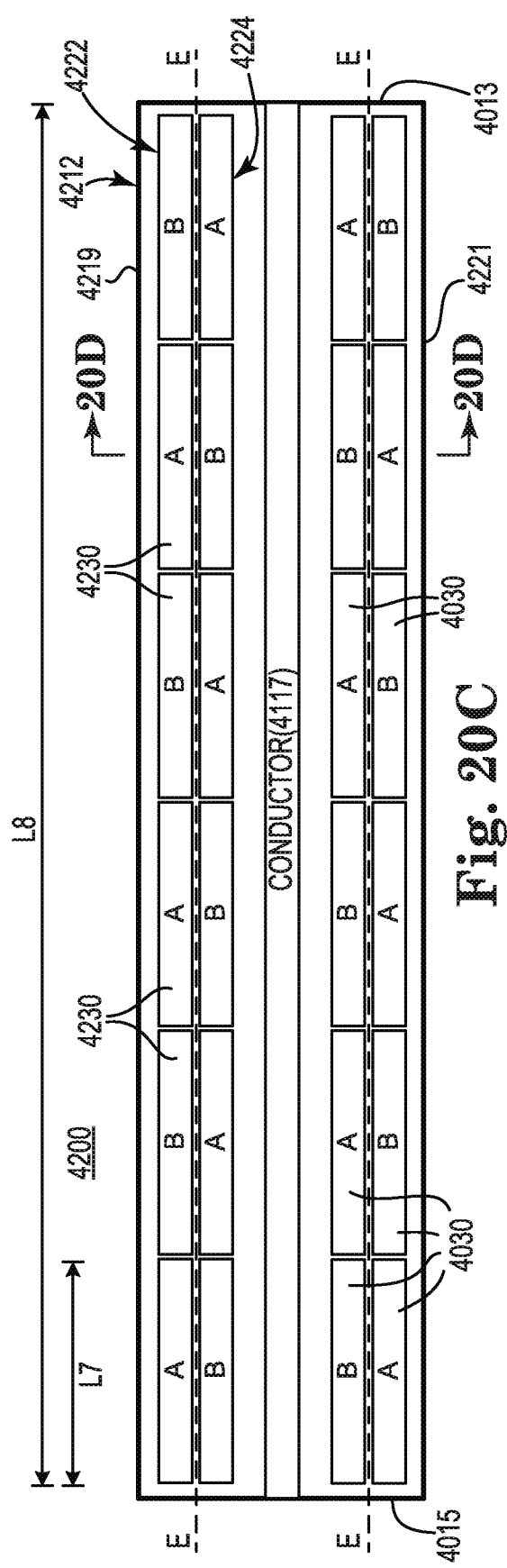
FIG. 20C is a side sectional view schematically representing an attenuation arrangement within a lead, according to one example of the present disclosure.

FIG. 20C is side view schematically representing a lead assembly 4200, according to one example of the present disclosure. In some examples, lead assembly 4200 comprises at least some of substantially the same features and attributes as lead assembly 4000, 4100 as described in association with at least FIGS. 20A-20B, except with the entire conductive arrangement 4220 being incorporated within or as part of lead 4112. In other words, the entire conductive arrangement 4220 is located within outer wall(s) 4219, 4221 of lead 4112 and is within the opposite ends 4013, 4015 of lead 4212.

In some examples, conductive arrangement 4220 circumferentially surrounds signal conductors (and/or other conductors) 4117, which may be located at an interior of lead 4212. However, in some examples, the conductive elements of conductive arrangement 4220 also may act as signal conductor(s) along a length of the lead, with the alternating inside/outside pattern of "A", "B" conductive structures 4230 providing a shield modality 210/212 and/or anti-phase modality 217 (also 253) as in FIGS. 5A-5D.

It will be understood that the various lead assemblies 4000, 4100, 4200 (FIGS. 20A-200) may be implemented according to leads having a wide variety of different cross-sectional shapes, such as circular, elliptical, rectangular, etc.

Figure 20D:
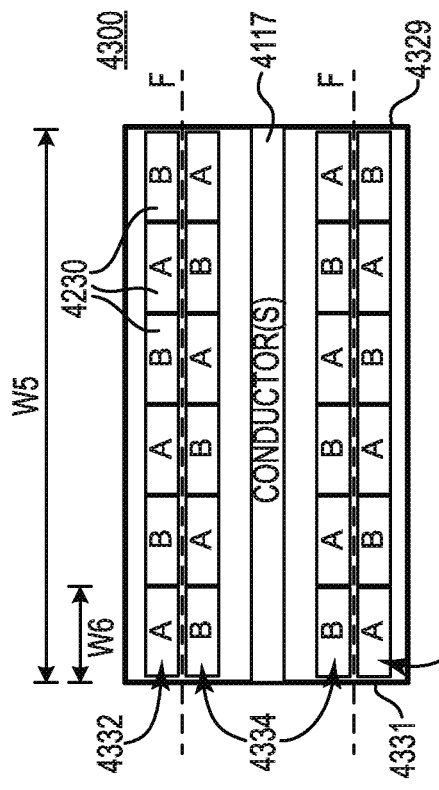
FIG. 20D an end sectional view schematically representing an attenuation arrangement within a lead, according to one example of the present disclosure.

In some examples, an arrangement of alternating pattern of conductive structures 4230 may be implemented across a width (e.g. laterally) of a lead, as shown in the sectional view of FIG. 20D. In particular, as shown in FIG. 20D, groups 4332, 4334 of conductive structures 4230 are arranged in an alternating pattern (represented via A, B) analogous to that shown in FIG. 20C, except for extending laterally instead of longitudinally (along the length of the lead). A width (W6) of the conductive structures 4230 forms a portion of the total width (W5) between opposite sides 4329, 4331 with width (W6) selectable to achieve a desired number of inversions laterally, in a manner similar to described above for FIGS. 20A, 20B, in order to achieve a desired degree of implementation of the shield and/or anti-phase modalities 212, 217 (FIGS. 5A-5D).

Figure 20E:
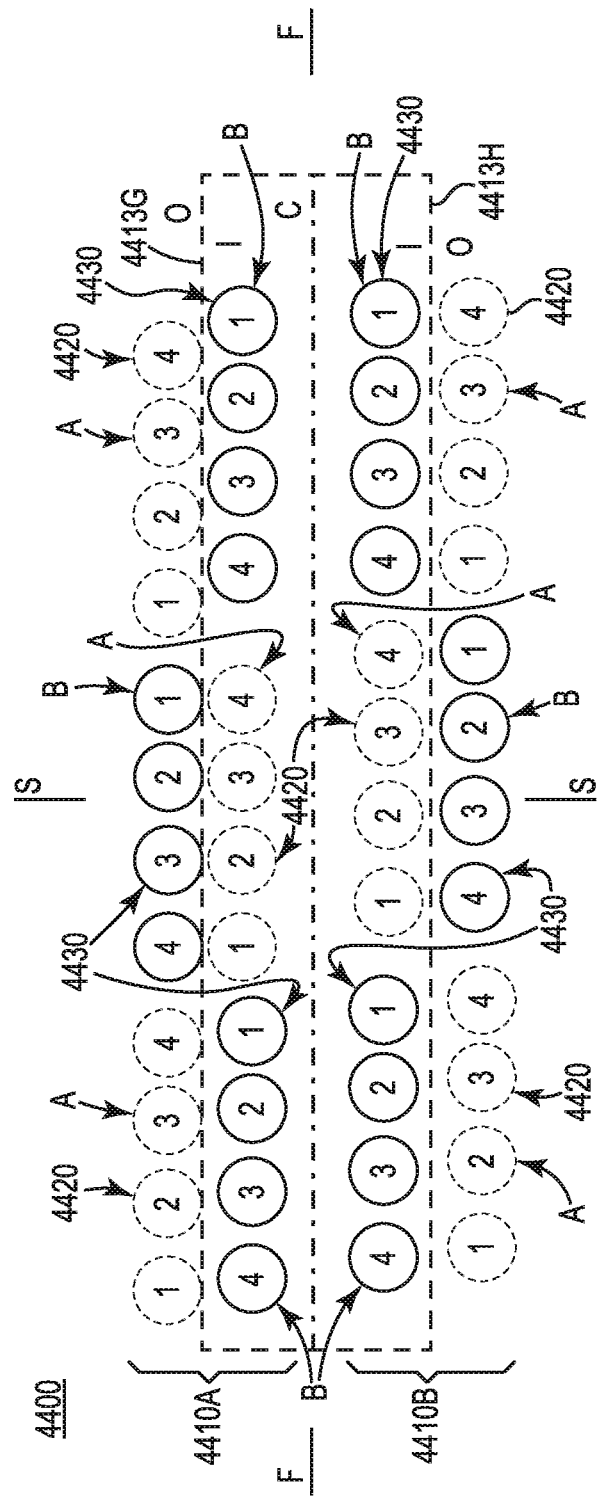
FIG. 20E is side sectional view schematically representing a coil structure, according to one example of the present disclosure.

FIG. 20E is a side sectional view schematically representing a coil structure 4400, according to one example of the present disclosure. In particular, coil structure 4400 may comprise one example implementation of an anti-phase modality (e.g. 217, 253 in FIGS. 5A-5D) and/or shield modality (e.g. 210, 212 in FIG. 5A-5D) of an attenuation arrangement in the manner described in association with at least FIG. 20A. Accordingly, in some examples, coil structure 4400 may comprise at least some of substantially the same features and attributes as the attenuation arrangements described in association with at least FIGS. 20A-20D.

As shown in FIG. 20E, in some examples the coil structure 4400 may be understood as having two halves 4410A, 4410B on opposite sides of a centerline C aligned in a first orientation (F).

For instance, as shown in FIG. 20E, upon considering one half 4410A of coil structure 4400, it may be seen that a group 4420 of coils (e.g. 1, 2, 3, 4 in dashed circles) may correspond to one of the "A" conductive structures 4030 in lead 4000 of FIG. 20A and a group 4422 of coils (e.g. 4, 3, 2, 1 in solid circles) may correspond to one of "B" conductive structures 4030 in lead 4000 in FIG. 20A. Moreover, dashed lines 4413G and 4413H in FIG. 20E represent a reference by which particular portions of each half 4410A, 4410B of the coil structure 4400 may be considered to exhibit an inside position (I) or an outside position (O). However, the reference defined by dashed lines 4413G, 4413H does not generally correspond to a physical barrier between the "A" coils of groups 4420 and "B" coils of groups 4422, except when the coil structure 4400 may be an example implementation of the example of FIG. 20B.

In a manner similar to FIG. 20A, at regular intervals (e.g. L7 in FIG. 20A) the "A" conductive structures (e.g. 1, 2, 3, 4 in dashed circles) of coil structure 4400 in FIG. 20E experience a transition between an inside position (I) and an outside position (O) and the "B" conductive structures (e.g. 4, 3, 2, 1 in solid circles) experience a transition between an inside position (I) and an outside position (O). Stated differently, in some instances such transitions may sometimes be referred to as regularly occurring inversions of the respective "A" and "B" conductive structures.

With this arrangement in mind, it may be understood that the regularly occurring transitions (e.g. inversions) between the inside (I) and outside (O) positions of the respective "A" groups 4420 of coil portions and "B" groups 4422 of coil portions may achieve an anti-phase cancellation in external RF energy, such as from an MRI field. In particular, this alternating pattern in coil structure 4400 may produce opposing phases of the e-fields of the MRI field, which cancel each other out, which in turn may minimize the effect of these e-fields on the signal conductors carried by a lead (having this coil structure 4400 deployed in one of the configurations shown in at least FIGS. 20A-20D).

In some examples, coil structure 4400 in FIG. 20E may be implemented as one of the non-FPE coiled arrangements and/or FPE coiled arrangements as described in association with at least FIGS. 21A-33.

Figure 20F:
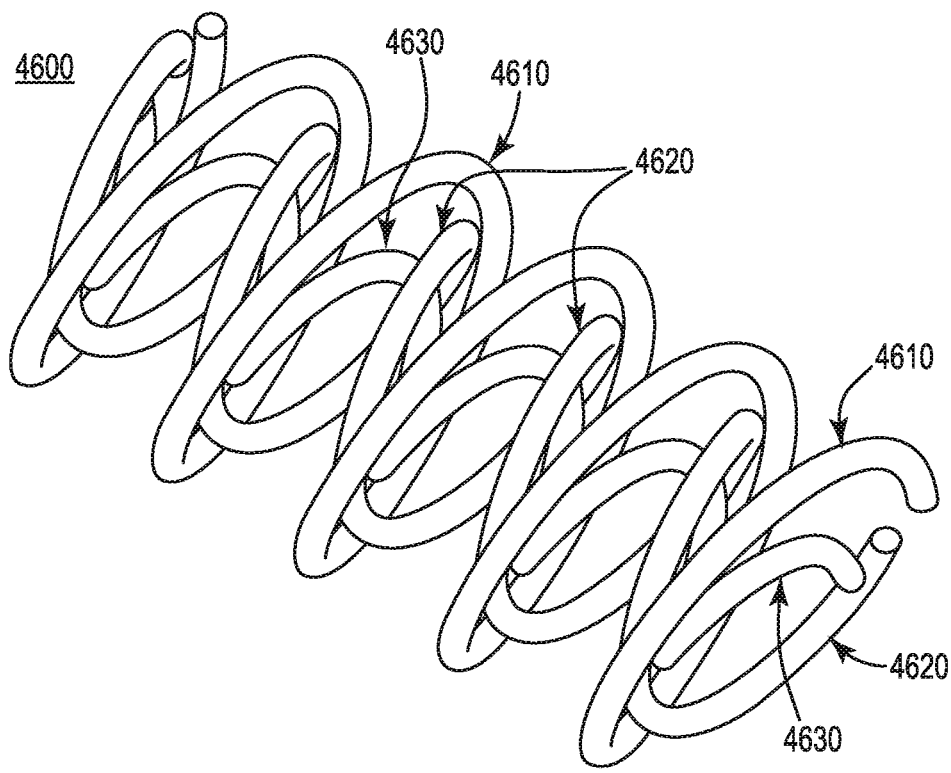
FIG. 20F is an isometric view schematically representing a coil structure, according to one example of the present disclosure.
Figure 20G:
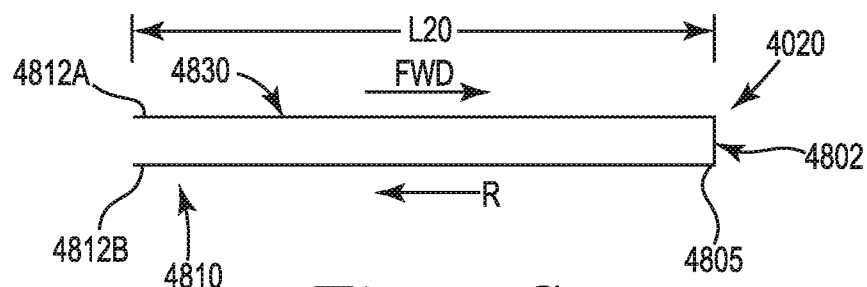
FIG. 20G is a diagram schematically representing an attenuation arrangement, according to one example of the present disclosure.

FIG. 20F is an isometric view schematically representing a coil structure 4600, according to one example of the present disclosure.

As shown in FIG. 20F, in some examples the coil structure 4600 comprises a plurality of co-axial coils. In some examples, coil structure 4600 comprises an outer coil 4610 and inner coil 4630, and an intermediate coil 4620 interposed (circumferentially) between the outer coil 4610 and the inner coil 4630. In one aspect, the outer coil 4610 and the intermediate coil 4620 are wound in opposite orientations, and with the inner coil 4630 being wound in the same orientation as the outer coil 4610, and therefore an opposite winding orientation than the intermediate coil 4620.

In some examples, an outer coil 4610 and an intermediate coil 4620 together provide a shield arrangement while an inner coil 4630 provides a signal conductor. In this way, the gaps between coil 4610 and 4620 are minimized while still providing the ability for the coils to flex along the length of the lead, in contrast with a contiguous shield that does not incorporate opposing coiled structures. In some examples, outer coil 4610 and/or intermediate coil 4620 are arranged adjacent to tissue to provide direct dissipation of RF energy. In some examples, outer coil 4610 and/or intermediate coil 4620 are coated in an insulative material prior to winding to provide capacitive dissipation of RF energy.

In some examples, outer coil 4610 and/or intermediate coil 4620 are coated in an insulative material after winding to provide capacitive dissipation of RF energy. In some such arrangements, at least some portions of the respective outer and intermediate coils 4610, 4620 are in electrical contact, thereby forming a low impedance shield structure by virtue of electrical connection between opposing coils, while maximizing capacitive coupling to tissue.

In some examples, the size and/or shape of the respective outer and intermediate coils 4610, 4620 are formed and/or patterned in an arrangement which does not extend 360 degrees about the periphery of the inner coil 4630.

In some examples, coil structures 4500 or 4600 may be implemented as one of the non-FPE coiled arrangements and/or FPE coiled arrangements as described in association with at least FIGS. 21A-33.

In some of the previously described examples associated with at least FIGS. 20A-20F, when such conductive arrangements are implemented via a coil structure formed as part of a FPE assembly, a substantially greater number of radial coils (e.g. 20) may be employed than in a non-FPE assembly (e.g. 3) because forming an FPE assembly can be performed in a manner permitting placing a much higher density of distinct radial coils within a given volume. In addition, in some examples in which the conductive arrangements of at least FIGS. 20A-20E are implemented via a FPE assembly, and to the extent that the conductive arrangements may serve as a shield and/or anti-phase structure which are separate from signal conductors of a lead, then the signal conductors may take any desired shape or form, and need not embody a coil shape.

In some examples, in which the example conductive arrangements of FIGS. 20A-20E are implemented via a FPE assembly and such arrangements may act as a shield, at least some of the conductive structures extending along the length of the lead may be shorted at some locations.

In some examples in which the example conductive arrangements of FIGS. 20A-20E may be implemented via a non-FPE assembly, each conductor may extend twice the length (L8) of the lead body. In some such examples, a first pass of the single conductor may comprise "A" conductive structures 4030 and an opposite second pass of the single conductor may comprise "B" conductive structures 4030. Accordingly, each conductor passes through the MRI field (adjacent the lead) twice such that at each point along the MRI field, the conductor is simultaneously exposed to the MRI field and exposed to an inversion of the MRI field. This arrangement results in an effective cancellation of the phase(s) of the MRI field, thereby substantially absorbing a significant amount of RF energy. In some examples, this arrangement may reduce the total energy absorbed along the conductor and/or may reduce the amount of temperature increase occurring during exposure to a MRI field.

Figure 21A:
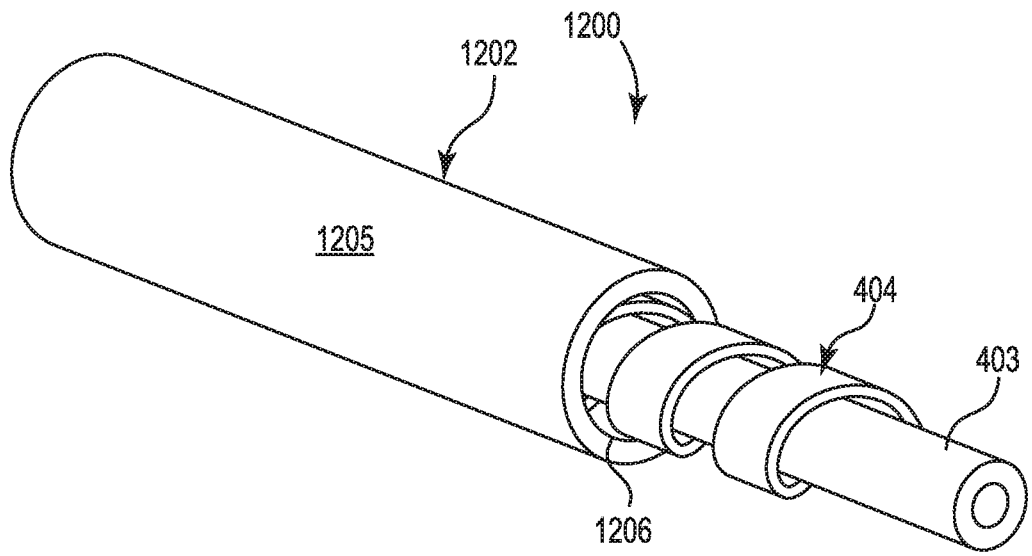
FIG. 21A is a perspective view schematically representing an implantable lead assembly including a FPE assembly in a helically wound configuration about an elongate support member and extending within an outer flexible tubular insulator, according to one example of the present disclosure.

FIG. 21A is a perspective view schematically representing an implantable lead assembly 1200 including a FPE assembly 404 in a helically wound configuration and an outer tubular insulator 1202, according to one example of the present disclosure. In some examples, lead assembly 1200 comprises at least substantially the same features and attributes as lead assembly 400 in FIG. 6A, except for further comprising an outer tubular insulator 1202 through which the helically wound FPE assembly 404 (and elongate support member 403) extends. As shown in FIG. 21A, the outer tubular insulator 1202 acts as a cover to protect the FPE assembly 404 (and elongate support member 403) from body fluids, unwanted fibrotic growth, etc. In addition, the generally smooth outer surface 1205 of the insulator 1202 may ease insertion and advancement of the lead assembly 1200.

In some examples, the outer tubular insulator 1202 may help to prevent kinking of the lead assembly 1200, provide increased flex resistance, and/or provides a feel to the operator that more closely resembles a traditional lead structure. As previously described in association with at least FIG. 6A, the support member 403 also may help to prevent kinking of the lead assembly 1200, provide increased flex resistance, and/or provides a feel to the operator that more closely resembles a traditional lead structure.

In some examples, the FPE assembly 404 omits an interior shield element, such as second shield conductive element 517B (and outer insulator 520B in FIG. 16), such that shielding functionality is provided on just one side (e.g. the exterior portion) of the FPE assembly 404 such as via first shield conductive element 517A, such as shown in FIG. 7D.

In some examples, elongate support member 403 is omitted from lead assembly 1200.

Figure 21B:
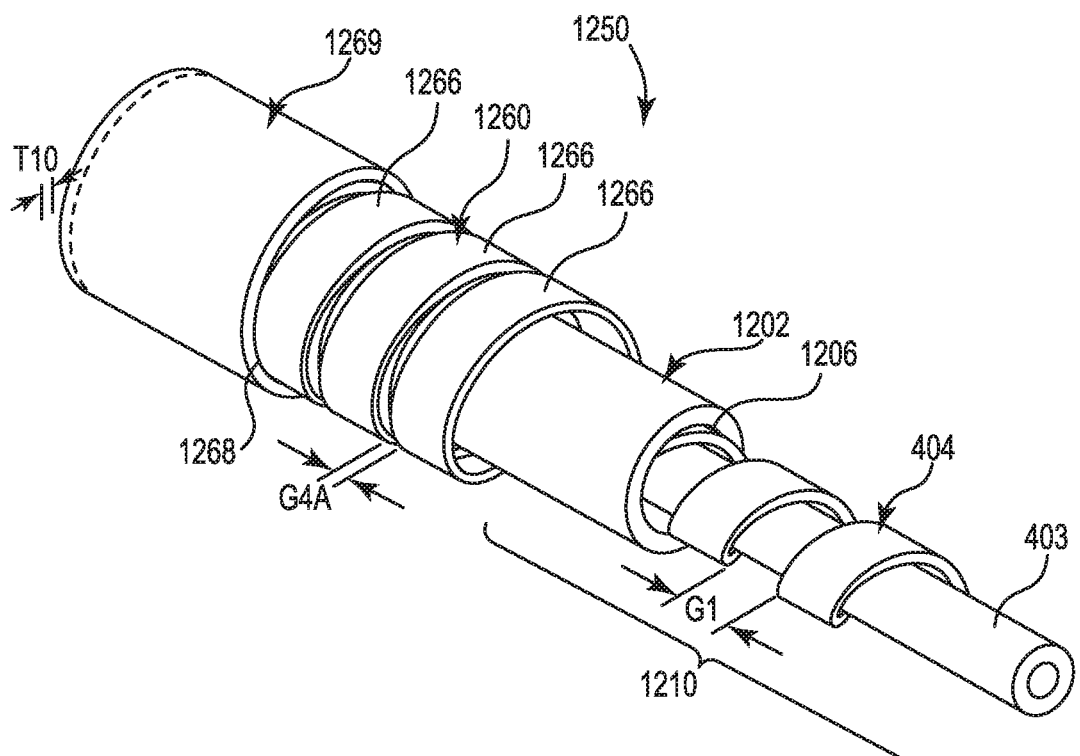
FIG. 21B is a perspective view schematically representing an implantable lead assembly including the FPE assembly of FIG. 21A and including a second FPE assembly in a helically wound configuration as an external shield, according to one example of the present disclosure.
Figure 21G:
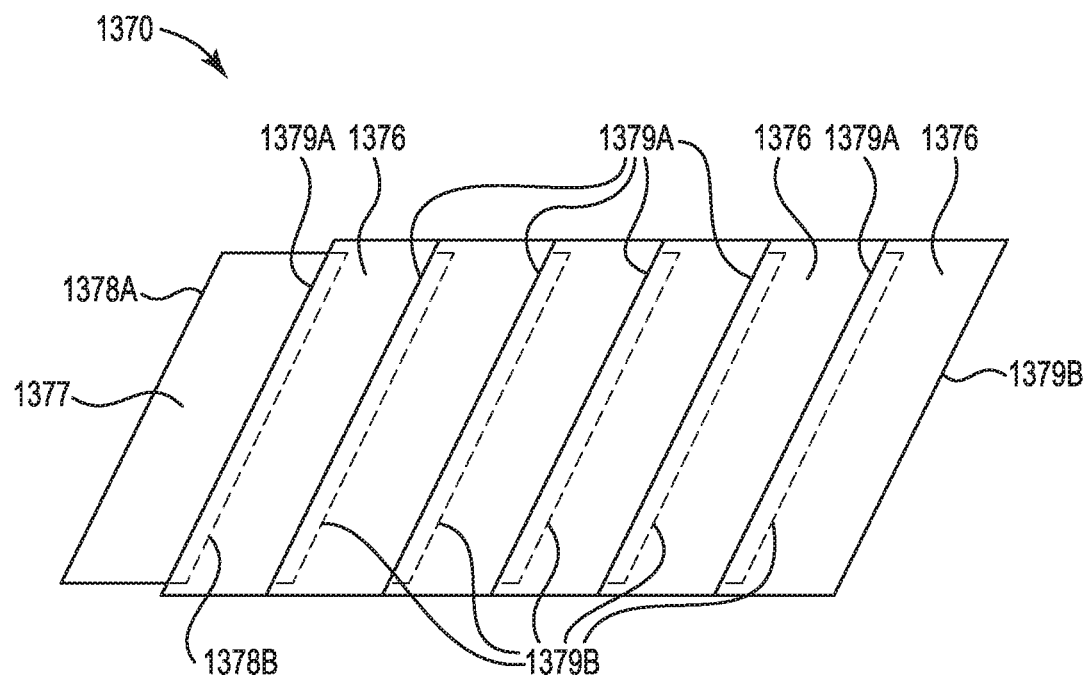
FIG. 21G is partial top plan view schematically representing a FPE assembly including overlapping windings, according to one example of the present disclosure.

FIG. 21B is a perspective view schematically representing an implantable lead assembly 1250 including a lead subassembly 1210 and FPE assembly 1260 as an external shield, according to one example of the present disclosure. In some examples, the subassembly 1210 comprises at least substantially the same features and attributes as the lead assembly 1200 in FIG. 21A, and therefore includes a first FPE assembly 404 (and elongate support member 403 therein) extending through a lumen 1206 defined by outer insulator 1202. Via this arrangement, the first FPE assembly 404 may convey signals (e.g. sensing and/or stimulation) along a length of lead assembly 1250. Accordingly, the first FPE assembly 404 of the subassembly 1210 includes any one or several the attenuation modalities 212, 214, 216, 217 in FIG. 5A, and in addition, exhibits the helically wound configuration which provides additional shielding and/or filtering functionality, as well as enhancing pushability, steerability, etc. of the lead assembly 1210.

As shown in FIG. 21B, the lead assembly 1250 includes a second FPE assembly 1260 helically wound about the outer insulator 1202 of the lead subassembly 1210. An outer tubular insulator 1269 defines a lumen 1268 through which the elements (1210, 1260) extend longitudinally, with the insulator 1269 protecting FPE assembly 1260 from unwanted fibrotic growth, body fluids, etc.

In one aspect, the second FPE assembly 1260 acts as an external shield, corresponding to at least the shield modality 210 in the attenuation arrangement 204 in FIG. 5A. Accordingly, in some examples the second FPE assembly 1260 embodies one or several of the attenuation elements of array 241 (FIG. 5A) such as a coil element 240 FIG. 5A (e.g. the 3D coil structure of FIG. 9), a mesh structure 242 in FIG. 5A, FPE assembly 245, inductive element 250, and/or capacitive element 252.

As noted above, in some examples, the first FPE assembly 404 may comprise one or several attenuation modalities (e.g. 212, 214, 216, 217). Accordingly, in some examples, the lead assembly 1250 includes both an external shield modality (e.g. 210 in FIG. 5A) and an internal shield modality (e.g. 212, 214, 216 in FIG. 5A). In such examples in which both the FPE assemblies 404, 1160 including shielding functionality, the lead assembly 1250 comprises a double layer of shielding for signal conductive elements 514A, 514B.

However, in some examples, the first FPE assembly 404 comprises no attenuation modalities and relies solely on the external shield provided via the second FPE assembly 1260.

In some examples, the second FPE assembly 1260 omits signal conductive elements (e.g. 514A, 514B) such that second FPE assembly 1260 does not convey sensing signals and/or stimulation signals along the lead assembly 1250. In such examples, the second FPE assembly 1260 acts solely as an external shield, i.e. does not act to convey signals.

However, in some examples, the second FPE assembly 1260 includes signal conductive elements (e.g. 514A, 514B) to convey signals, such the first and second FPE assemblies 1210, 1260 form a coaxial arrangement in which the respective FPE assemblies 1210, 1260 carry signals independently from each other.

As shown in FIG. 21B, the second FPE assembly 1260 is in a helically wound configuration of windings 1166 having a gap G4A between adjacent windings. In some examples, the gap G1 between adjacent windings 406 of the first FPE assembly 404 is larger than the gap G4A between adjacent windings 1266 of second FPE assembly 1260, thereby providing more flexibility. In some examples, the smaller gap G4A between adjacent windings 1266 of the is selected to enhance shielding, such as when the gap G4A is at least one order of magnitude less than a wavelength of the MRI-energy field signals (within the body). In some examples, the gap G4A is at least two orders of magnitude less than a wavelength of the MRI-energy field signals (within the body). In some examples, the thickness (T10) of outer tubular insulator 1269 may be and/or the gap G4A may be minimized in order to increase capacitive coupling to body tissue, thereby enhancing shielding of RF energy.

In some examples, deploying the helically wound (e.g. coiled) configuration of the second FPE assembly 1260 about the lead subassembly 1210 may help to prevent kinking, may increase mechanical flex resistance, and/or may enhance a more traditional operational feel when handling the lead assembly 1250. In one aspect, enhancing the mechanical flex resistance may enhance overall reliability of the first FPE assembly 404 because the coil 1290 protects the conductive elements and substrate of the FPE assembly from the full impacts of external mechanical forces within the body on the FPE assembly which occur during normal patient behavior.

In some examples, the FPE assembly 404 omits an interior shield element, such as second shield conductive element 517B (and outer insulator 520B in FIG. 16), such that shielding functionality is provided on just one side (e.g. the exterior portion) of the FPE assembly 404 such as via first shield conductive element 517A, such as shown in FIG. 7D.

In some examples, elongate support member 403 is omitted from lead assembly 1250.

FIG. 21C is a perspective view schematically representing an implantable lead assembly 1272 including the FPE assembly of FIG. 21B and including an external shield in which a third FPE assembly 1270 has helical windings in an opposite orientation relative to the helical windings of the second FPE assembly 1260, according to one example of the present disclosure. In some examples, the lead assembly 1272 comprises at least substantially the same features and attributes as the lead assembly 1250 (FIG. 21B), except further comprising third FPE assembly 1270. Moreover, third FPE assembly 1270 comprises at least some of substantially the same features and attributes as second FPE assembly 1260. However, FPE assembly 1270 has a larger inner diameter (D3 in FIG. 21D) than the inner diameter (D4 in FIG. 21D) of FPE assembly 1260, and FPE assembly 1270 is oriented with its windings 1276 pointing in a non-parallel direction diverging from an orientation of the windings 1266 of FPE assembly 1260. In some instances, this may be referred to oppositely oriented windings. Via this arrangement, the respective FPE assemblies 1260 and 1270 effectively form a mesh-like pattern, as further shown in FIG. 21D.

FIG. 21D is partial top plan view schematically representing the opposite orientation of the helical windings 1266, 1276 of the respective second and third FPE assemblies 1260, 1270, according to one example of the present disclosure. Via this arrangement, the inductance of the conductors may be increased, the capacitive coupling to body tissue may be increased, thereby increasing the impedance of the conductor at high frequencies, forming a filter for RF energy.

FIG. 21E is a perspective view schematically representing an implantable lead assembly 1282, according to one example of the present disclosure. Lead assembly 1282 includes the FPE assembly 1260 of FIG. 21B and an external shield in which a third FPE assembly 1280 has helical windings 1286 in generally the same orientation relative to the helical windings 1266 of the second FPE assembly 1260, according to one example of the present disclosure. FIG. 21F is partial top plan view schematically representing the generally same orientation of the helical windings 1266, 1286 of the respective second and third FPE assemblies 1260, 1280, according to one example of the present disclosure.

In some examples, the lead assembly 1282 comprises at least substantially the same features and attributes as the lead assembly 1250 (FIG. 21B), except further comprising third FPE assembly 1280. Moreover, third FPE assembly 1280 comprises at least some of substantially the same features and attributes as second FPE assembly 1260. However, FPE assembly 1280 has a larger inner diameter (D3 in FIG. 21F) than the inner diameter (D4 in FIG. 21F) of FPE assembly 1260. FPE assembly 1280 is oriented with its windings 1286 pointing in the same direction (e.g. general parallel) as the windings 1266 of FPE assembly 1260.

Via this arrangement, the respective FPE assemblies 1260 and 1280 effectively form an overlapping pattern, as further shown in FIG. 21F. In this pattern, the windings 1286 of one FPE assembly 1280 overlaps with the gaps between the windings 166 of the other FPE assembly 1260. In some examples, this arrangement of overlapping windings (having the same orientation) may serve to increase the capacitive coupling to body tissue, thereby increasing the impedance of the conductor at high frequencies, forming a filter for RF energy.

FIG. 21F is top plan view of a FPE assembly 1370, according to one example of the present disclosure. In some examples, the FPE assembly 1370 comprises an overlapping configuration like that of FPE assemblies 1260, 1280 in FIGS. 20D-20E, except for being implemented via a single helically wound FPE assembly 1370 in which each winding partially overlaps a preceding winding to eliminate gaps between the adjacent windings. As shown in FIG. 21F, a first winding 1377 includes a first edge 1378A and an opposite second edge 1378B, and each subsequent overlapping windings 1376 include a first edge 1379A and an opposite second edge 1379B. In some examples, this arrangement of overlapping windings (having the same orientation) may serve to increase the capacitive coupling to body tissue, thereby increasing the impedance of the conductor at high frequencies, forming a filter for RF energy. In one aspect, the overlapping windings 1376 effectively form a solid column or tube of conductive material to enhance shielding of conductive elements interior of the windings 1376.

Figure 21H:
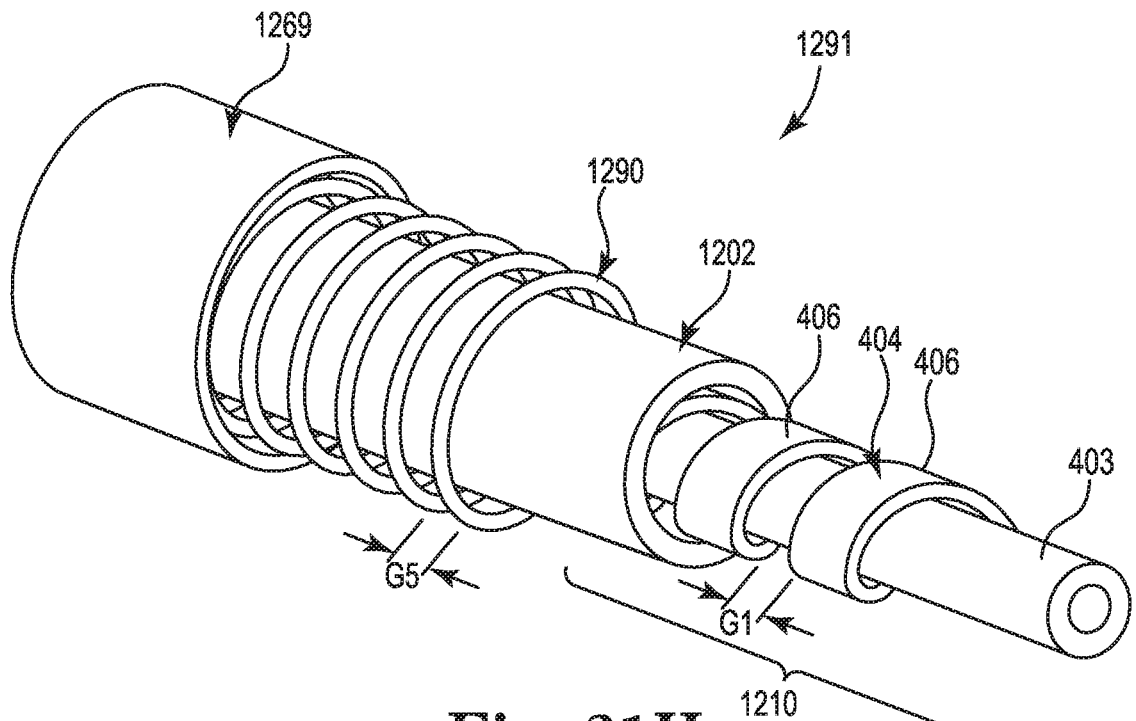
FIG. 21H is a perspective view schematically representing an implantable lead assembly including the FPE assembly of FIG. 21A and further including an external coil shield, according to one example of the present disclosure.

FIG. 21H is a perspective view schematically representing an implantable lead assembly 1291, according to one example of the present disclosure. In some examples, the lead assembly 1291 comprises at least substantially the same features and attributes as lead assembly 1250 in FIG. 21B, except for replacing the second FPE assembly 1260 with a coil 1290 of conductive material helically wound about the tubular insulator 1202. In some examples, coil 1290 comprises a wire or similar elongate, generally cylindrical structure having a relatively small diameter. However, in some examples instead of being a cylindrical structure, the adjacent conductive elements (e.g. windings) defining coil 1290 may be flat, mesh, etc.

In one aspect, the coil 1290 provides mechanical flex resistance to enhance overall reliability of the FPE assembly because the coil 1290 protects the conductive elements and substrate of the FPE assembly from the full impacts of external mechanical forces within the body on the FPE assembly 404 which occur during normal patient behavior. However, in some examples, coil 1290 may provide greater flexibility and/or simplicity than using a second FPE assembly 1260 as in the example of FIG. 20.

In some examples, lead assembly 1291 omits elongate support member 403.

In one aspect, coil 1290 includes windings 1292 which are spaced apart by a distance G5. In some examples, the spacing G5 is at least one order of magnitude less than a wavelength of the MRI-energy field signals (within the body). In some examples, the spacing G5 between adjacent windings of coil 1290 is substantially smaller than a spacing G1 between adjacent windings of the FPE assembly 404.

In one aspect, the combination of a FPE assembly 404 and external coil 1290 may provide numerous functions. For instance, as noted above, the FPE assembly 404 may enable more precise control over capacitive coupling of the shielding component relative to the surrounding tissue. Moreover, in one aspect, this arrangement provides two independent MRI shielding layers to be incorporated into a single lead assembly 1291 while minimizing a diameter of the lead assembly 1291. Accordingly, via the particular configuration of the lead assembly 1291, this arrangement could provide additional MR shielding to be incorporated into a lead assembly with many fewer components and with a much simpler lead design/manufacturing than prior commercial attempts at implementing MRI shielding into a lead assembly.

In some examples, the external coil 1290 is not physically coupled or electrically coupled to the lead subassembly 1210 and outer tubular insulator 1269 is omitted, such that the external coil 1290 may sometimes be referred to as a floating coil or a floating shield because it is separate from, and independent of, the lead subassembly 1210. This freestanding coil 1290 can receive the MRI energy and dissipate the energy over a large surface area via its direct contact with tissue. In this way, the coil 1290 acts as a shield or dissipating tool, which may reduce the amount of MRI energy received at the conductive elements, such as but not limited to the relative small surface area electrodes of the lead assembly.

In some examples, such a floating external coil 1290 may include a thin coating to inhibit fibrotic tissue growth on the coil 1290 with the materials selected so as to not significantly reduce the conductivity of the coil 1290 relative to the surrounding tissue to which the coil 1290 is intended to be coupled. In some examples, such coatings can be made from a polytetrafluoroethylene (PTFE) material (e.g. a GORE-TEX® material), a conductive polyurethane tubing, a conductive silicone tubing, parylene, etc. In some examples, the coating can be a very thin non-conductive tubing with some apertures to allow fluid ingress to establish conductivity to the surrounding tissue, yet otherwise still inhibit unwanted fibrotic tissue growth.

Via such coatings and/or tubing, the external coil 1290 may be explanted with less difficulty than in the absence of such coatings or tubings.

FIG. 22A is a perspective view schematically representing an implantable lead assembly 1295, according to one example of the present disclosure. In some examples, the lead assembly 1295 comprises at least some of substantially the same features and attributes as lead assembly 1291 in FIG. 21H, except for eliminating outermost tubular insulator 1269 and also replacing or modifying coil 1290 of conductive material with a coil 1293 (of windings 1294) which is wound about tubular insulator 1202. In some examples, in this arrangement the coil 1293 is bonded to, and/or arranged within, an outer surface 1203 of tubular insulator 1202. In some such examples, dip coating of the coil 1293 (such as via the dip coating described in association with at least FIG. 21H) may facilitate bonding the coil 1293 relative to the outer surface 1203.

FIG. 22B is a perspective view schematically representing an implantable lead assembly 1300 including a FPE assembly 1304 extending through an outer tubular insulator 1302, according to one example of the present disclosure. In some examples, the FPE assembly 1304 comprises at least some of substantially the same features and attributes of an FPE assembly and/or lead assembly, as previously described in association with at least FIGS. 1-22B. For instance, the FPE assembly 1304 may include signal conductive elements 514A, 514B (FIG. 7A-7E) such that lead assembly 1300 may convey along its length a sensing and/or stimulation signal.

As in the prior examples, the FPE assembly 1304 includes one of the modalities 212, 214, 216, 217 of an attenuation arrangement 204. In some examples, the FPE assembly 1304 may include shield conductive elements 517A, 517B (FIG. 7A-7E) and in some examples, additionally includes additional shielding components, as in at least some of the examples throughout FIGS. 10-33. Moreover, in some examples the FPE assembly 1304 comprises inductive and/or capacitive attenuation elements 250, 252 (FIG. 5A).

However, in the example of lead assembly 1300, the FPE assembly 1304 is not provided in a helically wound configuration about an elongate support member 403 as in FIG. 6A. Instead, as shown in FIG. 22B, the FPE assembly 1304 defines the most central or core element of the lead assembly 1300 and the FPE assembly 1304 extends in an unwound configuration as a straight elongate rectangular member. The outer tubular insulator 1302 helps to protect the FPE assembly 1304 from unwanted fibrotic growth, body fluids, etc. while also providing a smoother outer surface to facilitate insertion and advancement of lead assembly 1300 through body when implanting the lead assembly 1300. In some examples, the outer tubular insulator 1302 may be formed with a larger wall thickness and/or relatively firm material (e.g. material hardness) to provide at least some mechanical flex resistance to protect the FPE assembly 1304. In some examples, such as when the FPE assembly 1304 can include an outer surface having some exposed electrical conductive elements, such as in at least FIGS. 15-16, the outer tubular insulator prevents direct coupling of such conductive elements with the surrounding body tissue.

In one aspect, by providing the internal FPE assembly 1304 in an unwound (e.g. straight) configuration, manufacturing of the lead assembly 1300 is simplified and a much shorter length of the FPE assembly 1304 is used, than if it were helically wound. Accordingly, this arrangement decreases costs and use of material. In addition, providing the FPE assembly 1304 in a straight configuration provides a lower impedance path for the signal conductive elements (e.g. 514A, 514B) than the helically wound configuration.

In another aspect, via its straight configuration, the FPE assembly 1304 offers shielding functionality for its signal conductive elements 514A, 514B without adopting a coiled or helically wound configuration. Stated differently, overall formation of the lead assembly 1300 is greatly simplified, yet shielding functionality is still achieved via incorporating shielding and/or filtering functionality via printing the shielding components and relationships integrally within the FPE assembly 1304. As previously noted in connection with at least FIGS. 6A-6B, 7E, the FPE assembly 1304 forms a monolithic structure incorporating both signal functionality and shielding functionality into a single, unitary member.

In some examples, the FPE assembly 1304 may be longer than the outer tubular insulator 1302 to facilitate flexing of the FPE assembly 1304, such as when implanting and/or maneuvering the lead assembly 1300. In some such examples, this relationship may be achieved via the FPE assembly 1304 protruding from an end of the tubular insulator 1302 and/or forming a portion of the FPE assembly 1304 (that extends within/through insulator 1302) to include at least one fold, undulation, etc. to enhance extensibility and/or flexing functionality for the FPE assembly 1304.

Figure 23:
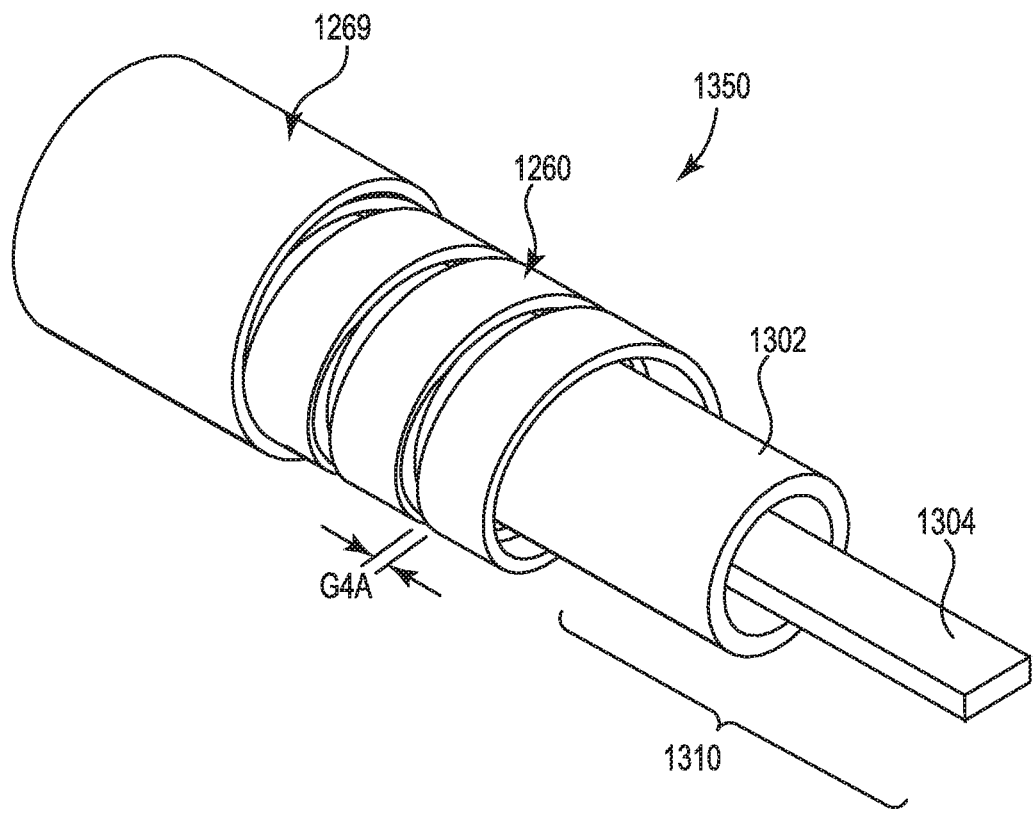
FIG. 23 is a perspective view schematically representing an implantable lead assembly including the lead assembly of FIG. 22B and further including a second FPE assembly in a helically wound configuration as an external shield, according to one example of the present disclosure.

FIG. 23 is a perspective view schematically representing an implantable lead assembly 1350, according to one example of the present disclosure. In some examples, the lead assembly 1350 comprises at least some of substantially the same features and attributes as lead assembly 1250 in FIG. 21B, except replacing the subassembly 1210 (including first FPE assembly 404, elongate support member 403, and tubular insulator 1202) with a lead subassembly 1310 (including FPE assembly 1304 and insulator 1302). Via this arrangement, lead assembly 1350 includes a first FPE assembly 1304 and a second FPE assembly 1260. In comparison to the lead assembly 1150 in FIG. 20, the lead assembly 1350 in FIG. 23 comprises at least substantially the same features except for having its internal FPE assembly 1304 being in an unwound configuration and with the FPE assembly 1304 defining the innermost component (e.g. the core) of the lead assembly 1350.

In some examples, in addition to FPE assembly 1260, an additional FPE assembly 1270 (FIG. 21C) or FPE assembly 1280 (FIG. 21D) is implemented in cooperation with FPE assembly 1260.

In some examples, the FPE assembly 1304 may be longer than the outer tubular insulator 1302 to facilitate flexing of the FPE assembly 1304, such as when implanting and/or maneuvering the lead assembly 1300. In some such examples, this relationship may be achieved via the FPE assembly 1304 protruding from an end of the tubular insulator 1302 and/or forming a portion of the FPE assembly 1304 (that extends within/through insulator 1302) to include at least one fold, undulation, etc. to enhance extensibility and/or flexing functionality for the FPE assembly 1304.

Figure 24:
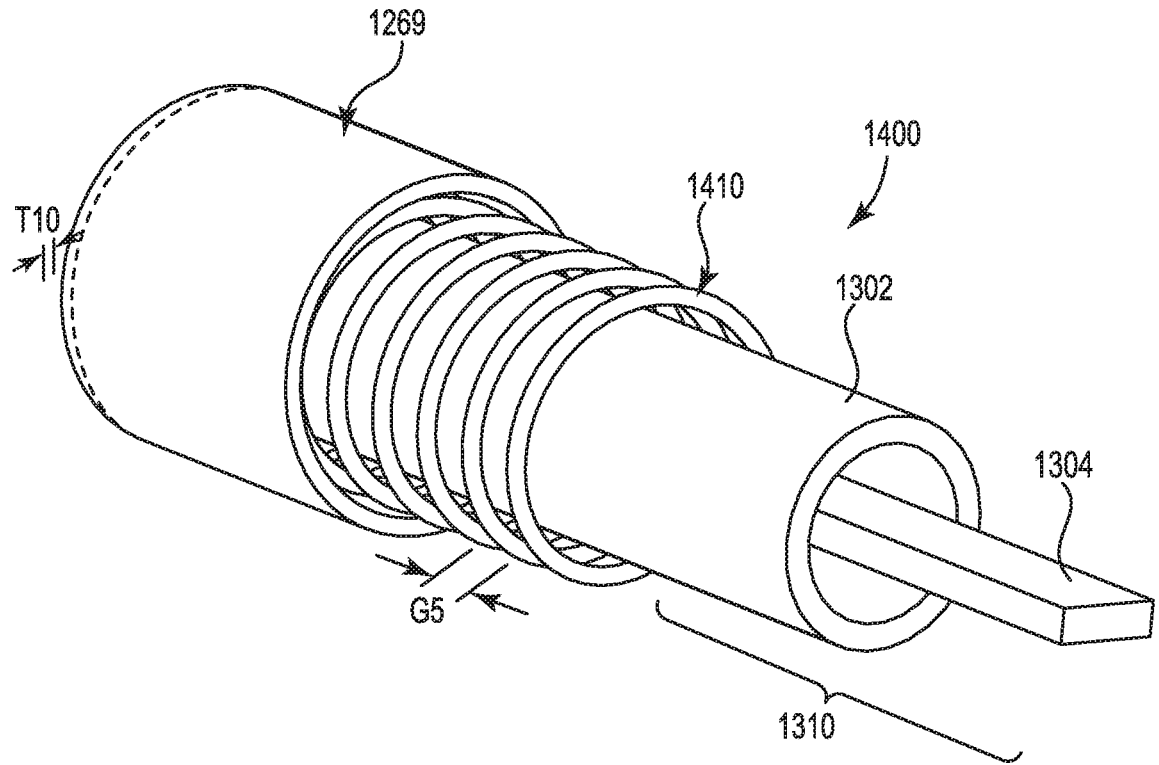
FIG. 24 is a perspective view schematically representing an implantable lead assembly including the lead assembly of FIG. 22B and further including at least an external coil shield, according to one example of the present disclosure.

FIG. 24 is a perspective view schematically representing an implantable lead assembly 1400, according to one example of the present disclosure. In some examples, the lead assembly 1400 comprises at least substantially the same features and attributes as lead assembly 1350 in FIG. 23, except for replacing the second FPE assembly 1260 with a coil 1410 like coil 1290 (FIG. 21H). In some examples, the lead assembly 1400 shown in FIG. 24 also can be regarded as comprising at least substantially the same features and attributes as lead assembly 1291 in FIG. 21H, except for replacing the lead subassembly 1210 (FIG. 21H) with lead subassembly 1310 (FIG. 23).

Via this arrangement, the coil 1410 provides an external shield while the FPE assembly 1304 may or may not include its own shielding and/or filtering functionality as implemented according to the various available modalities 212, 214, 216, 217 in FIG. 5A.

In some examples, lead assembly 1400 may be modified in a manner substantially the same as lead assembly 1295 (FIG. 22A) in which outer tubular insulator 1269 is eliminated and coil 1410 is modified to be wound in contact against, and/or within an outer surface 1203, tubular insulator 1203. Moreover, in some examples, the thickness (T10) of outer tubular insulator 1269 and/or the gap G5 may be minimized in order to increase capacitive coupling to body tissue, thereby enhancing shielding of RF energy.

Figure 25:
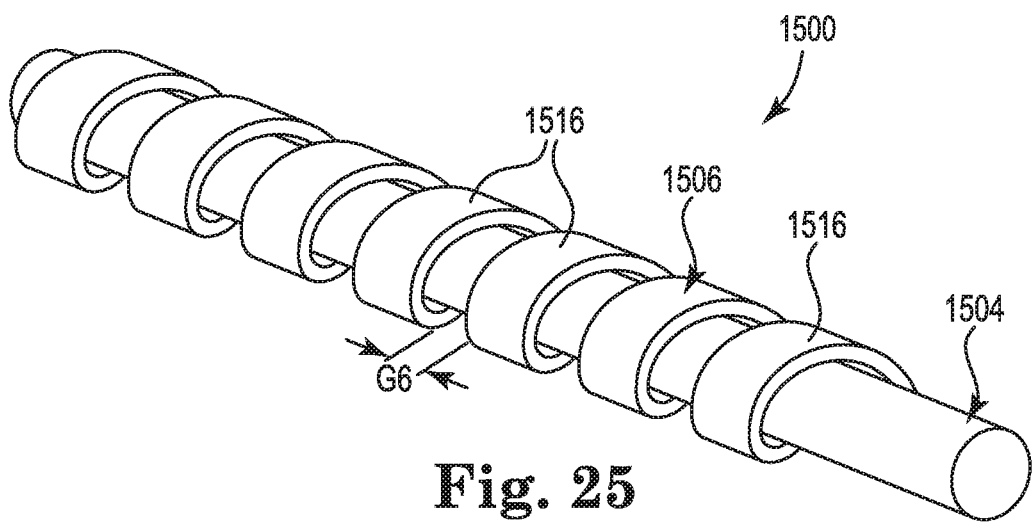
FIG. 25 is a perspective view schematically representing an implantable lead assembly including a FPE assembly in a helically wound configuration about a lead, according to one example of the present disclosure.

FIG. 25 is a perspective view schematically representing an implantable lead assembly 1500, according to one example of the present disclosure. In some examples, lead assembly 1500 includes a signal-carrying lead body 1504 (e.g. 72 in FIG. 2) about which is helically wound a FPE assembly 1506.

In some examples, the FPE assembly 1506 acts as an external shield (shield modality 210 in FIG. 5A) via the FPE assembly 1506 incorporating any or several of the attenuation modalities 212, 214, 216, 217 (FIG. 5A) as implementable via any (or combinations thereof) of the example FPE assemblies as described throughout various examples of the present disclosure. For instance, in some examples, the FPE assembly 1506 may include shield conductive elements 517A, 517B (FIG. 7A-7E) and in some examples, additionally includes additional shielding components, as in FIGS. 10-12 and 15-18. Moreover, in some examples the FPE assembly 1506 comprises inductive and/or capacitive attenuation elements 250, 252 (FIG. 5A).

However, in some examples, the FPE assembly 1506 omits an interior shield element, such as second shield conductive element 517B (and outer insulator 520B in FIG. 16), such that shielding functionality is provided on just one side (e.g. the exterior portion) of the FPE assembly such as via first shield conductive element 517A, as shown in FIG. 7D.

In addition, to the extent that the FPE assembly 1506 is constructed with a spacing G6 that is sufficiently small, such as at least one order of magnitude less than a wavelength of the MRI-energy field signals (within the body), then its helically wound configuration further enhances the attenuation functionality of FPE assembly 1506 relative to lead body 1504.

Meanwhile, the lead body 1504 is constructed without a FPE assembly, and includes at least one signal conductive element extending a length of the lead body 1504 to convey a sensing signal and/or stimulation signal and includes at least an outer insulator.

At least some example implementations of lead body 1504 are provided in association with at least FIGS. 26-33.

Figure 26:
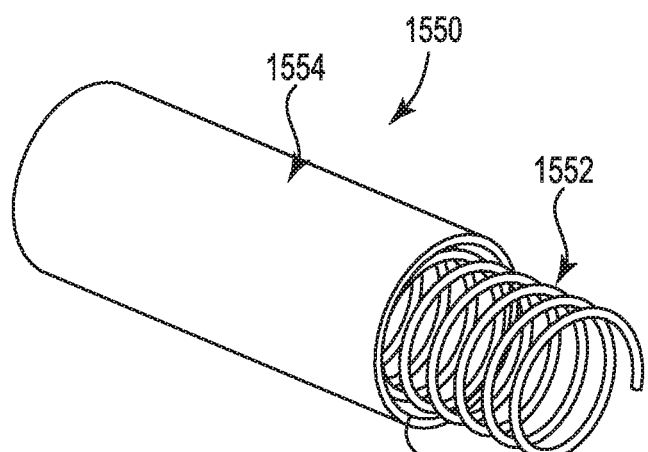
FIG. 26 is a perspective view schematically representing one example implementation of the lead of FIG. 25, according to one example of the present disclosure.

FIG. 26 is a perspective view schematically representing a lead body 1550, according to one example of the present disclosure. In some examples, lead body 1550 comprises one example implementation of lead body 1504 in FIG. 25. As shown in FIG. 26, lead body 1550 comprises a signal conductor 1552 in a coiled or helically wound configuration and extending within a lumen 1555 throughout a length of an outer tubular insulator 1554. The signal conductor 1552 can convey sensing signals and/or stimulation signals along the length of lead body 1550, such as lead 72 in FIG. 2.

Figure 27:
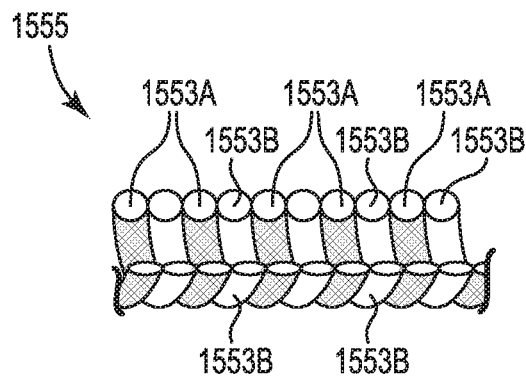
FIG. 27 is a sectional view schematically representing one example implementation of a co-radial configuration of a pair of signal conductive elements, according to one example of the present disclosure.

In some examples, the signal conductor 1552 comprises a co-radial arrangement in which two different signal conductors 1553A, 1553B extend as part of the same coiled configuration, as further shown in the partial sectional view of FIG. 27. As shown in FIG. 27, the respective different signal conductors 1553A, 1553B are in an interleaved (e.g. alternating) arrangement such that a single coil structure 1555 includes two different (e.g. independent signal conductors). The respective signal conductors 1553A, 1553B can separately convey sensing signals and/or stimulation signals along the length of lead body 1550, such as lead 72 in FIG. 2.

Figure 28:
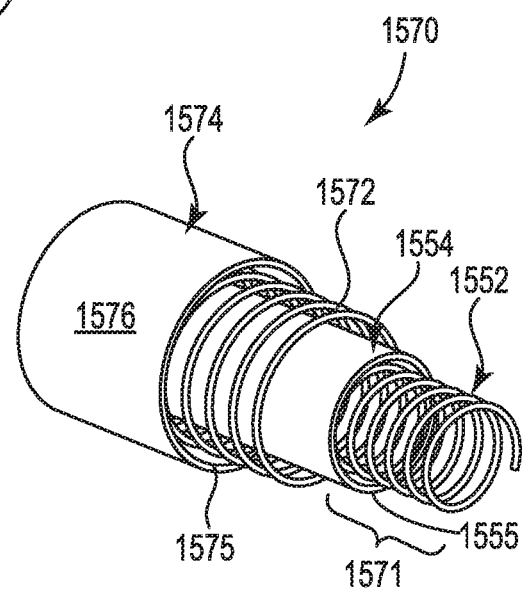
FIG. 28 is a perspective view schematically representing an implantable lead assembly including the lead assembly of FIG. 26 and further including at least an external coil shield, according to one example of the present disclosure.

FIG. 28 is a perspective view schematically representing an implantable lead assembly 1570 including a lead body subassembly 1571 and an external coil shield 1572, according to one example of the present disclosure. In some examples, lead body subassembly 1571 comprises one example implementation of lead body 1504 in FIG. 25. As shown in FIG. 28, lead assembly 1570 comprises the components of lead body 1550 in FIG. 26, and additionally comprises an external conductive coil 1572 (e.g. helically wound configuration) wound about tubular insulator 1554 and a second outer tubular insulator 1574. The external coil 1572 corresponds to at least shield modality 210 of attenuation arrangement 204 in FIG. 5A.

FIG. 29 is a sectional view schematically representing a lead body 1700, according to one example of the present disclosure. In some examples, lead body 1700 comprises one example implementation of lead body 1504 (at least FIG. 25). As shown in FIG. 29, lead body 1700 includes a pair of signal conductive elements 1702A, 1702B arranged in a spaced apart, side by side arrangement such that signal conductive elements 1702A, 1702B would extend side-by-side along a length of the lead body 1700. In some examples, the spacing W5 between signal conductive elements 1702A, 1720B is minimized in order to reduce the total cross-sectional area between them, which in turn, may reduce susceptibility to inductive coupling of energy on to the signal conductive elements 1702A, 1702B. In some examples, each signal conductive element 1702A, 1702B can take the form of a coil, such as but not limited to, the arrangement in FIG. 9. In some examples, the spacing between the conductive elements 1702A, 1702B in three dimensions can be minimized in order to reduce the total cross-sectional area between them.

FIG. 30 is a sectional view schematically representing a lead body 1750, according to one example of the present disclosure. In some examples, lead body 1750 comprises one example implementation of lead body 1504 (at least FIG. 25). As shown in FIG. 30, lead body 1750 includes an inner signal conductive element 1752A and outer signal conductive element 1752B in a coaxial arrangement. In some examples, either or both signal conductive element 1752A, 1752B can take the form of a coil. As shown in FIG. 30, in some examples, the inner signal conductive element 1752A can take the form of a solid cylindrical member, and therefore having a generally circular cross-section as shown in FIG. 30.

FIG. 31A is a perspective view schematically representing an implantable lead assembly 1900, according to one example of the present disclosure. In some examples, lead assembly 1900 comprises a lead subassembly 1910 (e.g. lead assembly 1500 in FIG. 25) and further comprises an outer tubular insulator 1902 having an array 1920 of windows 1922A, 1922B, 1922C. In one aspect, the presence of the outer tubular insulator 1902 surrounding the lead subassembly 1910 may limit fibrotic tissue growth on FPE assembly 1506 and/or the lead body 1504, while the windows 1922A, 1922B, 1922C make contact with surrounding body tissue to facilitate dissipation of energy generated from the MRI signals during MR scanning.

In some examples, at least some of the windows 1922A, 1922B, 1922C may have shapes (e.g. circular, triangular, etc.) other than the rectangular shaped shown in FIG. 31A.

In some examples, regardless of the particular shape, at least some of the windows 1922A, 1922B, 1922C may define area which is substantially smaller than shown in FIG. 31A, which may facilitate capacitive dispersion of RF energy. In some such examples, at least some of the respective windows would be too small to permit the arrangement described and shown in FIG. 31B.

FIG. 31B is a sectional view schematically representing a relationship of an outer surface of an external coil relative to a window of the outer flexible tubular insulator, according to one example of the present disclosure. In some examples, the arrangement 1940 shown in FIG. 31B may correspond to one example implementation as taken along line 31B of FIG. 31A. However, the arrangement 1940 in FIG. 31B is not necessarily an exclusive representation of the arrangement in FIG. 31A.

As shown in FIG. 31B, at least some windings 1516 of FPE assembly 1506 include a conductive protrusion 1950 sized and shaped to extend at least partially through one of the windows (e.g. 1922A) of outer tubular insulator 1902 and beyond outer surface 1903 of outer tubular insulator 1902. It will be understood that where multiple windows (e.g. 1922A, 1922B, 1922C) are present, a respective protrusion 1950 may be implemented for each window or for just some windows.

In some examples, the conductive protrusion 1950 is printed as part of formation of the FPE assembly 1506. In some examples, the conductive protrusion is secured to the outer surface of the FPE assembly 1506. In some examples, the protrusion 1950 comprises an electrode.

In some examples, the arrangement includes at least one tab 1960 to facilitate positioning the protrusion 1950 within and/or through the at least one window (e.g. 1922A) and then to advance the protrusion 1950 through the at least one window (e.g. 1922A). In some examples, the tab 1960 is adhesively secured relative to the protrusion 1950 or onto the winding 1516 of FPE assembly 1506 nearby the at least one protrusion 1950.

In some examples, the tab 1960 and/or the protrusion 1950 are secured relative to the outer surface of (one of the windings 1516) the FPE assembly 1506 via a very thin non-conductive sleeve.

Figure 32:
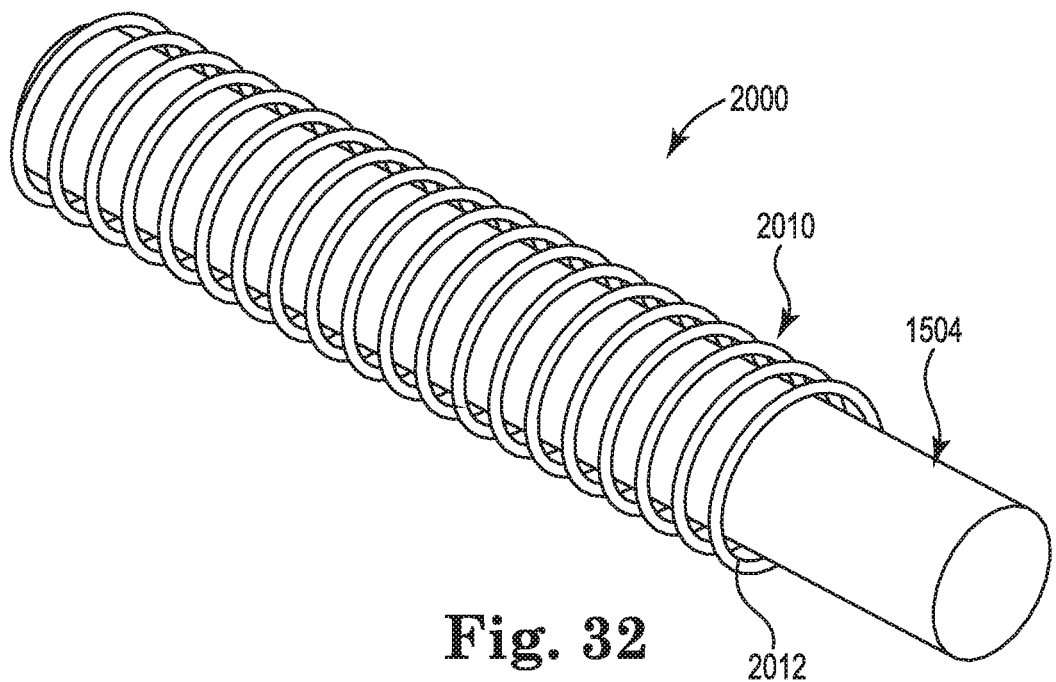
FIG. 32 is a perspective view schematically representing an implantable lead assembly including a lead and an external coil shield, according to one example of the present disclosure.

FIG. 32 is a perspective view schematically representing an implantable lead assembly 2000, according to one example of the present disclosure. As shown in FIG. 32, in some examples lead assembly 2000 includes lead body 1504 and an external coil 2010 defining a passage 2012 or lumen through which the lead body 1504 extends. The external coil 2010 corresponds to at least the external shield modality 210 in the attenuation arrangement of FIG. 5A, and therefore acts to attenuate MRI-energy relative to the lead body 1504. In some examples, the external coil 2010 may be coated with a biocompatible, non-conductive material to minimize the introduction of additional conductive pathways and associated undesired electromagnetic interactions.

In some examples, the external coil 2010 may be implemented as two opposing coils having at least some of substantially the same features and attributes as the outer coil 4610 and intermediate coil 4620 in FIG. 20F.

Figure 33:
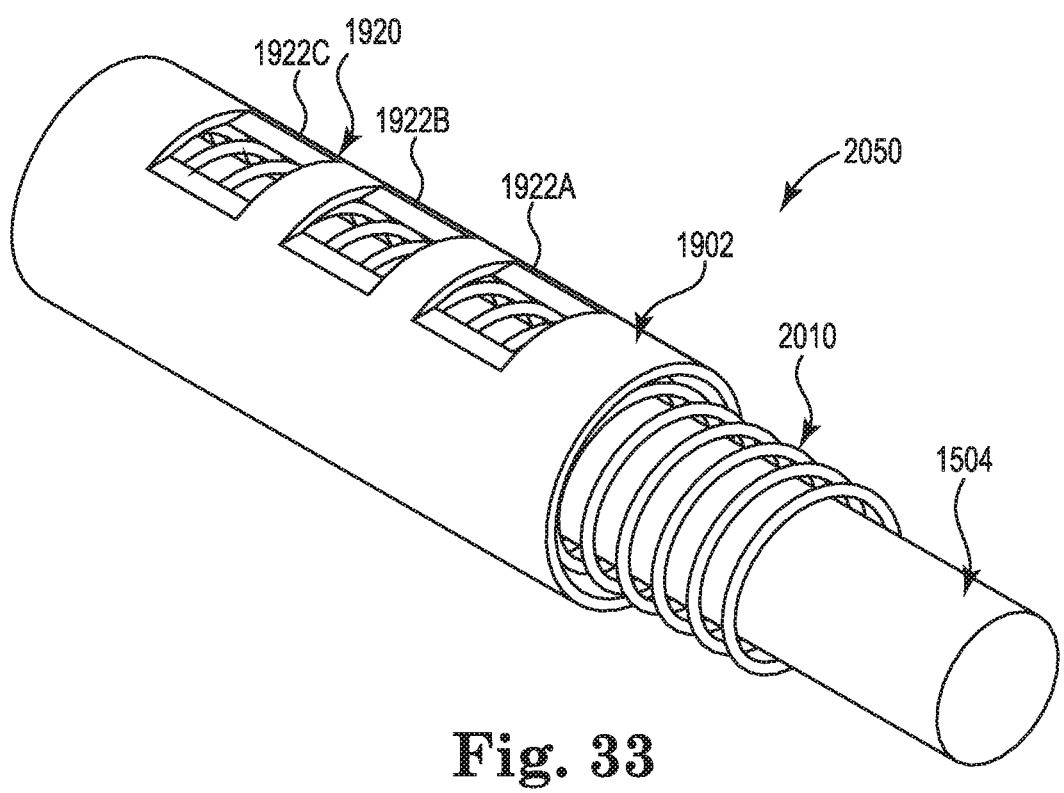
FIG. 33 is a perspective view schematically representing an implantable lead assembly including the lead assembly of FIG. 32 and further including an outer flexible tubular insulator having windows, according to one example of the present disclosure.

FIG. 33 is a perspective view schematically representing an implantable lead assembly 2050, according to one example of the present disclosure. In some examples, lead assembly 2050 comprises substantially the same features and attributes as lead assembly 2000 in FIG. 32, except further comprising an outer tubular insulator 1902 having substantially the same features and attributes as the outer tubular insulator 1902 in FIG. 31. Accordingly, the outer tubular insulator 1902 may limit fibrotic growth, reduce tissue irritation, and improve lead handling and/or tunneling characteristics on coil 2010 while windows 1922A, 1922B, 1922C permit dissipation of energy (resulting from MRI signals) into the surrounding body tissue.

FIG. 34 is a flow diagram schematically representing a method 2400, according to one example of the present disclosure. In some examples, at least some aspects of method 2400 may be implemented via at least some of the systems, devices, leads, assemblies, modalities, elements, structures, arrangements, functions, parameters, etc. as described in association with at least FIGS. 1-33. In some examples, at least some aspects of method 2400 may be implemented via at least some systems, devices, leads, assemblies, modalities, elements, structures, arrangements, functions, parameters, etc. other than those described in association with at least FIGS. 1-33.

In some examples, as shown at 2402 method 2400 comprises providing an implantable medical device having at least one signal conductor. At 2404, method 2400 comprises arranging an attenuation arrangement in association with at least a portion of the implantable medical device to attenuate external RF energy. In some examples, one portion of the implantable medical device (with which the attenuation arrangement is associated) comprises a lead, such as a lead extendible between two other elements, such as an implantable electrode and an implantable monitor and/or pulse generator. In some examples, the implantable medical device (with which the attenuation arrangement is associated) comprises an electrode, which may comprise at least one electrode contact. The electrode may be for sensing and/or stimulation. In some examples, the implantable medical device (with which the attenuation arrangement is associated) comprises a monitor and/or pulse generator. In some examples, the implantable medical device comprises a combination of the lead, electrode, and pulse generator (or monitor). FIG. 35 is a flow diagram schematically representing a method 2500, according to one example of the present disclosure.

In some examples, at least some aspects of method 2500 may be implemented via at least some of the systems, devices, leads, assemblies, modalities, elements, structures, arrangements, functions, parameters, etc. as described in association with at least FIGS. 1-34. In some examples, at least some aspects of method 2500 may be implemented via at least some systems, devices, leads, assemblies modalities, elements, structures, arrangements, functions, parameters, etc. other than those described in association with at least FIGS. 1-34.

In some examples, method 2500 comprises at least some of substantially the same features and attributes as method 2400 (FIG. 36) and comprises one example implementation of at least some aspects of method 2400.

In some examples, at 2502 method 2500 comprises implanting an implantable medical device having at least one signal conductor. In some examples, the implantable medical device may comprise a lead, electrode, and/or pulse generator, such as previously described in association with at least FIG. 36.

In some examples, at 2504 method 2500 comprises attenuating external RF energy relative to at least the at least one signal conductor of the implantable medical device.

In some examples, the attenuating of external RF energy may be implemented via shielding RF energy (at 2512), filtering or dissipating RF energy (at 2514), and/or via anti-phase cancellation of RF energy (at 2516). In some examples, such implementation may occur via at least some of the aspects described in association with at least FIGS. 5A-5D, and more specific implementations described in association with at least FIGS. 6A-33.

In some examples, the shielding of RF energy (2512) may be implemented externally to the implantable medical device (at 2522) and/or implemented internally within the implantable medical device (at 2524).

In some examples, the attenuating of external RF energy (at 2504) may be implemented via flexible printed electronics (FPE), such as via at least some aspects of the various FPE arrangements described throughout the present disclosure. However, in some examples, the attenuating of external RF energy (at 2504) may be implemented via arrangements (as described throughout examples of the present disclosure) other than flexible printed electronics (FPE). In some examples, the attenuating of external RF energy may be implemented via a combination of flexible printed electronics (FPE) and non-FPE arrangements.

Although specific examples have been illustrated and described herein, a variety of alternate and/or equivalent implementations may be substituted for the specific examples shown and described without departing from the scope of the present disclosure. This application is intended to cover any adaptations or variations of the specific examples discussed herein.

The invention claimed is:

1. An implantable lead assembly comprising:
a lead including a first elongate flexible printed electronic assembly, which includes a first signal conductive element; and
at least one attenuation arrangement to attenuate MRI-energy, wherein the at least one attenuation arrangement includes a first portion formed as part of the elongate flexible printed electronic assembly, and wherein the first portion is electrically isolated from the first signal conductive element in the elongate flexible printed electronic assembly, and further wherein the first portion includes an active filter component.

2. The implantable lead assembly of claim 1, wherein the first elongate flexible printed electronic assembly comprises a base insulator onto which the first signal conductive element is printed.

3. The implantable lead assembly of claim 2, wherein the at least one attenuation arrangement includes a second portion printed over the first signal conductive element such that the second portion directly contacts the first signal conductive element.

4. The implantable lead assembly of claim 2, wherein the first flexible printed electronic assembly comprises at least the first signal conductive element, the base insulator, and the first portion of the at least one attenuation arrangement formed together as a monolithic structure.

5. The implantable lead assembly of claim 1, wherein the at least one attenuation arrangement comprises a second portion external to, and spaced apart from, the first flexible printed electronic assembly.

6. The implantable lead assembly of claim 1, wherein the at least one attenuation arrangement comprises a second portion comprising a conductive coil generally co-extensive with at least a portion of a length of the first flexible printed electronic assembly, and wherein the second portion of the at least one attenuation arrangement is external to and spaced apart from the first flexible printed electronic assembly.

7. The implantable lead assembly of claim 1, wherein the at least one attenuation arrangement comprises a second portion selected from the group consisting of, a shield, and an anti-phase arrangement.

8. The implantable lead assembly of claim 7, wherein the anti-phase arrangement comprises a conductive arrangement including at least one of:
a pair of first and second conductive structures arranged to alternate, in a repeating pattern, between an inside position and an outside position along a length of the anti-phase attenuation arrangement; and
at least one conductor forming a forward-extending array of loops, wherein at least some of the loops comprise capacitive functionality.

9. The implantable lead assembly of claim 7, wherein the lead comprises an electrode for sensing and/or stimulation, and wherein the conductive arrangement of the anti-phase arrangement is separate from, and independent of, the first signal conductive element to which the electrode is electrically connected.

10. The implantable lead assembly of claim 7, wherein the shield is external to the first signal conductive element, and the shield comprises adjacent conductive elements having a spacing therebetween at least one order of magnitude less than a wavelength of an MM field signal within the body.

11. The implantable lead assembly of claim 1, wherein the first flexible printed electronic assembly is in a helically wound configuration comprising a continuous coil of windings spaced apart from each other by a first distance, and wherein the first distance is at least one order of magnitude less than a wavelength of a MRI field signal within the body, and wherein the implantable lead assembly further comprises an elongate support member about which the helically wound configuration is formed.

12. The implantable lead assembly of claim 1, wherein the at least one attenuation arrangement comprises:
a second portion arranged as a first coil at least partially co-extensive with the first flexible printed electronic assembly,
wherein the first coil is external to and spaced apart from the first flexible printed electronic assembly with a first tubular insulator interposed between the first flexible printed electronic assembly and the first coil.

13. The implantable lead assembly of claim 12, wherein the second portion of the at least one attenuation arrangement comprises a second flexible printed electronic assembly, which omits signal conductive elements.

14. The implantable lead assembly of claim 12, wherein the least one attenuation arrangement comprises:
a third portion arranged as a second coil at least partially co-extensive with the first flexible printed electronic assembly and with the first coil, wherein the second coil has a second winding orientation opposite a first winding orientation of the first coil.

15. The implantable lead assembly of claim 14, wherein the third portion of the at least one attenuation arrangement comprises a third flexible printed electronic assembly, which omits signal conductive elements.

16. The implantable lead assembly of claim 1, and further comprising a system including:
an implantable pulse generator having a housing having an exterior surface which includes at least a portion which is electrically conductive and to which the end of at least a portion of the first flexible printed electronic assembly is electrically coupled.

17. The implantable lead assembly of claim 1, comprising:
an electrode at an end of the first flexible printed electronic assembly, wherein the at least one attenuation arrangement comprises a second portion co-extensive with at least a length of the electrode.

18. The implantable lead assembly of claim 1, wherein the first flexible printed electronic assembly comprises a second signal conductive element and wherein at least a portion of a base insulator is sandwiched between the respective first and second signal conductive elements, and wherein the at least one attenuation arrangement comprises a second portion, the second portion comprising a conductive shield at least partially surrounding at least one of the first and second signal conductive elements.

19. The implantable lead assembly of claim 18, wherein the first flexible printed electronic assembly comprises:
a first insulator external to the first signal conductive element; and
a second insulator external to the second signal conductive element.

20. The implantable lead assembly of claim 19, wherein the conductive shield comprises the first flexible printed electronic assembly including:
a first shield conductive element external to the first insulator;
a second shield conductive element external to the second insulator;
a third insulator external to the first shield conductive element; and
a fourth insulator external to the second shield conductive element.

21. The implantable lead assembly of claim 1, comprising a flexible elongate non-conductive support member, which comprises a tubular structure defining a lumen, wherein the first flexible printed electronic assembly is positioned within the lumen and extends throughout a length of the lumen.

* * * * *